United States Patent [19]

Huntsman et al.

[11] Patent Number: 4,796,634

[45] Date of Patent: Jan. 10, 1989

[54] METHODS AND APPARATUS FOR MONITORING CARDIAC OUTPUT

[75] Inventors: Lee L. Huntsman, Bainbridge Island; Richard S. Leard, Issaquah; Gary L. Tarbox, Bainbridge Island; Stephen R. Barnes, Seattle; Barry D. McLaren, Auburn, all of Wash.

[73] Assignee: Lawrence Medical Systems, Inc., Camarillo, Calif.

[21] Appl. No.: 763,992

[22] Filed: Aug. 9, 1985

[51] Int. Cl.[4] .............................................. A61B 10/00
[52] U.S. Cl. ........................... 128/662.01; 364/413.07
[58] Field of Search .............................. 128/663, 713; 364/415–417

[56] References Cited

U.S. PATENT DOCUMENTS

| | | |
|---|---|---|
| 3,732,532 | 5/1973 | Flaherty . |
| 3,777,740 | 12/1973 | Hokanson . |
| 3,779,234 | 12/1973 | Eggleton et al. . |
| 3,780,725 | 12/1973 | Goldberg . |
| 3,817,089 | 6/1974 | Eggleton et al. . |
| 3,859,984 | 1/1975 | Langley . |
| 3,938,502 | 2/1976 | Bom . |
| 4,142,412 | 3/1979 | McLeod et al. . |
| 4,176,660 | 12/1979 | Mylrea et al. . |
| 4,183,353 | 1/1980 | Gallub . |
| 4,237,729 | 12/1980 | McLeod et al. . |
| 4,259,870 | 4/1981 | McLeod et al. . |
| 4,319,580 | 3/1982 | Colley et al. . |
| 4,320,765 | 3/1982 | Cathignol et al. . |
| 4,354,500 | 10/1982 | Colley et al. . |
| 4,354,501 | 10/1982 | Colley et al. . |
| 4,354,502 | 10/1982 | Colley et al. . |
| 4,413,629 | 11/1983 | Durley, III . |
| 4,417,584 | 11/1983 | Cathignol et al. . |
| 4,433,691 | 2/1984 | Bickman . |
| 4,442,842 | 4/1984 | Baba . |
| 4,462,408 | 7/1984 | Silverstein et al. . |
| 4,466,443 | 8/1984 | Utsugi . |
| 4,509,526 | 4/1985 | Barnes et al. . |

FOREIGN PATENT DOCUMENTS

| | | |
|---|---|---|
| 2352286 | 12/1977 | France . |
| 2424733 | 11/1979 | France . |
| 2447041 | 8/1980 | France . |
| 2506472 | 11/1982 | France . |
| 2525460 | 10/1983 | France . |

OTHER PUBLICATIONS

Keats, T. E. et al., "Atlas of Roentgevographic Measurement," Yearbook Publishers, Chicago ©1985 pp. 310.

Bugni, W. J. "Iwasive Exercise Testing", in Cardiology Clinics vol. 2 No. 3 Aug. 1984, W. B. Saunders & Co., Chicago, p. 468.

Cross, G. et al., "Non–Iwasive Intra–Thoracic BV Measurement," Biomed Engrg 1974 pp. 464–470.

Arkin, H. et al., "Statistical Methods", Barnes & Noble N.Y. 201 1970 p. 245.

Lavandier, B. et al., "Non–Iwasive Aortic BF Measurement", UTS in Medicine & Biology May/Jun. 1985 vol. 11, No. 3.

Cathignol et al., An Implantable Directional Doppler Flowmeter, Biotelemetry II, 2nd Int. Symp., Davos (May 20–24, 1974), pp. 16–18.

Cathignol et al., Transcutaneous Blood Flow Measurements Using Pseudorandom Noise Doppler System, IEEE Transactions on Biomedical Engineering, vol. BME–27, No. 1, Jan. 1980, pp. 30–36.

(List continued on next page.)

Primary Examiner—Francis J. Jaworski
Attorney, Agent, or Firm—Hughes, Cassidy & Multer

[57] ABSTRACT

A method and apparatus for ascertaining the cardiac output of a human patient, said method comprising the steps of: measuring the systolic velocity of the blood flowing through the patient's descending aorta; determining the cross-sectional area of the patient's ascending aorta; and calculating the patient's cardiac output from said systolic velocity and said aortic area. The cardiac output can be converted: (1) to cardiac index by dividing it by the patient's body surface area, and (2) to systemic vascular resistance by dividing a value representing the patient's blood pressure by said cardiac output.

21 Claims, 42 Drawing Sheets

OTHER PUBLICATIONS

Demer et al., An Esophageal Multiprobe for Temperature, Electrocardiogram, and Heart and Lung Sounds Measurements, IEEE Transations on Biomedical Engineering, vol. BME-25, No. 4, Jul. 1978, pp. 377–380.

Duck et al., An Esophageal Doppler Probe for Aortic Flow Velocity Monitoring, Ultrasound in Medicine and Biology, vol. 1, 1974, pp. 233–241.

Duck et al., An Intravenous Doppler Probe For Arterial Flow Monitoring, The Third International Conference on Medical Physics, Including Medical Engineering, Chalmers University of Technology, Goteborg, Sweden, 1972.

Fourcade et al., Validation de la debitmetrie aortique par capteur ultrasonore oesophagien dans la surveillance hemodynamique non sanglante, Societe de reanimation de langue francaise, Bordeaux, 30–31, mai 1980.

Frazin et al., Esophageal Echocardiography, Circulation, vol. 54, No. 1, Jul. 1976, pp. 102–108.

Geddes et al., Attenuation and Speed of 10 MHz Ultrasound in Canine Blood of Various Packed-Cell Volumes at 37° C., Medical and Biological Engineering and Computing, Sep. 1979, pp. 619–622.

Hisanaga, et al., High Speed Rotating Scanner for Transesophageal Cross-Sectional Echocardiography, The American Journal of Cardiology, vol. 46, Nov. 1980, pp. 837–842.

Macpherson et al., Angioscan: A Spectrum Analyser For Use With Ultrasonic Doppler Velocimeters, Journal of Medical Engineering & Technology, vol. 5, No. 2, Mar. 1981, pp. 84–85.

Miller et al., The Chronic Measurement of Local Flow Properties In the Abdominal Aorta of Dogs, Medical Research Engineering, Jul.-Aug., 1972, pp. 17–23.

Nealeigh et al., A Venous Pulse Doppler Catheter-Tip Flowmeter For Measuring Arterial Blood Velocity, Flow and Diameter In Deep Arteries, Proceedings of the 12th Annual Rocky Mountain Bioengineering Symposium and the 12th International ISA Biomedical Sciences Instrumentation Symposium, Denver, CO, U.S.A., Apr. 1975, pp. 7–10.

Souquet et al., Transeosophageal Phased Array For Imaging The Heart, IEEE Transaction on Biomedical Engineering, vol. BMI-29, No. 10, Oct. 1982, pp. 707–712.

Wells, et al., Ultrasonic Transesophageal Measurement Of Cardiac Output, 1978 Advances in Bioengineering, San Francisco, CA, U.S.A., Dec. 10–15, 1978, pp. 121–123.

Winter et al., Ultrasonic Detection of Cardiovascular Flow Disturbances, ISA Transactions, vol. 15, No. 3, 1976, pp. 237–241.

Advancing Cardiac Ultrasound, CardioVue 3400R, Diasonics Cardio/Imaging, Inc., 2341 South 2300 West, Salt Lake City, Utah 84119.

You Can Use Mon-A-Therm Disposable Temperature Sensors With Your Existing Monitoring Equipment, Mon-A-Therm, Inc., 520 South Jefferson Ave., St. Louis, MO 63103.

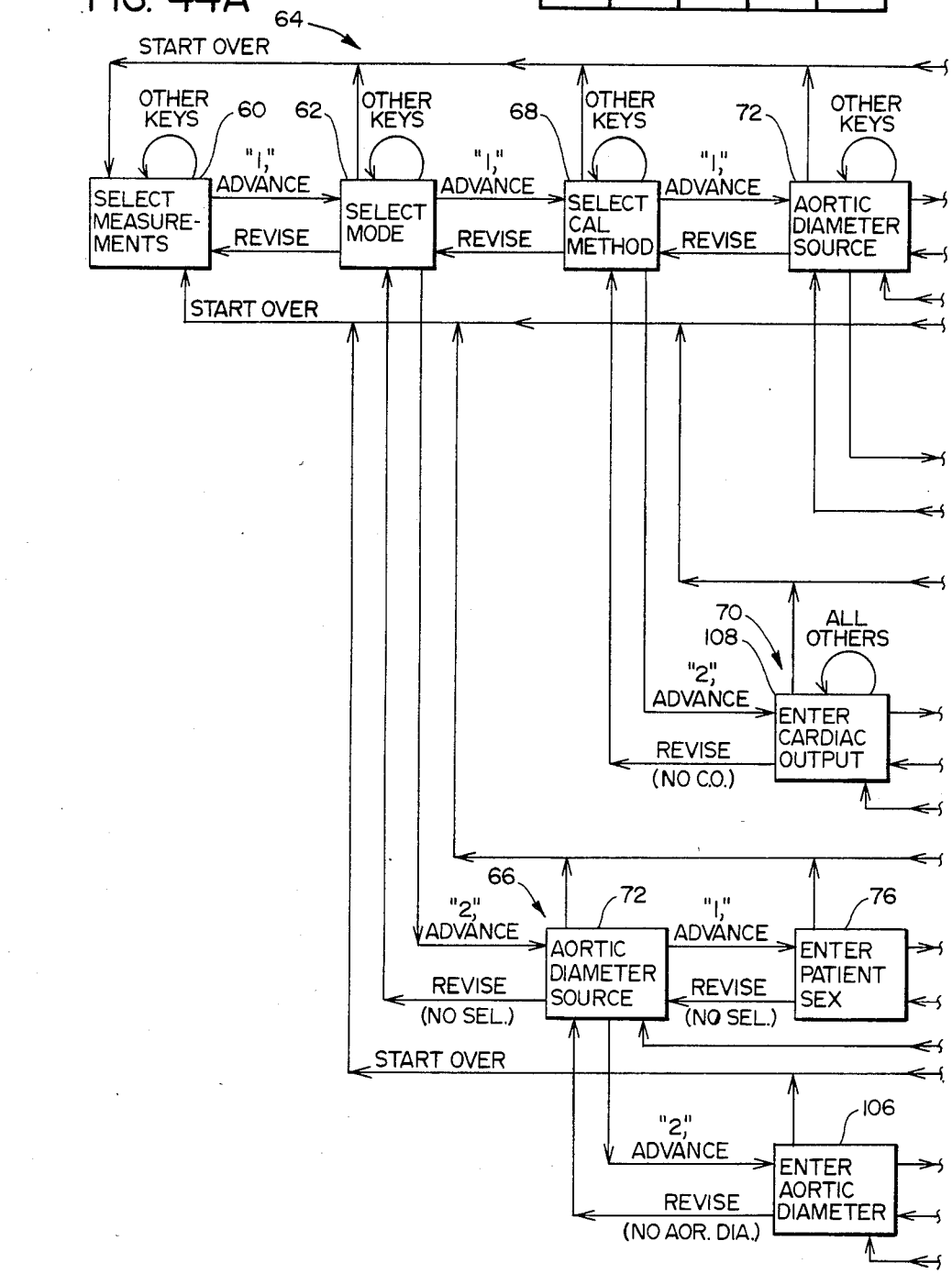

FIG. 44D
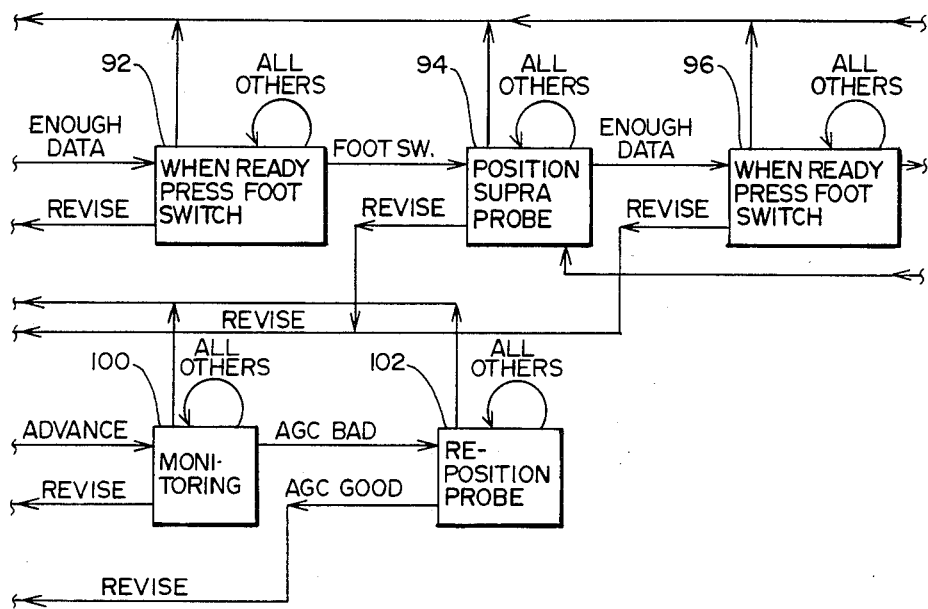
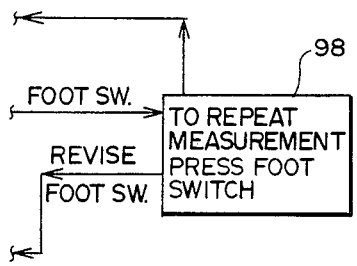

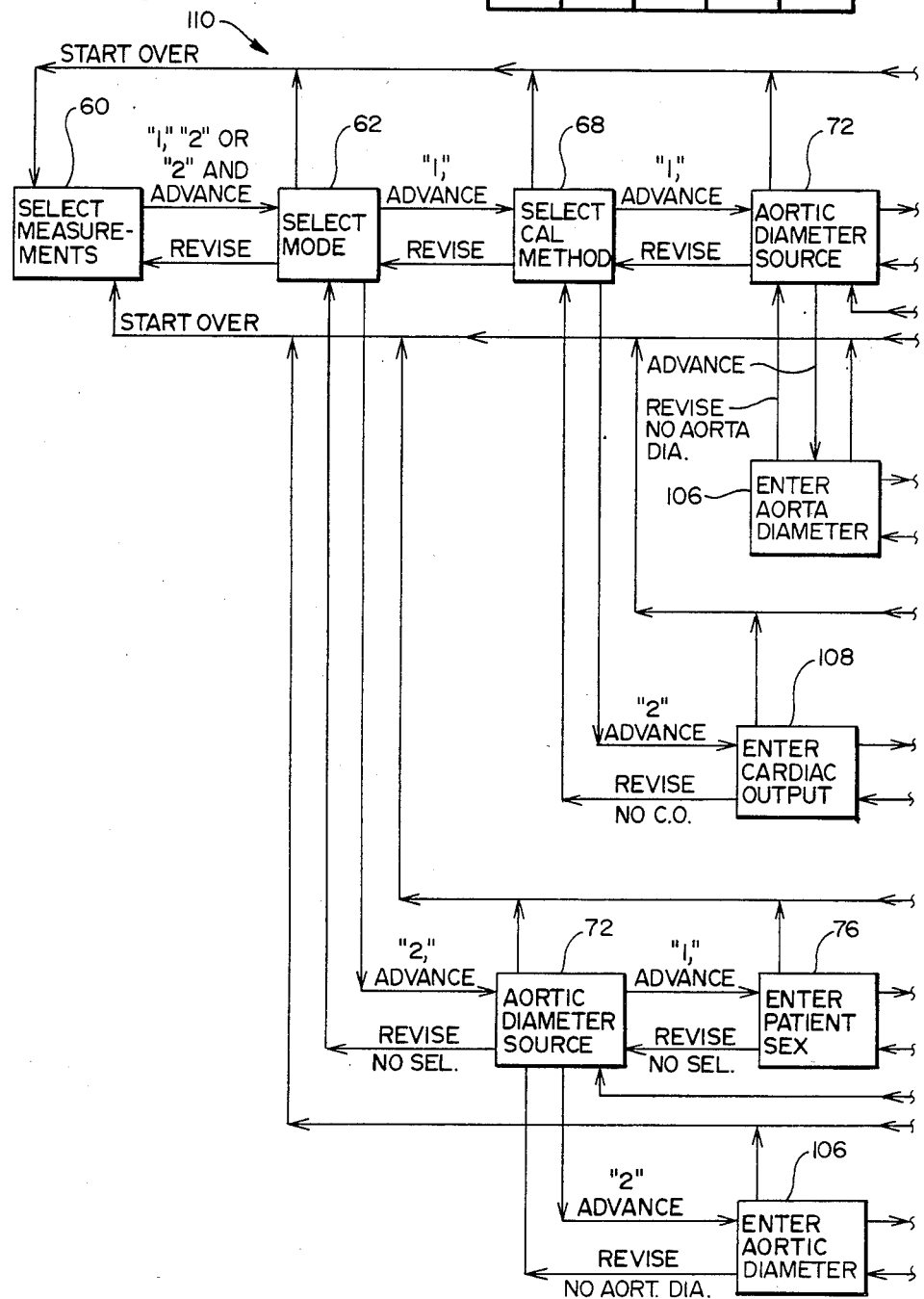

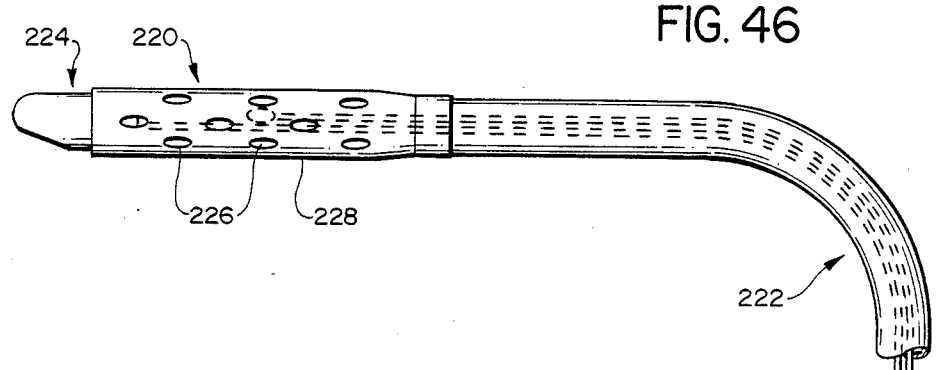
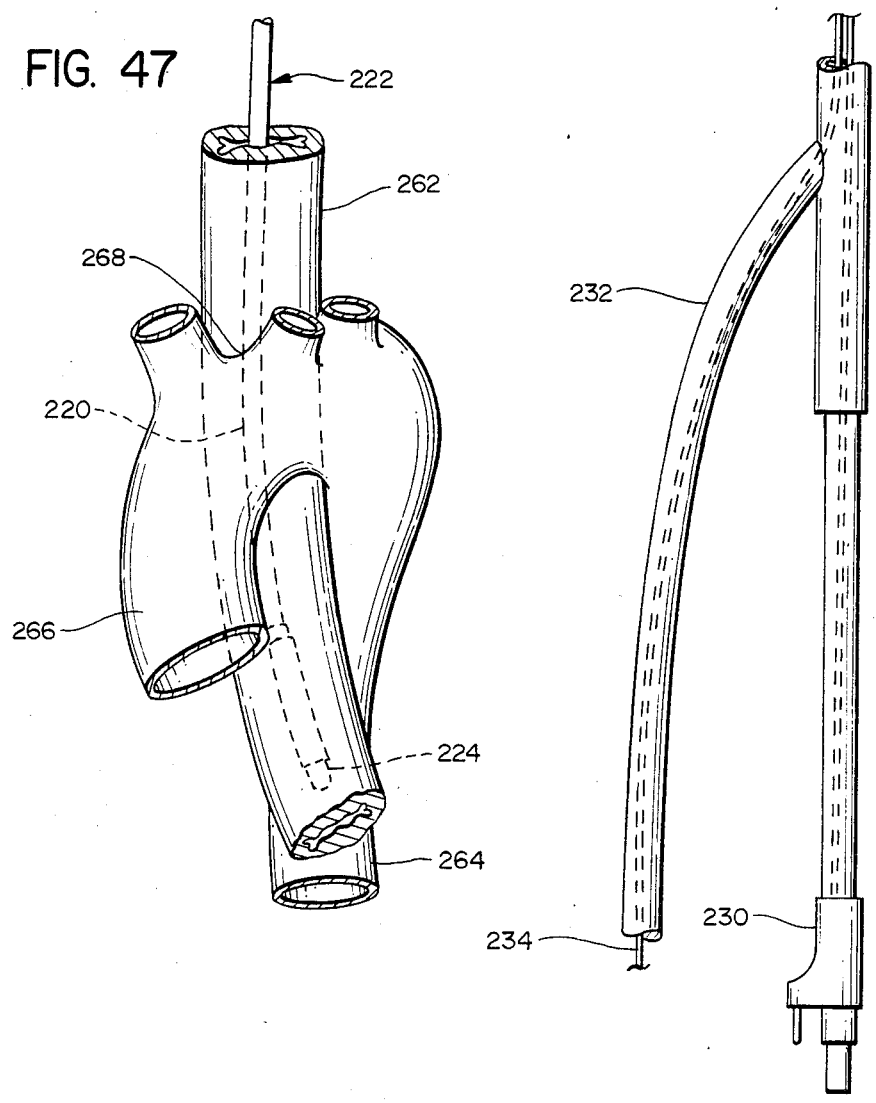
FIG. 46
FIG. 47

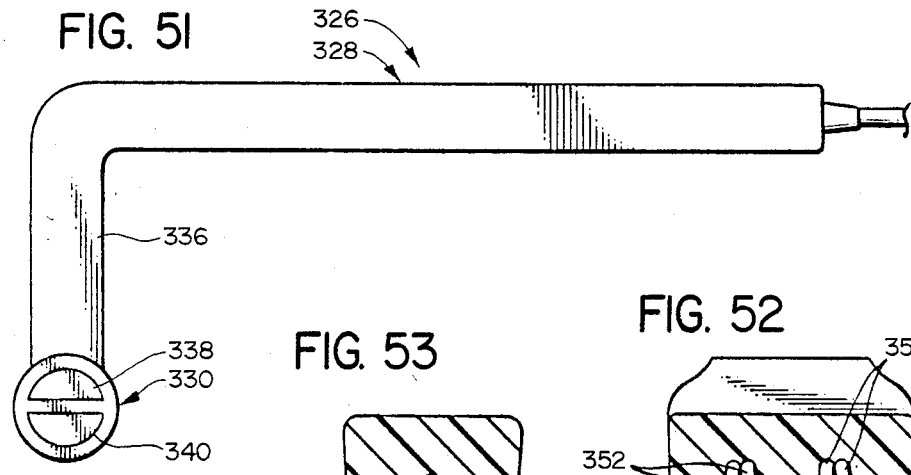
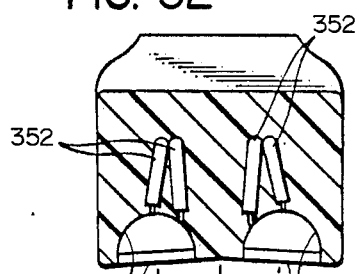
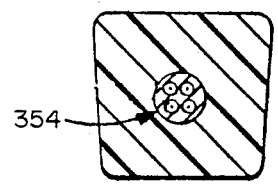
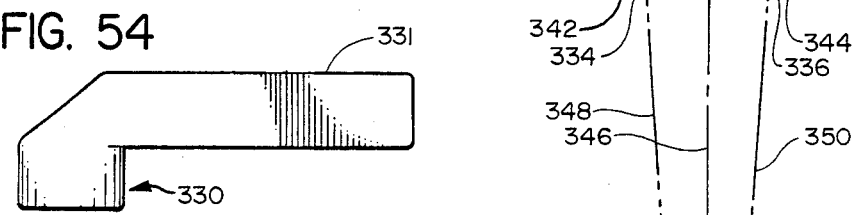
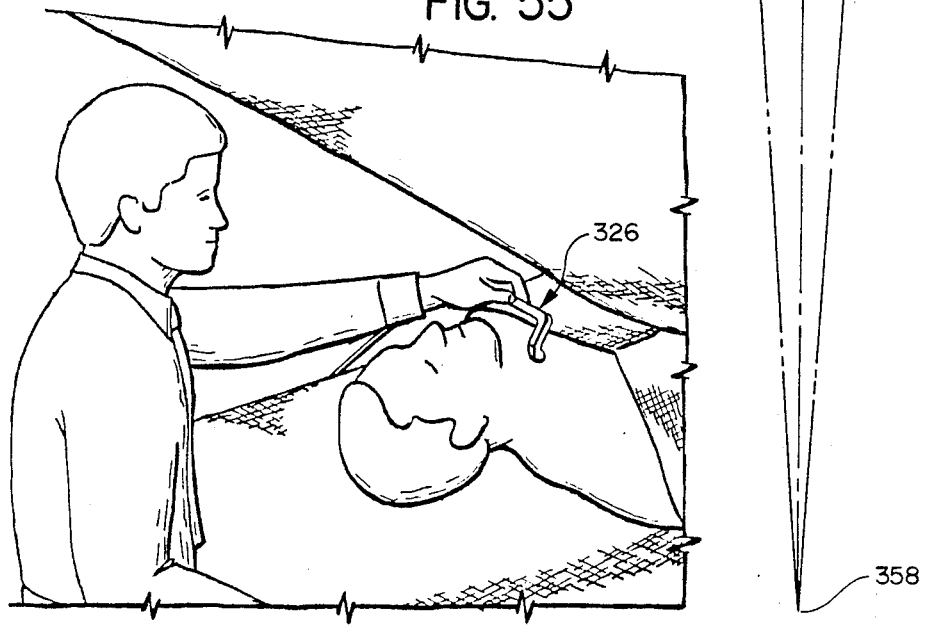

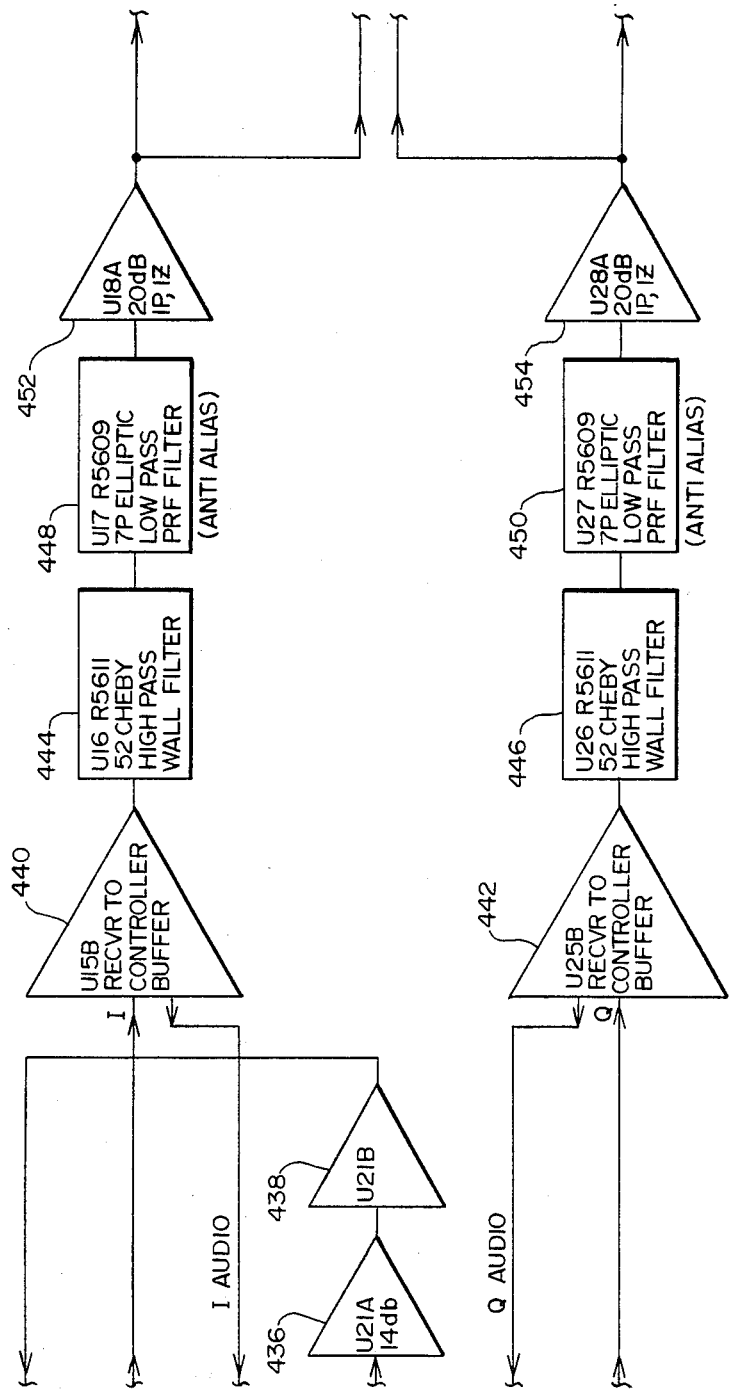

METHODS AND APPARATUS FOR MONITORING CARDIAC OUTPUT

TECHNICAL FIELD OF THE INVENTION

The present invention relates to novel, improved methods of and apparatus for monitoring the cardiac output of a mammalian patient.

BACKGROUND OF THE INVENTION

It is not uncommon for undetected bleeding to occur during surgical procedures because of an unintentionally severed vein or artery. The ensuing loss of blood can result in serious deterioration in the patient's condition, or even in death, if it is not promptly stemmed.

Blood pressure and pulse rate are monitored by the anethesiologist during a surgical procedure, and these parameters provide valuable information on the patient's condition. However, because systemic vascular resistance can increase dramatically during episodes of blood loss such as those just described, it may be as long as four or five minutes after serious bleeding develops or a blood vessel is severed before an appreciable decrease in pulse rate or blood pressure occurs. Currently, serious undetected losses of blood can occur in periods of this magnitude because as much as 35 percent of a patient's blood may be lost before there is a noticeable decrease in blood pressure. By then, however, the patient may be going into shock or suffering other complications attributable to the loss of blood. Although blood pressure and pulse may remain relatively constant for this extended period of time, cardiac output begins to decrease coincidentally with the loss of blood. Hence, under these conditions by monitoring this parameter, loss of blood can be detected much earlier than would otherwise be the case. This permits the surgical team to take prompt remedial action, hopefully forestalling the deterioration in the patient's condition that might have occurred had the loss of blood gone unchecked.

Variations in cardiac output can also be utilized to detect other unwanted changes in the patient's condition such as the onset of schemia of the heart muscle or an anesthetic reaction, again permitting remedial action to be taken before there is any significant deterioration in the patient's condition.

Thermal dilution is one technique which has heretofore been employed to measure cardiac output. In that technique, a thermal dilution catheter carrying a thermistor on its tip is inserted through an incision into the jugular vein and threaded through that vessel and the right side of the patient's heart into the pulmonary artery. A saline solution is then injected through the catheter into the patient's bloodstream, typically at a temperature of 0° C. This solution mixes with the blood flowing through the pulmonary artery, monentarily reducing the temperature detected by the catheter tip thermistor. Standard thermodynamic equations allow the cardiac output to be determined from this drop in temperature and the volume of saline solution which produced the temperature drop.

The thermal dilution technique of measuring cardiac output has the disadvantage that is is highly invasive and therefore potentially capable of damaging the anatomical structures through which the catheter is threaded. In fact, in a small percentage of cases (one to two percent), serious complications result from employment of the thermal dilution technique.

Also, the mere presence of the catheter in the pulmonary artery may result in localized clotting of the blood flowing through that vessel. This can obstruct the orifice through which the saline solution is discharged or produce an insulating layer around the thermistor. In both cases, the results will be highly inaccurate.

Finally, the thermal dilution technique is time consuming as it may take as long as 30 minutes to place the catheter; and only a limited number of measurements per hour of cardiac output can be made. Changes in a patient's condition requiring prompt remedial action may therefore not be detectable by the thermal dilution technique.

Because of the disavantages discussed above, the thermal dilution technique for measuring cardiac output is generally employed only if the patient is undergoing cardiac surgery or is sufficiently ill that surgery poses a risk of cardiac failure.

The Fick method is another technique for measuring cardiac output that has heretofore been employed to some extent. In it, blood samples are taken at two different points in the circulatory system, one just downstream of the patient's aorta and the other in the pulmonary artery. The concentrations of oxygen in these arteries are compared and combined with the amount of carbon dioxide being expelled by the patient to provide a measurement of cardiac output.

The Fick technique has the disadvantage that the measurements are complex and can easily require a day of analysis before cardiac output can be ascertained. This makes the Fick technique useless in the operating theatre where up-to-the-minute information is required to keep the patient in a stable condition.

Of the techniques for measuring cardiac output discussed above, thermal dilution is the most widely employed.

The drawbacks and disadvantages of the above-discussed techniques for measuring cardiac output are eliminated in the method of measuring cardiac output described in U.S. Pat. No. 4,509,526 issued Apr. 9, 1985, to Barnes et al. for METHOD AND SYSTEM FOR NON-INVASIVE ULTRASOUND DOPPLER CARDIAC OUTPUT MEASUREMENT. U.S. Pat. No. 4,509,526 is assigned to the assignee of this application and is hereby incorporated herein by reference.

In the method of measuring a patient's cardiac output disclosed in the Barnes et al. patent, the diameter of the patient's ascending aorta is determined by a pulsed-echo transducer placed on the chest and the systolic velocity of the blood flowing through that artery is determined by insonification of the aorta with an ultrasonic suprasternal notch probe. This second probe makes available Doppler or frequency-shifted electromagnetic signals which are analyzed and converted from the time domain into discrete frequency components by digital fast Fourier transform. The Doppler shifted frequency components of the return signal are converted to velocities, and the latter are employed to calculate a systolic velocity integral.

Multiplying the systolic velocity integral by the cross-sectional aortic area yields beat-by-beat cardiac stroke volumes of the patient; summing the stroke volumes over a predetermined number of consecutive beats and then dividing by the time spanning the predetermined number of beats (in other words, multiplying by the heart rate), yields the patient's cardiac output.

The patented cardiac monitoring apparatus facilitates direct operator interaction with the apparatus over the course of the measurement protocol via a touch sensitive visual display which, inter alia: instructs the operator at each step of the sequence and responds to the election of operator options with failsafe features that guard against the entry of invalid data and otherwise minimize operator error. The operator may interact without extensive training, and the system provides the benefits of microprocessor control including fast data processing without elaborate hardware or software.

Within operational limits, the patented cardiac monitoring system will insist upon the entry of required data, will limit the entry of certain data to values within statistically anticipated ranges, and will assist the operator in optimizing the measurement of variable parameters.

In the novel method and apparatus for monitoring cardiac output we have invented, an ultrasonic esophageal probe is substituted for the suprasternal notch probe used to monitor systolic velocity in the system disclosed in U.S. Pat. No. 4,509,526. This probe monitors the blood flowing through the patient's descending aorta rather than his ascending aorta. This velocity is integrated, and the result is combined with a number representing the area of the patient's ascending aorta to produce a cardiac output value.

This substitution of an ultrasonic esophageal probe for the suprasternal notch probe employed in the patented equipment is important when the system is used during surgery. The preferred type of esophageal probe can be held in position for an extended period of time as may be necessary during major surgery, for example. Furthermore, it does not interfere with the operating field as does a suprasternal notch probe of the type disclosed in U.S. Pat. No. 4,526,509. In addition, unless esophageal surgery is involved, the probe is out of the sterile field, which is an obvious advantage. Furthermore, this probe replaces the esophageal stethoscope which would be employed in any event so that, in effect, another measurement of the patient's condition can be monitored without further invasion of the patient's body.

The blood flowing through a patient's descending aorta is only about 70 percent of that flowing through his ascending aorta, the remainder having been distributed to the patient's subclavian and carotid arteries before the descending aorta is reached. Consequently, in our novel cardiac output measuring apparatus, provision is made for scaling the systolic velocity measured by the esophageal probe by an appropriate conversion factor to the velocity which would have been obtained if the flow in the patient's ascending aorta were instead monitored before the integration is performed.

The proportioning of the blood pumped by a patient's heart between the descending aorta and those other blood vessels discussed above will vary from patient-to-patient. Consequently, we preferably use the suprasternal notch probe technique of measuring systolic velocity disclosed in U.S. Pat. No. 4,526,509 to determine an accurate conversion factor for each patient.

The technique for providing the aortic area value that we employ is also completely different from that disclosed in U.S. Pat. No. 4,526,509. In the patented technique, aortic diameter is measured by insonification of the patient's ascending aorta and converted to aortic area. We, instead, employ a predictively determined value of aortic diameter in our method of and apparatus for determining cardiac output. This has the advantage that it makes the cardiac monitoring equipment we have invented much simpler to use, lighter, and less expensive than that disclosed in U.S. Pat. No. 4,526,509.

The preferred method of predictively determining aortic diameter involves the solution of the following algorithm:

$$AD = 12.6 + [AGE + C_1] - [SEX \times C_2] + [HEIGHT \times C_3] + [WEIGHT \times C_4]$$

where:
AD is aortic diameter in inches,
AGE is the age of the patient in years,
$C_1$ is in the range of 0.046 to 0.066,
SEX is the sex of the patient,
$C_2$ is in the range of 0.7 to 1.3 if the patient is a female and in the range of 1.4 to 2.6 if the patient is a male,
HEIGHT is the height of the patient in inches,
$C_3$ is in the range of 0.012 to 0.022,
WEIGHT is the weight of the patient in pounds, and
$C_4$ is in the range of 0.09 to 0.17.

Preferred values of the constants in the foregoing algorithm are:
$C_1$: 0.066,
$C_2$: 1.0 if the patient is a male and 2.0 if the patient is a female,
$C_3$: 0.17, and
$C_4$: 0.013.

In our novel cardiac monitoring apparatus this equation is solved automatically upon entry of the patient's age, sex, height, and weight.

Like that disclosed in U.S. Pat. No. 4,509,526, the justdescribed method for determining cardiac output disclosed herein is noninvasive and therefore does not subject the patient to the risk of infection or anatomical damage or require surgery as is the case in those cardiac output measuring techniques employing a catheter. And, as in the case of the patented method, that disclosed herein permits cardiac output to be monitored on a continuous, up-to-the-present moment basis.

Yet another advantage of our novel cardiac output monitoring apparatus is that it is capable of, or can easily be programmed to, furnish other valuable information regarding the patient. This includes stroke volume, cardia index, and systemic vascular resistance. Stroke volume was defined above. Cardiac index is cardiac output normalized by dividing that measurement by the patient's body surface area. In essence, this makes the cardiac output measurement patient independent. The person wanting the information can instead simply say that if a patient's cardiac index is above a specified level he is probably doing well and if his cardiac index is below that level there may be a problem. Systemic vascular resistance is blood pressure divided by cardiac output. This parameter can be employed to particular advantage in managing the administration of drugs.

Still other currently and potentially useful measurements that our novel cardiac monitoring apparatus is capable of providing are: peak systolic velocity, acceleration to peak, and delay in onset of systole.

OBJECTS OF THE INVENTION

From the foregoing, it will be apparent to the reader that one important and primary object of the present invention resides in novel, improved methods and apparatus for monitoring the cardiac output of a human patient.

Other also important but more specific objects of the invention reside in the provision of cardiac output monitoring apparatus as aforesaid:

which is versatile;

which is significantly simpler to use and less expensive to produce than the cardiac output monitoring apparatus disclosed in U.S. Pat. No. 4,526,509;

which is much lighter and easier to transport than that described in the aforesaid patent;

which eliminates the need for extensive operator training;

which, in conjunction with the preceding object, employs an ultrasonic esophageal probe to monitor the systolic velocity of the blood flowing through a patient's aorta and provides both a visual signal and an audio signal to facilitate optimum orientation of that probe in the patient's esophagus;

which guards against the entry of invalid data and otherwise minimizes operator error;

which offers rapid processing of data without additional elaborate hardware and software;

which allows cardiac output to be monitored during surgical procedures without invading the sterile operating field or interfering with the surgical team;

which generates a frequency-shifted signal that is representative of the systolic velocity of the blood flowing through a patient's aorta;

which employs an esophageal probe for measuring the systolic velocity of the blood flowing through the patient's descending aorta and in which provision is made for scaling that velocity up to the systolic velocity of the blood flowing through the patient's ascending aorta;

in which, in conjunction with the preceding object, an ultrasonic suprasternal notch probe is provided to make a onetime measurement of systolic velocity from which an appropriate scaling factor can be computed for each patient;

in which provision is made for solving the following algorithm to predictively determine the diameter of a patient's ascending aorta:

$$AD = 12.6 + [AGE \times C_1] - [SEX \times C_2] + [HEIGHT \times C_3] + [WEIGHT \times C_4]$$

where:
AD is aortic diameter in inches,
AGE is the age of the patient in years,
$C_1$ is in the range of 0.046 to 0.066,
SEX is the sex of the patient,
$C_2$ is in the range of 0.7 to 1.3 if the patient is a female and in the range of 1.4 to 2.6 if the patient is a male,
HEIGHT is the height of the patient in inches,
$C_3$ is in the range of 0.012 to 0.022,
WEIGHT is the weight of the patient in pounds, and
$C_1$ is in the range of 0.09 to 0.17;

which can also be employed to provide measurements of other parameters such as stroke volume, cardiac index, peak systolic velocity, acceleration to peak velocity, and delay in onset of systole.

And yet other important but relatively specific objects of our invention are the provision of novel, improved methods of measuring cardiac output:

which are minimally invasive of the patient's body;

which provide a continuous, beat-by-beat measurement of a patint's cardiac output;

in which cardiac output is calculated from the diameter of the patient's ascending aorta and the systolic velocity of the blood flowing through his descending aorta;

in which, in conjunction with the preceding object, a systolic velocity-indicative signal obtained by insonification of a patient's aorta is subjected to a fast Fourier transform analysis to convert it from the time domain to the frequency domain, in which the resulting frequency-based signal components are converted to velocity signals, in which the peak velocity signal is integrated and multiplied by the cross-sectional area of the patient's ascending aorta to yield stroke volume, in which stroke volumes are summed over a selected number of heartbeats, and in which the resulting number is divided by the time spanning the selected number of heartbeats to yield cardiac output;

in which the systolic velocity of the blood flowing through a patient's descending aorta is utilized in monitoring his cardiac output and in which an ultrasonic esophageal probe is employed to measure that parameter;

in which, in conjunction with the last object but one, provision is made for scaling the velocity-indicative signal up to the systolic velocity of the blood flowing through the patient's ascending aorta;

in which, in conjunction with the preceding object, an ultrasonic suprasternal notch probe is provided to make a onetime systolic velocity measurement of the blood flowing through the patient's ascending aorta from which an appropriate scaling factor can be computed;

which makes use of the cross-sectional area of the patient's ascending aorta in computing his cardiac output and in which that area is predictively determined by solving the algorithm:

$$AD = 12.6 + [AGE \times C_1] - [SEX \times C_2] + [HEIGHT \times C_3] + [WEIGHT \times C_4]$$

where:
AD is aortic diameter in inches,
AGE is the age of the patient in years,
$C_1$ is in the range of 0.046 to 0.066,
SEX is the sex of the patient,
$C_2$ is in the range of 0.7 to 1.3 if the patient is a female and in the range of 1.4 to 2.6 if the patient is a male,
HEIGHT is the height of the patient in inches,
$C_3$ is in the range of 0.012 to 0.022,
WEIGHT is the weight of the patient in pounds, and
$C_4$ is in the range of 0.09 to 0.17;

which allow patient-related information to be updated easily and as often as is deemed necessary.

Still other important objects and features and additional advantages of the invention will be apparent to the reader from the foregoing, from the appended claims, and as the ensuing detailed description and discussion proceeds in conjunction with the accompanying drawing.

BRIEF DESCRIPTION OF THE DRAWING

In the drawing:

FIG. 46 is a side view of an ultrasonic, single crystal, continuous wave esophageal probe embodying the principles of the present invention and designed to monitor the systolic velocity of the blood flowing through the descending aorta of a mammalian patient;

FIG. 47 shows the relation between the esophagus and descending aorta of a human patient and the esophageal probe of FIG. 46 in one of the locations it may be caused to assume in that aorta in order to monitor the systolic velocity of the blood flowing therethrough;

FIG. 51 is a bottom view of the probe;

FIG. 52 is a section through the probe taken substantially along line 52—52 of FIG. 51;

FIG. 53 is a section through the probe taken substantially along line 53—53 of FIG. 51;

FIG. 54 is an end view of the probe;

FIG. 55 is a view of an ultrasonic probe as illustrated in FIG. 50 positioned within a supine patient's suprasternal notch by an operator standing behing his head;

DETAILED DESCRIPTION OF THE INVENTION

Figure 1:
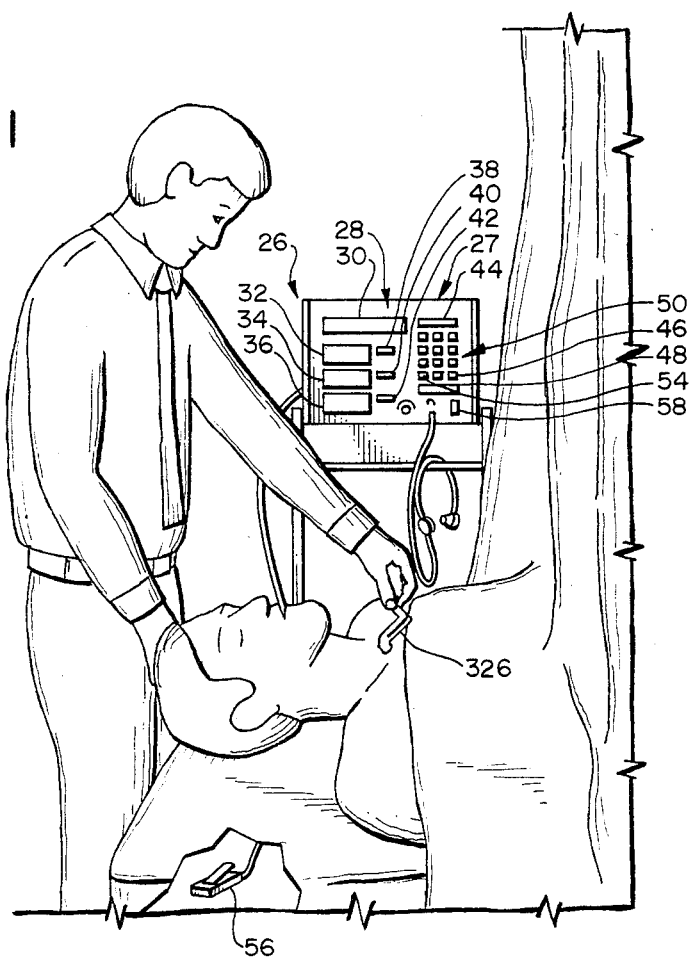
FIG. 1 is a pictorial view of apparatus for monitoring the cardiac output of a human patient which is constructed in accord with, and embodies, the principles of our invention.

As discussed above, the novel cardiac monitoring apparatus disclosed herein is designed to: (1) predictively calculate the area of a patient's ascending aorta from his age, sex, height, and weight; (2) provide a signal indicative of the systolic velocity of the blood flowing through the patient's descending aorta; (3) convert or scale that signal to one representative of the velocity of the blood flowing through the patient's ascending aorta; and (4) compute the patient's cardiac output from the calculated aortic diameter and the scaled up systolic velocity signal.

We also pointed out that the diameter of the patient's ascending aorta is predictively determined by solving the following algorithm:

$$AD = 12.6 + [AGE \times C_1] - [SEX \times C_2] + [HEIGHT \times C_3] + [WEIGHT \times C_4]$$

where:
AD is aortic diameter in inches,
AGE is the age of the patient in years,
$C_1$ is in the range of 0.046 to 0.066,
SEX is the sex of the patient,
$C_2$ is in the range of 0.7 to 1.3 if the patient is a female and in the range of 1.4 to 2.6 if the patient is a male,
HEIGHT is the height of the patient in inches,
$C_3$ is in the range of 0.012 to 0.022,
WEIGHT is the weight of the patient in pounds, and
$C_4$ is in the range of 0.09 to 0.17.

Aortic diameter is converted to aortic area in accord with the well-known formula $$\text{AORTIC DIAMETER} = \frac{\pi AD^2}{4}.$$

The diameters of the ascending aortas of a random sample of 404 patients were actually measured using the ultrasonic imaging technique described in U.S. Pat. No. 4,509,526. These measured diameters were converted to aortic areas and compared with the ascending aortic areas of those 404 patients as predictively determined by the novel technique discussed above. The results of this comparison are shown below:

TABLE 1

| Patient Number | Age (years) | Sex | Height (inches) | Weight (pounds) | Aortic Based on Measured Diameter of Ascending Aorta ($mm^2$) | Aortic Area Based on Predictively Determined Diameter of the Ascending Aorta ($mm^2$) | Percent Error |
|---|---|---|---|---|---|---|---|
| 1 | 38.00 | 2.000 | 61.00 | 99.00 | 28.59 | 35.86 | −57.36 |
| 2 | 28.00 | 2.000 | 60.00 | 158.00 | 28.59 | 35.77 | −56.54 |
| 3 | 60.00 | 1.000 | 70.00 | 129.00 | 35.97 | 44.31 | −51.71 |
| 4 | 21.00 | 2.000 | 64.00 | 168.00 | 29.53 | 36.33 | −51.33 |
| 5 | 47.00 | 2.000 | 66.93 | 149.30 | 32.36 | 39.41 | −48.35 |
| 6 | 18.00 | 2.000 | 67.00 | 182.00 | 30.47 | 37.11 | −48.32 |
| 7 | 21.00 | 2.000 | 66.00 | 176.00 | 30.47 | 37.03 | −47.66 |
| 8 | 33.00 | 1.000 | 69.00 | 163.00 | 34.56 | 41.95 | −47.36 |
| 9 | 54.00 | 2.000 | 62.20 | 151.20 | 32.36 | 38.90 | −44.55 |
| 10 | 39.00 | 2.000 | 62.00 | 174.00 | 31.42 | 37.77 | −44.53 |
| 11 | 29.00 | 2.000 | 64.00 | 133.00 | 30.47 | 36.44 | −42.97 |
| 12 | 56.00 | 2.000 | 64.00 | 214.00 | 35.24 | 40.88 | −42.49 |
| 13 | 38.00 | 2.000 | 66.00 | 165.00 | 32.36 | 38.56 | −41.98 |
| 14 | 22.00 | 2.000 | 61.00 | 138.00 | 29.53 | 35.01 | −40.56 |

TABLE 1-continued

| Patient Number | Age (years) | Sex | Height (inches) | Weight (pounds) | Aortic Based on Measured Diameter of Ascending Aorta (mm²) | Aortic Area Based on Predictively Determined Diameter of the Ascending Aorta (mm²) | Percent Error |
|---|---|---|---|---|---|---|---|
| 15 | 65.00 | 1.000 | 73.00 | 200.00 | 39.74 | 47.08 | −40.35 |
| 16 | 37.00 | 2.000 | 64.17 | 117.90 | 31.42 | 37.00 | −38.71 |
| 17 | 37.00 | 2.000 | 64.00 | 118.00 | 31.42 | 36.96 | −38.37 |
| 18 | 62.00 | 2.000 | 60.00 | 150.00 | 33.30 | 39.11 | −37.93 |
| 19 | 43.00 | 2.000 | 62.00 | 162.00 | 32.36 | 37.93 | −37.44 |
| 20 | 25.00 | 2.000 | 64.00 | 110.00 | 30.47 | 35.55 | −36.13 |
| 21 | 24.00 | 2.000 | 66.00 | 140.00 | 31.42 | 36.60 | −35.75 |
| 22 | 26.00 | 1.000 | 69.00 | 150.00 | 35.19 | 40.96 | −35.53 |
| 23 | 29.00 | 2.000 | 61.00 | 171.00 | 31.42 | 36.41 | −34.30 |
| 24 | 32.00 | 2.000 | 66.00 | 142.00 | 32.36 | 37.47 | −34.08 |
| 25 | 22.00 | 2.000 | 66.00 | 191.00 | 32.36 | 37.44 | −33.87 |
| 26 | 28.00 | 2.000 | 61.00 | 119.00 | 30.47 | 35.24 | −33.74 |
| 27 | 30.00 | 2.000 | 69.00 | 215.00 | 34.24 | 39.56 | −33.48 |
| 28 | 30.00 | 2.000 | 68.90 | 216.10 | 34.24 | 39.56 | −33.43 |
| 29 | 53.00 | 2.000 | 63.00 | 123.00 | 33.30 | 38.44 | −33.23 |
| 30 | 32.00 | 2.000 | 59.00 | 120.00 | 30.47 | 35.14 | −32.94 |
| 31 | 34.00 | 2.000 | 67.00 | 208.00 | 34.24 | 39.29 | −32.31 |
| 32 | 43.00 | 1.000 | 72.05 | 236.60 | 39.74 | 45.30 | −29.95 |
| 33 | 32.00 | 2.000 | 63.00 | 152.00 | 32.36 | 36.87 | −29.80 |
| 34 | 50.00 | 2.000 | 68.11 | 195.10 | 35.97 | 40.98 | −29.77 |
| 35 | 33.00 | 2.000 | 65.00 | 116.00 | 32.36 | 36.77 | −29.13 |
| 36 | 57.00 | 1.000 | 72.05 | 210.30 | 40.68 | 46.21 | −29.01 |
| 37 | 61.00 | 1.000 | 68.00 | 181.00 | 39.74 | 44.93 | −27.84 |
| 38 | 44.00 | 1.000 | 72.00 | 213.00 | 39.74 | 44.91 | −27.72 |
| 39 | 38.00 | 2.000 | 58.00 | 119.00 | 31.42 | 35.46 | −27.43 |
| 40 | 23.00 | 2.000 | 67.00 | 231.00 | 34.24 | 38.63 | −27.26 |
| 41 | 38.00 | 1.000 | 72.05 | 185.80 | 38.80 | 43.75 | −27.16 |
| 42 | 25.00 | 2.000 | 67.00 | 165.00 | 33.30 | 37.49 | −26.72 |
| 43 | 34.00 | 2.000 | 63.00 | 172.00 | 33.30 | 37.48 | −26.68 |
| 44 | 24.00 | 2.000 | 66.00 | 127.00 | 32.36 | 36.34 | −26.11 |
| 45 | 31.00 | 2.000 | 72.83 | 299.60 | 37.86 | 42.43 | −25.60 |
| 46 | 22.00 | 2.000 | 64.00 | 107.00 | 31.42 | 35.18 | −25.43 |
| 47 | 31.00 | 2.000 | 64.00 | 110.00 | 32.36 | 36.17 | −24.97 |
| 48 | 22.00 | 2.000 | 67.00 | 216.00 | 34.24 | 38.22 | −24.57 |
| 49 | 20.00 | 2.000 | 61.00 | 150.00 | 31.42 | 35.05 | −24.47 |
| 50 | 57.00 | 2.000 | 64.17 | 168.40 | 35.97 | 40.09 | −24.24 |
| 51 | 22.00 | 2.000 | 62.00 | 123.00 | 31.42 | 34.97 | −23.93 |
| 52 | 47.00 | 2.000 | 62.00 | 99.00 | 33.30 | 37.06 | −23.85 |
| 53 | 32.00 | 2.000 | 67.00 | 160.00 | 34.24 | 38.11 | −23.83 |
| 54 | 47.00 | 1.000 | 68.00 | 214.00 | 39.74 | 44.17 | −23.51 |
| 55 | 46.00 | 1.000 | 68.90 | 195.30 | 39.74 | 43.92 | −22.15 |
| 56 | 37.00 | 2.000 | 66.00 | 133.00 | 34.24 | 37.80 | −21.85 |
| 57 | 27.00 | 2.000 | 61.81 | 130.10 | 32.36 | 35.58 | −20.92 |
| 58 | 54.00 | 1.000 | 64.17 | 154.10 | 38.80 | 42.63 | −20.74 |
| 59 | 33.00 | 2.000 | 64.00 | 120.00 | 33.30 | 36.58 | −20.69 |
| 60 | 21.00 | 2.000 | 67.00 | 141.00 | 33.30 | 36.58 | −20.69 |
| 61 | 71.00 | 1.000 | 71.00 | 180.00 | 42.57 | 46.75 | −20.62 |
| 62 | 31.00 | 2.000 | 62.00 | 153.00 | 33.30 | 36.51 | −20.23 |
| 63 | 20.00 | 2.000 | 63.00 | 143.00 | 32.36 | 35.45 | −19.99 |
| 64 | 54.00 | 2.000 | 72.83 | 186.70 | 38.80 | 42.49 | −19.93 |
| 65 | 20.00 | 2.000 | 62.00 | 103.00 | 31.42 | 34.36 | −19.61 |
| 66 | 27.00 | 2.000 | 62.00 | 118.00 | 32.36 | 35.39 | −19.59 |
| 67 | 27.00 | 2.000 | 62.00 | 118.00 | 32.36 | 35.39 | −19.59 |
| 68 | 31.00 | 2.000 | 66.00 | 195.00 | 35.19 | 38.45 | −19.41 |
| 69 | 30.00 | 2.000 | 63.00 | 135.00 | 33.30 | 36.31 | −18.90 |
| 70 | 29.00 | 1.000 | 70.08 | 236.60 | 39.74 | 43.33 | −18.88 |
| 71 | 24.00 | 2.000 | 63.00 | 165.00 | 33.30 | 36.31 | −18.87 |
| 72 | 30.00 | 1.000 | 69.00 | 240.00 | 39.74 | 43.21 | −18.24 |
| 73 | 35.00 | 2.000 | 61.00 | 130.00 | 33.30 | 36.19 | −18.09 |
| 74 | 30.00 | 2.000 | 56.00 | 120.00 | 31.42 | 34.12 | −17.97 |
| 75 | 26.00 | 2.000 | 61.81 | 113.10 | 32.36 | 35.13 | −17.88 |
| 76 | 21.00 | 2.000 | 64.00 | 159.00 | 33.30 | 36.14 | −17.81 |
| 77 | 28.00 | 2.000 | 65.00 | 160.00 | 34.24 | 37.16 | −17.73 |
| 78 | 25.00 | 2.000 | 62.99 | 201.30 | 34.24 | 37.15 | −17.69 |
| 79 | 45.00 | 2.000 | 65.00 | 124.00 | 35.19 | 38.17 | −17.69 |
| 80 | 26.00 | 2.000 | 70.00 | 194.00 | 35.97 | 38.99 | −17.49 |
| 81 | 57.00 | 1.000 | 70.08 | 182.30 | 41.63 | 45.11 | −17.43 |
| 82 | 19.00 | 2.000 | 65.00 | 153.00 | 33.30 | 36.08 | −17.42 |
| 83 | 29.00 | 2.000 | 66.00 | 138.00 | 34.24 | 37.08 | −17.24 |
| 84 | 34.00 | 2.000 | 62.00 | 115.00 | 33.30 | 36.05 | −17.17 |
| 85 | 28.00 | 2.000 | 65.00 | 150.00 | 34.24 | 36.95 | −16.44 |
| 86 | 26.00 | 2.000 | 62.00 | 100.00 | 32.36 | 36.95 | −16.43 |
| 87 | 26.00 | 2.000 | 62.00 | 100.00 | 32.36 | 34.92 | −16.43 |
| 88 | 58.00 | 1.000 | 68.00 | 145.00 | 40.68 | 43.89 | −16.38 |
| 89 | 31.00 | 2.000 | 59.00 | 163.00 | 33.30 | 35.91 | −16.29 |
| 90 | 52.00 | 1.000 | 66.93 | 187.40 | 40.68 | 43.85 | −16.17 |
| 91 | 40.00 | 1.000 | 72.00 | 181.00 | 40.68 | 43.85 | −16.15 |
| 92 | 46.00 | 2.000 | 68.11 | 254.60 | 38.80 | 41.78 | −15.97 |

TABLE 1-continued

| Patient Number | Age (years) | Sex | Height (inches) | Weight (pounds) | Aortic Based on Measured Diameter of Ascending Aorta (mm$^2$) | Aortic Area Based on Predictively Determined Diameter of the Ascending Aorta (mm$^2$) | Percent Error |
|---|---|---|---|---|---|---|---|
| 93 | 30.00 | 1.000 | 70.08 | 155.40 | 38.80 | 41.78 | −15.94 |
| 94 | 28.00 | 2.000 | 66.14 | 128.10 | 34.24 | 36.81 | −15.55 |
| 95 | 24.00 | 2.000 | 65.00 | 211.00 | 35.19 | 37.79 | −15.32 |
| 96 | 28.00 | 2.000 | 66.00 | 128.00 | 34.24 | 36.77 | −15.30 |
| 97 | 30.00 | 2.000 | 66.54 | 156.10 | 35.19 | 37.69 | −14.77 |
| 98 | 46.00 | 1.000 | 67.00 | 154.00 | 39.74 | 42.57 | −14.73 |
| 99 | 50.00 | 1.000 | 70.00 | 192.00 | 41.63 | 44.56 | −14.61 |
| 100 | 61.00 | 1.000 | 70.87 | 173.10 | 42.57 | 45.54 | −14.46 |
| 101 | 37.00 | 2.000 | 66.00 | 150.00 | 35.66 | 38.15 | −14.46 |
| 102 | 19.00 | 2.000 | 65.00 | 129.00 | 33.30 | 35.59 | −14.25 |
| 103 | 33.00 | 1.000 | 70.08 | 173.30 | 39.74 | 42.45 | −14.10 |
| 104 | 59.00 | 1.000 | 70.87 | 179.50 | 42.57 | 45.47 | −14.08 |
| 105 | 60.00 | 1.000 | 68.90 | 198.40 | 42.57 | 45.53 | −13.89 |
| 106 | 30.00 | 2.000 | 66.00 | 156.00 | 35.19 | 37.55 | −13.88 |
| 107 | 46.00 | 2.000 | 64.96 | 226.40 | 37.86 | 40.36 | −13.65 |
| 108 | 25.00 | 2.000 | 60.00 | 160.00 | 33.30 | 35.50 | −13.65 |
| 109 | 28.00 | 2.000 | 70.08 | 200.00 | 36.91 | 39.34 | −13.57 |
| 110 | 31.00 | 2.000 | 63.00 | 138.00 | 34.24 | 36.48 | −13.47 |
| 111 | 28.00 | 2.000 | 70.00 | 200.00 | 36.91 | 39.32 | −13.45 |
| 112 | 41.00 | 2.000 | 75.20 | 210.50 | 39.74 | 42.27 | −13.14 |
| 113 | 30.00 | 1.000 | 66.14 | 180.30 | 38.80 | 41.23 | −12.90 |
| 114 | 27.00 | 2.000 | 65.00 | 127.00 | 34.24 | 36.38 | −12.85 |
| 115 | 26.00 | 2.000 | 64.00 | 144.00 | 34.24 | 36.35 | −12.70 |
| 116 | 26.00 | 2.000 | 66.54 | 158.10 | 35.19 | 37.32 | −12.51 |
| 117 | 58.00 | 2.000 | 66.00 | 141.00 | 37.86 | 40.13 | −12.36 |
| 118 | 35.00 | 2.000 | 64.17 | 142.20 | 35.19 | 37.29 | −12.32 |
| 119 | 60.00 | 1.000 | 67.00 | 159.00 | 41.63 | 44.11 | −12.30 |
| 120 | 37.00 | 2.000 | 62.99 | 234.60 | 36.91 | 39.07 | −12.01 |
| 121 | 34.00 | 2.000 | 63.00 | 160.00 | 35.19 | 37.24 | −11.99 |
| 122 | 26.00 | 2.000 | 66.00 | 158.00 | 35.19 | 37.18 | −11.64 |
| 123 | 31.00 | 2.000 | 64.00 | 110.00 | 34.24 | 36.17 | −11.59 |
| 124 | 60.00 | 2.000 | 62.20 | 124.30 | 36.91 | 38.97 | −11.46 |
| 125 | 31.00 | 2.000 | 64.17 | 104.90 | 34.24 | 36.12 | −11.24 |
| 126 | 29.00 | 2.000 | 70.00 | 176.00 | 36.91 | 38.93 | −11.23 |
| 127 | 52.00 | 1.000 | 72.05 | 208.30 | 43.35 | 45.65 | −10.89 |
| 128 | 47.00 | 1.000 | 70.00 | 220.00 | 42.57 | 44.83 | −10.89 |
| 129 | 51.00 | 2.000 | 66.00 | 163.00 | 37.86 | 39.86 | −10.84 |
| 130 | 57.00 | 1.000 | 68.90 | 183.40 | 42.57 | 44.81 | −10.82 |
| 131 | 31.00 | 2.000 | 62.00 | 178.00 | 35.19 | 37.03 | −10.73 |
| 132 | 49.00 | 1.000 | 70.00 | 154.00 | 41.63 | 43.68 | −10.13 |
| 133 | 47.00 | 1.000 | 70.87 | 240.50 | 43.35 | 45.48 | −10.04 |
| 134 | 53.00 | 2.000 | 62.20 | 147.30 | 36.91 | 38.72 | −10.02 |
| 135 | 30.00 | 2.000 | 67.00 | 149.00 | 35.97 | 37.67 | −9.695 |
| 136 | 37.00 | 2.000 | 64.00 | 200.00 | 36.91 | 38.63 | −9.523 |
| 137 | 16.00 | 2.000 | 63.00 | 182.00 | 34.24 | 35.83 | −9.482 |
| 138 | 14.00 | 2.000 | 64.00 | 130.00 | 33.30 | 34.83 | −9.394 |
| 139 | 48.00 | 1.000 | 75.98 | 257.90 | 45.24 | 47.32 | −9.392 |
| 140 | 28.00 | 2.000 | 66.00 | 128.00 | 35.19 | 36.77 | −9.208 |
| 141 | 26.00 | 2.000 | 67.00 | 165.00 | 35.97 | 37.59 | −9.200 |
| 142 | 61.00 | 1.000 | 71.00 | 157.00 | 43.35 | 45.25 | −8.942 |
| 143 | 37.00 | 1.000 | 70.08 | 200.80 | 41.63 | 43.43 | −8.833 |
| 144 | 34.00 | 1.000 | 68.90 | 181.40 | 40.68 | 42.40 | −8.626 |
| 145 | 60.00 | 1.000 | 68.90 | 185.20 | 43.35 | 45.16 | −8.497 |
| 146 | 34.00 | 2.000 | 64.00 | 118.00 | 35.19 | 36.65 | −8.471 |
| 147 | 27.00 | 2.000 | 64.00 | 105.00 | 34.24 | 35.66 | −8.437 |
| 148 | 60.00 | 1.000 | 70.08 | 168.40 | 43.35 | 45.13 | −8.378 |
| 149 | 37.00 | 2.000 | 62.00 | 125.00 | 35.19 | 36.56 | −7.964 |
| 150 | 26.00 | 2.000 | 64.17 | 103.00 | 34.24 | 35.56 | −7.840 |
| 151 | 23.00 | 2.000 | 67.00 | 128.00 | 35.19 | 36.52 | −7.750 |
| 152 | 23.00 | 2.000 | 66.93 | 128.10 | 35.19 | 36.51 | −7.648 |
| 153 | 41.00 | 2.000 | 64.00 | 162.00 | 36.91 | 38.27 | −7.466 |
| 154 | 28.00 | 2.000 | 63.00 | 105.00 | 34.24 | 35.49 | −7.430 |
| 155 | 24.00 | 2.000 | 67.00 | 159.00 | 35.97 | 37.26 | −7.298 |
| 156 | 38.00 | 2.000 | 68.00 | 218.00 | 38.80 | 40.18 | −7.241 |
| 157 | 71.00 | 1.000 | 67.00 | 141.00 | 43.35 | 44.88 | −7.155 |
| 158 | 24.00 | 2.000 | 61.00 | 147.00 | 34.24 | 35.40 | −6.875 |
| 159 | 34.00 | 1.000 | 74.02 | 192.20 | 42.57 | 44.00 | −6.838 |
| 160 | 56.00 | 1.000 | 68.11 | 154.30 | 42.57 | 43.90 | −6.369 |
| 161 | 33.00 | 2.000 | 65.00 | 132.00 | 35.97 | 37.10 | −6.364 |
| 162 | 33.00 | 2.000 | 65.00 | 132.00 | 35.97 | 37.10 | −6.364 |
| 163 | 58.00 | 2.000 | 62.20 | 185.00 | 38.80 | 40.01 | −6.317 |
| 164 | 33.00 | 2.000 | 64.96 | 132.10 | 35.97 | 37.09 | −6.309 |
| 165 | 26.00 | 2.000 | 63.00 | 190.00 | 35.97 | 37.02 | −5.940 |
| 166 | 23.00 | 2.000 | 69.00 | 173.00 | 36.91 | 37.98 | −5.871 |
| 167 | 30.00 | 2.000 | 62.00 | 95.00 | 34.24 | 35.23 | −5.817 |
| 168 | 26.00 | 2.000 | 63.00 | 102.00 | 34.24 | 35.23 | −5.817 |
| 169 | 26.00 | 2.000 | 62.99 | 102.10 | 34.24 | 35.22 | −5.813 |
| 170 | 30.00 | 2.000 | 64.00 | 115.00 | 35.19 | 36.17 | −5.686 |

TABLE 1-continued

| Patient Number | Age (years) | Sex | Height (inches) | Weight (pounds) | Aortic Based on Measured Diameter of Ascending Aorta (mm$^2$) | Aortic Area Based on Predictively Determined Diameter of the Ascending Aorta (mm$^2$) | Percent Error |
|---|---|---|---|---|---|---|---|
| 171 | 30.00 | 2.000 | 64.00 | 115.00 | 35.19 | 36.17 | −5.686 |
| 172 | 68.00 | 1.000 | 69.00 | 161.00 | 44.30 | 45.52 | −5.582 |
| 173 | 30.00 | 2.000 | 61.81 | 95.02 | 34.24 | 35.17 | −5.514 |
| 174 | 26.00 | 2.000 | 62.00 | 110.00 | 34.24 | 35.12 | −5.184 |
| 175 | 17.00 | 2.000 | 70.00 | 229.00 | 37.86 | 38.78 | −4.926 |
| 176 | 28.00 | 1.000 | 72.83 | 217.40 | 42.57 | 43.58 | −4.797 |
| 177 | 20.00 | 2.000 | 65.00 | 144.00 | 35.19 | 36.00 | −4.702 |
| 178 | 31.00 | 2.000 | 64.00 | 186.00 | 36.91 | 37.73 | −4.454 |
| 179 | 29.00 | 2.000 | 63.00 | 120.00 | 35.19 | 35.90 | −4.114 |
| 180 | 29.00 | 2.000 | 62.99 | 119.90 | 35.19 | 35.90 | −4.094 |
| 181 | 25.00 | 2.000 | 62.00 | 153.00 | 35.19 | 35.90 | −4.075 |
| 182 | 26.00 | 2.000 | 63.00 | 220.00 | 36.91 | 37.64 | −3.960 |
| 183 | 35.00 | 2.000 | 65.00 | 147.00 | 36.91 | 37.61 | −3.813 |
| 184 | 27.00 | 2.000 | 63.00 | 125.00 | 35.19 | 35.80 | −3.513 |
| 185 | 65.00 | 1.000 | 75.00 | 215.00 | 47.12 | 47.93 | −3.429 |
| 186 | 25.00 | 2.000 | 65.00 | 146.00 | 35.97 | 36.56 | −3.299 |
| 187 | 44.00 | 1.000 | 73.00 | 205.00 | 44.30 | 45.02 | −3.285 |
| 188 | 17.00 | 2.000 | 62.00 | 136.00 | 34.24 | 34.72 | −2.825 |
| 189 | 42.00 | 2.000 | 64.96 | 156.10 | 37.86 | 38.89 | −2.818 |
| 190 | 42.00 | 2.000 | 62.99 | 129.20 | 36.91 | 37.43 | −2.806 |
| 191 | 52.00 | 1.000 | 68.11 | 220.50 | 44.30 | 44.84 | −2.483 |
| 192 | 17.00 | 2.000 | 64.00 | 152.00 | 35.19 | 35.59 | −2.304 |
| 193 | 53.00 | 1.000 | 68.90 | 156.30 | 43.35 | 43.85 | −2.285 |
| 194 | 39.00 | 2.000 | 60.00 | 131.00 | 35.97 | 36.35 | −2.121 |
| 195 | 16.00 | 2.000 | 67.00 | 154.00 | 35.97 | 36.33 | −2.027 |
| 196 | 41.00 | 1.000 | 70.87 | 187.40 | 43.35 | 43.77 | −1.951 |
| 197 | 26.00 | 2.000 | 68.00 | 181.00 | 37.86 | 38.19 | −1.748 |
| 198 | 52.00 | 2.000 | 64.96 | 275.60 | 41.63 | 41.98 | −1.711 |
| 199 | 24.00 | 2.000 | 67.00 | 203.00 | 37.86 | 38.16 | −1.612 |
| 200 | 27.00 | 2.000 | 64.00 | 180.00 | 36.91 | 37.19 | −1.513 |
| 201 | 27.00 | 2.000 | 64.00 | 180.00 | 36.91 | 37.19 | −1.513 |
| 202 | 28.00 | 2.000 | 66.00 | 148.00 | 36.91 | 37.18 | −1.442 |
| 203 | 30.00 | 2.000 | 59.00 | 144.00 | 35.19 | 35.42 | −1.334 |
| 204 | 30.00 | 1.000 | 68.00 | 189.00 | 41.63 | 41.90 | −1.334 |
| 205 | 18.00 | 2.000 | 65.70 | 152.00 | 35.97 | 36.15 | −.9929 |
| 206 | 35.00 | 1.000 | 72.05 | 191.40 | 43.35 | 43.56 | −.9312 |
| 207 | 43.00 | 2.000 | 56.00 | 152.00 | 35.97 | 36.12 | −.8060 |
| 208 | 31.00 | 2.000 | 65.00 | 140.00 | 36.91 | 37.06 | −.7699 |
| 209 | 55.00 | 1.000 | 72.05 | 227.50 | 46.18 | 46.36 | −.7565 |
| 210 | 29.00 | 2.000 | 62.00 | 143.00 | 35.97 | 36.10 | −.7367 |
| 211 | 31.00 | 2.000 | 61.00 | 107.00 | 35.19 | 35.30 | −.6763 |
| 212 | 23.00 | 2.000 | 67.00 | 152.00 | 36.91 | 37.01 | −.5468 |
| 213 | 32.00 | 2.000 | 70.47 | 153.00 | 38.80 | 38.90 | −.5064 |
| 214 | 23.00 | 2.000 | 61.00 | 145.00 | 35.19 | 35.26 | −.4045 |
| 215 | 45.00 | 2.000 | 64.96 | 297.60 | 41.00 | 41.71 | −.4036 |
| 216 | 26.00 | 2.000 | 65.00 | 115.00 | 35.97 | 36.03 | −.3223 |
| 217 | 20.00 | 2.000 | 66.00 | 178.00 | 36.91 | 36.97 | −.2929 |
| 218 | 29.00 | 2.000 | 62.00 | 138.00 | 35.97 | 36.00 | −.1671 |
| 219 | 51.00 | 2.000 | 61.02 | 132.10 | 37.86 | 37.88 | −.1494 |
| 220 | 32.00 | 2.000 | 70.00 | 153.00 | 38.80 | 38.77 | .1490 |
| 221 | 32.00 | 2.000 | 70.00 | 153.00 | 38.80 | 38.77 | .1490 |
| 222 | 35.00 | 1.000 | 75.00 | 187.00 | 44.30 | 44.26 | .1610 |
| 223 | 31.00 | 2.000 | 68.00 | 138.00 | 37.86 | 37.82 | .1812 |
| 224 | 60.00 | 1.000 | 68.11 | 196.40 | 45.24 | 45.18 | .2769 |
| 225 | 24.00 | 2.000 | 66.00 | 242.00 | 38.80 | 38.69 | .5681 |
| 226 | 58.00 | 1.000 | 70.00 | 178.00 | 45.24 | 45.10 | .6050 |
| 227 | 17.00 | 2.000 | 67.00 | 170.00 | 36.91 | 36.76 | .8091 |
| 228 | 54.00 | 2.000 | 64.96 | 147.70 | 39.74 | 38.39 | .8445 |
| 229 | 61.00 | 2.000 | 63.00 | 137.00 | 39.74 | 39.55 | .9698 |
| 230 | 29.00 | 2.000 | 66.00 | 120.00 | 36.91 | 36.71 | 1.103 |
| 231 | 55.00 | 2.000 | 62.99 | 119.70 | 38.80 | 38.57 | 1.155 |
| 232 | 41.00 | 1.000 | 71.00 | 198.00 | 44.30 | 44.03 | 1.210 |
| 233 | 23.00 | 2.000 | 63.00 | 142.00 | 35.97 | 35.73 | 1.316 |
| 234 | 30.00 | 2.000 | 64.00 | 139.00 | 36.91 | 36.66 | 1.354 |
| 235 | 37.00 | 1.000 | 67.00 | 183.00 | 42.57 | 42.23 | 1.573 |
| 236 | 56.00 | 1.000 | 75.98 | 235.50 | 48.07 | 47.68 | 1.599 |
| 237 | 22.00 | 2.000 | 63.00 | 143.00 | 35.97 | 35.65 | 1.772 |
| 238 | 43.00 | 1.000 | 67.32 | 181.40 | 43.35 | 42.91 | 2.057 |
| 239 | 32.00 | 2.000 | 63.00 | 135.00 | 36.91 | 36.52 | 2.131 |
| 240 | 54.00 | 1.000 | 68.11 | 203.50 | 45.24 | 44.70 | 2.359 |
| 241 | 35.00 | 1.000 | 72.05 | 200.40 | 44.30 | 43.74 | 2.496 |
| 242 | 29.00 | 2.000 | 63.00 | 101.00 | 35.97 | 35.51 | 2.526 |
| 243 | 21.00 | 2.000 | 68.00 | 210.00 | 38.80 | 38.26 | 2.742 |
| 244 | 31.00 | 2.000 | 61.00 | 115.00 | 35.97 | 35.47 | 2.778 |
| 245 | 22.00 | 2.000 | 64.17 | 115.10 | 35.97 | 35.40 | 3.173 |
| 246 | 20.00 | 2.000 | 63.00 | 140.00 | 35.97 | 35.38 | 3.240 |
| 247 | 50.00 | 2.000 | 66.00 | 176.00 | 40.68 | 40.02 | 3.242 |
| 248 | 27.00 | 2.000 | 65.00 | 120.00 | 36.91 | 36.23 | 3.647 |

TABLE 1-continued

| Patient Number | Age (years) | Sex | Height (inches) | Weight (pounds) | Aortic Based on Measured Diameter of Ascending Aorta (mm²) | Aortic Area Based on Predictively Determined Diameter of the Ascending Aorta (mm²) | Percent Error |
|---|---|---|---|---|---|---|---|
| 249 | 35.00 | 2.000 | 60.00 | 100.00 | 35.97 | 35.30 | 3.672 |
| 250 | 30.00 | 2.000 | 64.17 | 115.10 | 36.91 | 36.22 | 3.721 |
| 251 | 35.00 | 2.000 | 59.84 | 100.10 | 35.97 | 35.26 | 3.893 |
| 252 | 22.00 | 2.000 | 61.00 | 112.00 | 35.19 | 34.48 | 3.976 |
| 253 | 30.00 | 2.000 | 64.00 | 115.00 | 36.91 | 36.17 | 3.977 |
| 254 | 16.00 | 2.000 | 60.00 | 110.00 | 34.24 | 33.55 | 4.003 |
| 255 | 28.00 | 2.000 | 66.00 | 143.00 | 37.86 | 37.08 | 4.076 |
| 256 | 28.00 | 2.000 | 66.00 | 143.00 | 37.86 | 37.08 | 4.076 |
| 257 | 50.00 | 1.000 | 64.96 | 155.40 | 43.35 | 42.46 | 4.082 |
| 258 | 27.00 | 2.000 | 62.00 | 110.00 | 35.97 | 35.22 | 4.118 |
| 259 | 27.00 | 2.000 | 62.00 | 110.00 | 35.97 | 35.22 | 4.118 |
| 260 | 23.00 | 2.000 | 62.00 | 130.00 | 35.97 | 35.22 | 4.137 |
| 261 | 48.00 | 2.000 | 66.14 | 172.80 | 40.68 | 39.79 | 4.363 |
| 262 | 27.00 | 2.000 | 61.81 | 110.00 | 35.97 | 35.17 | 4.394 |
| 263 | 59.00 | 1.000 | 68.11 | 198.40 | 46.18 | 45.11 | 4.570 |
| 264 | 28.00 | 2.000 | 66.54 | 130.10 | 37.86 | 36.96 | 4.697 |
| 265 | 40.00 | 1.000 | 75.20 | 199.30 | 46.18 | 45.08 | 4.711 |
| 266 | 23.00 | 2.000 | 60.00 | 113.00 | 35.19 | 34.33 | 4.785 |
| 267 | 15.00 | 2.000 | 62.00 | 126.00 | 35.19 | 34.31 | 4.899 |
| 268 | 20.00 | 2.000 | 63.00 | 170.00 | 36.91 | 36.00 | 4.905 |
| 269 | 36.00 | 2.000 | 67.00 | 216.00 | 40.68 | 39.66 | 4.956 |
| 270 | 24.00 | 2.000 | 64.00 | 181.00 | 37.86 | 36.90 | 4.972 |
| 271 | 40.00 | 2.000 | 63.00 | 157.00 | 38.80 | 37.79 | 5.119 |
| 272 | 21.00 | 2.000 | 62.00 | 221.00 | 37.86 | 36.87 | 5.124 |
| 273 | 60.00 | 1.000 | 68.11 | 184.50 | 46.18 | 44.93 | 5.334 |
| 274 | 42.00 | 2.000 | 68.90 | 200.40 | 41.63 | 40.47 | 5.465 |
| 275 | 54.00 | 1.000 | 72.05 | 205.50 | 47.12 | 45.80 | 5.532 |
| 276 | 39.00 | 1.000 | 68.11 | 198.40 | 44.30 | 43.05 | 5.538 |
| 277 | 28.00 | 2.000 | 63.00 | 257.00 | 39.74 | 38.60 | 5.661 |
| 278 | 59.00 | 1.000 | 70.08 | 291.70 | 49.01 | 47.55 | 5.866 |
| 279 | 38.00 | 1.000 | 70.08 | 173.30 | 44.30 | 42.97 | 5.920 |
| 280 | 25.00 | 1.000 | 72.00 | 212.00 | 44.30 | 42.93 | 6.057 |
| 281 | 27.00 | 1.000 | 72.00 | 154.00 | 43.35 | 41.95 | 6.352 |
| 282 | 59.00 | 2.000 | 60.00 | 177.00 | 40.68 | 39.35 | 6.438 |
| 283 | 61.00 | 1.000 | 68.00 | 168.00 | 46.18 | 44.67 | 6.445 |
| 284 | 47.00 | 2.000 | 66.14 | 243.60 | 42.57 | 41.13 | 6.646 |
| 285 | 53.00 | 1.000 | 70.87 | 212.50 | 47.12 | 45.53 | 6.669 |
| 286 | 30.00 | 2.000 | 65.00 | 164.00 | 38.80 | 37.44 | 6.866 |
| 287 | 68.00 | 2.000 | 64.00 | 162.00 | 42.57 | 41.05 | 7.009 |
| 288 | 26.00 | 2.000 | 68.00 | 186.00 | 39.74 | 38.29 | 7.180 |
| 289 | 46.00 | 1.000 | 71.00 | 104.00 | 44.30 | 42.62 | 7.420 |
| 290 | 28.00 | 1.000 | 70.87 | 240.50 | 45.24 | 43.52 | 7.450 |
| 291 | 33.00 | 2.000 | 60.00 | 120.00 | 36.91 | 35.51 | 7.474 |
| 292 | 36.00 | 1.000 | 66.93 | 161.40 | 43.35 | 41.67 | 7.625 |
| 293 | 46.00 | 1.000 | 71.00 | 234.00 | 47.12 | 45.28 | 7.677 |
| 294 | 18.00 | 2.000 | 70.00 | 150.00 | 38.80 | 37.27 | 7.747 |
| 295 | 49.00 | 2.000 | 64.17 | 201.50 | 41.63 | 39.95 | 7.912 |
| 296 | 19.00 | 2.000 | 60.00 | 104.00 | 35.19 | 33.74 | 8.063 |
| 297 | 31.00 | 2.000 | 62.00 | 142.00 | 37.86 | 36.29 | 8.107 |
| 298 | 17.00 | 2.000 | 58.00 | 139.00 | 35.19 | 33.71 | 8.220 |
| 299 | 76.00 | 1.000 | 70.00 | 133.00 | 48.07 | 46.04 | 8.265 |
| 300 | 31.00 | 2.000 | 62.00 | 140.00 | 37.86 | 36.25 | 8.314 |
| 301 | 56.00 | 1.000 | 70.87 | 173.30 | 47.12 | 45.03 | 8.680 |
| 302 | 32.00 | 2.000 | 65.00 | 135.00 | 38.80 | 37.06 | 8.779 |
| 303 | 32.00 | 2.000 | 64.96 | 134.90 | 38.80 | 37.04 | 8.840 |
| 304 | 24.00 | 2.000 | 63.00 | 112.00 | 36.91 | 35.22 | 8.948 |
| 305 | 48.00 | 1.000 | 68.90 | 189.40 | 46.18 | 44.01 | 9.195 |
| 306 | 27.00 | 2.000 | 63.00 | 181.00 | 38.80 | 36.94 | 9.336 |
| 307 | 48.00 | 1.000 | 73.00 | 177.00 | 47.12 | 44.86 | 9.385 |
| 308 | 45.00 | 2.000 | 65.00 | 151.00 | 40.68 | 38.72 | 9.405 |
| 309 | 17.00 | 2.000 | 65.00 | 115.00 | 36.91 | 35.10 | 9.577 |
| 310 | 27.00 | 2.000 | 62.00 | 146.00 | 37.86 | 35.96 | 9.774 |
| 311 | 31.00 | 2.000 | 72.00 | 336.00 | 45.24 | 42.95 | 9.881 |
| 312 | 25.00 | 2.000 | 66.00 | 145.00 | 38.80 | 36.81 | 9.996 |
| 313 | 44.00 | 1.000 | 66.00 | 106.00 | 43.35 | 41.11 | 10.08 |
| 314 | 60.00 | 2.000 | 64.00 | 125.00 | 41.63 | 39.47 | 10.10 |
| 315 | 16.00 | 2.000 | 67.00 | 174.00 | 38.80 | 36.74 | 10.32 |
| 316 | 18.00 | 2.000 | 67.00 | 163.00 | 38.80 | 36.72 | 10.41 |
| 317 | 32.00 | 2.000 | 65.00 | 118.00 | 38.80 | 36.71 | 10.48 |
| 318 | 23.00 | 2.000 | 69.00 | 240.00 | 41.63 | 39.35 | 10.63 |
| 319 | 59.00 | 2.000 | 64.17 | 200.40 | 43.35 | 40.95 | 10.77 |
| 320 | 42.00 | 1.000 | 73.00 | 230.00 | 48.07 | 45.32 | 11.09 |
| 321 | 58.00 | 2.000 | 59.84 | 135.40 | 40.68 | 38.36 | 11.12 |
| 322 | 22.00 | 2.000 | 67.00 | 135.00 | 38.80 | 36.56 | 11.19 |
| 323 | 22.00 | 2.000 | 66.93 | 134.90 | 38.80 | 36.54 | 11.29 |
| 324 | 33.00 | 2.000 | 64.00 | 203.00 | 40.68 | 38.28 | 11.46 |
| 325 | 51.00 | 1.000 | 59.06 | 139.30 | 43.35 | 40.64 | 12.11 |
| 326 | 33.00 | 2.000 | 60.00 | 118.00 | 37.86 | 35.47 | 12.23 |

TABLE 1-continued

| Patient Number | Age (years) | Sex | Height (inches) | Weight (pounds) | Aortic Based on Measured Diameter of Ascending Aorta (mm$^2$) | Aortic Area Based on Predictively Determined Diameter of the Ascending Aorta (mm$^2$) | Percent Error |
|---|---|---|---|---|---|---|---|
| 327 | 53.00 | 1.000 | 72.00 | 215.00 | 49.01 | 45.88 | 12.36 |
| 328 | 44.00 | 1.000 | 72.00 | 212.00 | 48.07 | 44.89 | 12.77 |
| 329 | 20.00 | 2.000 | 65.00 | 155.00 | 38.80 | 36.23 | 12.81 |
| 330 | 53.00 | 1.000 | 72.83 | 195.10 | 49.01 | 45.70 | 13.05 |
| 331 | 32.00 | 2.000 | 65.00 | 135.00 | 39.74 | 37.06 | 13.05 |
| 332 | 21.00 | 2.000 | 64.00 | 116.00 | 37.86 | 35.27 | 13.22 |
| 333 | 20.00 | 2.000 | 65.00 | 190.00 | 39.74 | 36.94 | 13.58 |
| 334 | 28.00 | 2.000 | 63.00 | 260.00 | 41.63 | 38.66 | 13.74 |
| 335 | 44.00 | 1.000 | 74.02 | 172.00 | 48.07 | 44.62 | 13.84 |
| 336 | 39.00 | 2.000 | 62.00 | 127.00 | 39.74 | 36.81 | 14.22 |
| 337 | 17.00 | 2.000 | 66.00 | 142.00 | 38.80 | 35.92 | 14.28 |
| 338 | 50.00 | 1.000 | 73.00 | 186.00 | 49.01 | 45.25 | 14.76 |
| 339 | 27.00 | 2.000 | 60.00 | 162.00 | 38.80 | 35.75 | 15.11 |
| 340 | 65.00 | 1.000 | 71.00 | 174.00 | 49.95 | 46.01 | 15.16 |
| 341 | 51.00 | 1.000 | 68.90 | 187.00 | 48.07 | 44.27 | 15.18 |
| 342 | 43.00 | 1.000 | 69.00 | 220.00 | 48.07 | 44.15 | 15.65 |
| 343 | 19.00 | 2.000 | 62.00 | 128.00 | 37.86 | 34.77 | 15.66 |
| 344 | 67.00 | 1.000 | 75.00 | 253.00 | 53.56 | 48.91 | 16.63 |
| 345 | 29.00 | 2.000 | 67.00 | 163.00 | 41.63 | 37.86 | 17.29 |
| 346 | 55.00 | 2.000 | 62.99 | 126.30 | 42.57 | 38.71 | 17.31 |
| 347 | 48.00 | 2.000 | 64.17 | 221.60 | 44.30 | 40.25 | 17.43 |
| 348 | 46.00 | 2.000 | 66.14 | 115.30 | 42.57 | 38.40 | 18.61 |
| 349 | 35.00 | 2.000 | 67.00 | 157.00 | 42.57 | 38.35 | 18.82 |
| 350 | 21.00 | 2.000 | 62.00 | 163.00 | 39.74 | 35.69 | 19.36 |
| 351 | 62.00 | 1.000 | 71.00 | 174.00 | 50.89 | 45.70 | 19.36 |
| 352 | 23.00 | 2.000 | 70.00 | 130.00 | 41.63 | 37.37 | 19.40 |
| 353 | 37.00 | 2.000 | 61.02 | 174.40 | 41.63 | 37.31 | 19.68 |
| 354 | 35.00 | 2.000 | 66.00 | 160.00 | 42.57 | 38.15 | 19.70 |
| 355 | 35.00 | 2.000 | 67.00 | 175.00 | 43.35 | 38.72 | 20.23 |
| 356 | 49.00 | 2.000 | 62.99 | 152.30 | 43.35 | 38.62 | 20.64 |
| 357 | 20.00 | 2.000 | 64.00 | 168.00 | 40.68 | 36.23 | 20.72 |
| 358 | 15.00 | 2.000 | 62.00 | 95.00 | 37.86 | 33.68 | 20.85 |
| 359 | 37.00 | 2.000 | 64.00 | 160.00 | 42.57 | 37.81 | 21.09 |
| 360 | 21.00 | 2.000 | 65.00 | 144.00 | 40.68 | 36.11 | 21.23 |
| 361 | 25.00 | 2.000 | 63.00 | 150.00 | 40.68 | 36.10 | 21.25 |
| 362 | 39.00 | 2.000 | 59.84 | 159.60 | 41.63 | 36.89 | 21.45 |
| 363 | 20.00 | 2.000 | 62.00 | 100.00 | 38.80 | 34.30 | 21.86 |
| 364 | 36.00 | 2.000 | 65.00 | 139.00 | 42.57 | 37.55 | 22.19 |
| 365 | 41.00 | 2.000 | 65.00 | 143.00 | 43.35 | 38.15 | 22.58 |
| 366 | 53.00 | 1.000 | 68.11 | 168.40 | 49.95 | 43.88 | 22.82 |
| 367 | 26.00 | 2.000 | 60.00 | 125.00 | 39.74 | 34.89 | 22.93 |
| 368 | 33.00 | 2.000 | 59.06 | 97.66 | 39.74 | 34.80 | 23.34 |
| 369 | 28.00 | 2.000 | 62.00 | 160.00 | 41.63 | 36.35 | 23.75 |
| 370 | 26.00 | 2.000 | 65.00 | 130.00 | 41.63 | 36.34 | 23.80 |
| 371 | 38.00 | 2.000 | 62.99 | 128.30 | 42.57 | 37.00 | 24.46 |
| 372 | 32.00 | 2.000 | 67.32 | 134.90 | 43.35 | 37.68 | 24.46 |
| 373 | 32.00 | 2.000 | 67.00 | 135.00 | 43.35 | 37.59 | 24.80 |
| 374 | 36.00 | 2.000 | 64.00 | 154.00 | 43.35 | 37.59 | 24.83 |
| 375 | 27.00 | 2.000 | 65.00 | 152.00 | 42.57 | 36.89 | 24.91 |
| 376 | 37.00 | 1.000 | 73.00 | 194.00 | 50.89 | 44.07 | 25.01 |
| 377 | 33.00 | 2.000 | 64.17 | 126.10 | 42.57 | 36.76 | 25.45 |
| 378 | 33.00 | 2.000 | 64.00 | 126.00 | 42.57 | 36.71 | 25.65 |
| 379 | 33.00 | 2.000 | 64.00 | 126.00 | 42.57 | 36.71 | 25.65 |
| 380 | 51.00 | 1.000 | 68.00 | 180.00 | 50.89 | 43.88 | 25.65 |
| 381 | 49.00 | 1.000 | 70.08 | 187.40 | 51.68 | 44.39 | 26.23 |
| 382 | 21.00 | 2.000 | 63.00 | 222.00 | 43.35 | 37.16 | 26.52 |
| 383 | 33.00 | 2.000 | 69.00 | 146.00 | 45.24 | 38.46 | 27.72 |
| 384 | 27.00 | 2.000 | 67.00 | 161.00 | 44.30 | 37.61 | 27.91 |
| 385 | 60.00 | 2.000 | 62.20 | 198.40 | 48.07 | 40.49 | 29.05 |
| 386 | 28.00 | 2.000 | 63.00 | 117.00 | 42.57 | 35.74 | 29.52 |
| 387 | 56.00 | 2.000 | 66.14 | 150.80 | 48.07 | 40.16 | 30.19 |
| 388 | 65.00 | 1.000 | 71.00 | 185.00 | 55.45 | 46.24 | 30.47 |
| 389 | 26.00 | 2.000 | 60.00 | 146.00 | 42.57 | 35.32 | 31.17 |
| 390 | 41.00 | 2.000 | 61.00 | 126.00 | 44.30 | 36.72 | 31.27 |
| 391 | 23.00 | 2.000 | 65.00 | 157.00 | 44.30 | 36.58 | 31.81 |
| 392 | 28.00 | 2.000 | 64.00 | 143.00 | 44.30 | 36.54 | 31.96 |
| 393 | 59.00 | 2.000 | 66.93 | 194.40 | 50.89 | 41.57 | 33.27 |
| 394 | 19.00 | 2.000 | 63.00 | 180.00 | 44.30 | 36.10 | 33.59 |
| 395 | 32.00 | 2.000 | 69.00 | 147.00 | 47.12 | 38.38 | 33.67 |
| 396 | 37.00 | 2.000 | 66.93 | 257.90 | 49.95 | 40.60 | 33.92 |
| 397 | 26.00 | 1.000 | 72.00 | 157.00 | 51.68 | 41.91 | 34.23 |
| 398 | 28.00 | 2.000 | 65.00 | 117.00 | 45.24 | 36.28 | 35.70 |
| 399 | 15.00 | 2.000 | 65.00 | 182.00 | 45.24 | 36.27 | 35.74 |
| 400 | 77.00 | 1.000 | 54.00 | 159.00 | 53.56 | 42.37 | 37.44 |
| 401 | 20.00 | 2.000 | 65.00 | 169.00 | 46.18 | 36.51 | 37.48 |
| 402 | 37.00 | 1.000 | 73.00 | 160.00 | 55.45 | 43.38 | 38.80 |
| 403 | 22.00 | 2.000 | 69.00 | 200.00 | 50.89 | 38.43 | 42.98 |

TABLE 1-continued

| Patient Number | Age (years) | Sex | Height (inches) | Weight (pounds) | Aortic Based on Measured Diameter of Ascending Aorta (mm²) | Aortic Area Based on Predictively Determined Diameter of the Ascending Aorta (mm²) | Percent Error |
|---|---|---|---|---|---|---|---|
| 404 | 41.00 | 2.000 | 66.00 | 137.00 | 50.89 | 38.29 | 43.39 |

In the foregoing table, percent error was calculated in accord with the formula:

$$\text{Percent Error} = \frac{\text{Measured Diameter} - \text{Predicted Diameter} \times 100}{\text{Measured Diameter}}$$

We determined that predicted values of aortic diameter would be acceptable to the medical profession if they were within ±20 percent of the measured aortic diameter 75 percent of the time. Errors of the magnitude just discussed are acceptable because it is the change from the baseline measurement of cardiac output that is important in monitoring a patient's condition, not the absolute measurement. Nevertheless, a reasonably accurate, as opposed to arbitrary, baseline measurement is needed to satisfy the desires of the medical profession.

The desired degree of accuracy was closely approached in the test from which the data reported in Table 1 were obtained in that 72 percent of the predictively determined aortic diameters were within 20 percent of the measured aortic diameters.

Insonification of the patient's descending aorta to measure the systolic velocity of the blood flowing through that vessel is accomplished by the use of an esophageal probe.

The preferred esophageal probe 220, illustrated in FIGS. 46-49 of the drawing, consists of an esophageal stethoscope 222 and, mounted on the lower end of the latter, an ultrasonic transducer tip 224 (all references to direction assume that esophageal probe 220 is oriented as shown in FIG. 47).

Esophageal stethoscope 222 is a flexible, hollow tube with acoustical ports 226 in its lower end. An acoustically transparent sleeve 228 is sealed to the tube around ports 226 to keep mucous and other substances in the esophagus from clogging the acoustical ports.

An acoustical coupling 230 is fitted to the upper end of esophageal stethoscope 222. This is employed to connect the esophageal stethoscope to one of conventional character, allowing the physician or other person employing the stethoscope to listen to the patient's breathing, heart sounds, etc. Coupling 230 also houses leads from a thermistor (not shown) in the lower end of the esophageal stethoscope. That thermistor may be provided so that the patient's body temperature can also be monitored as is sometimes advantageous during surgery.

The esophageal probe 220 shown in FIG. 46 also has a flexible, branching tube 232. This contains leads 34 from the transducer crystal or crystals depending on whether a single or double crystal transducer is employed.

Figure 48:
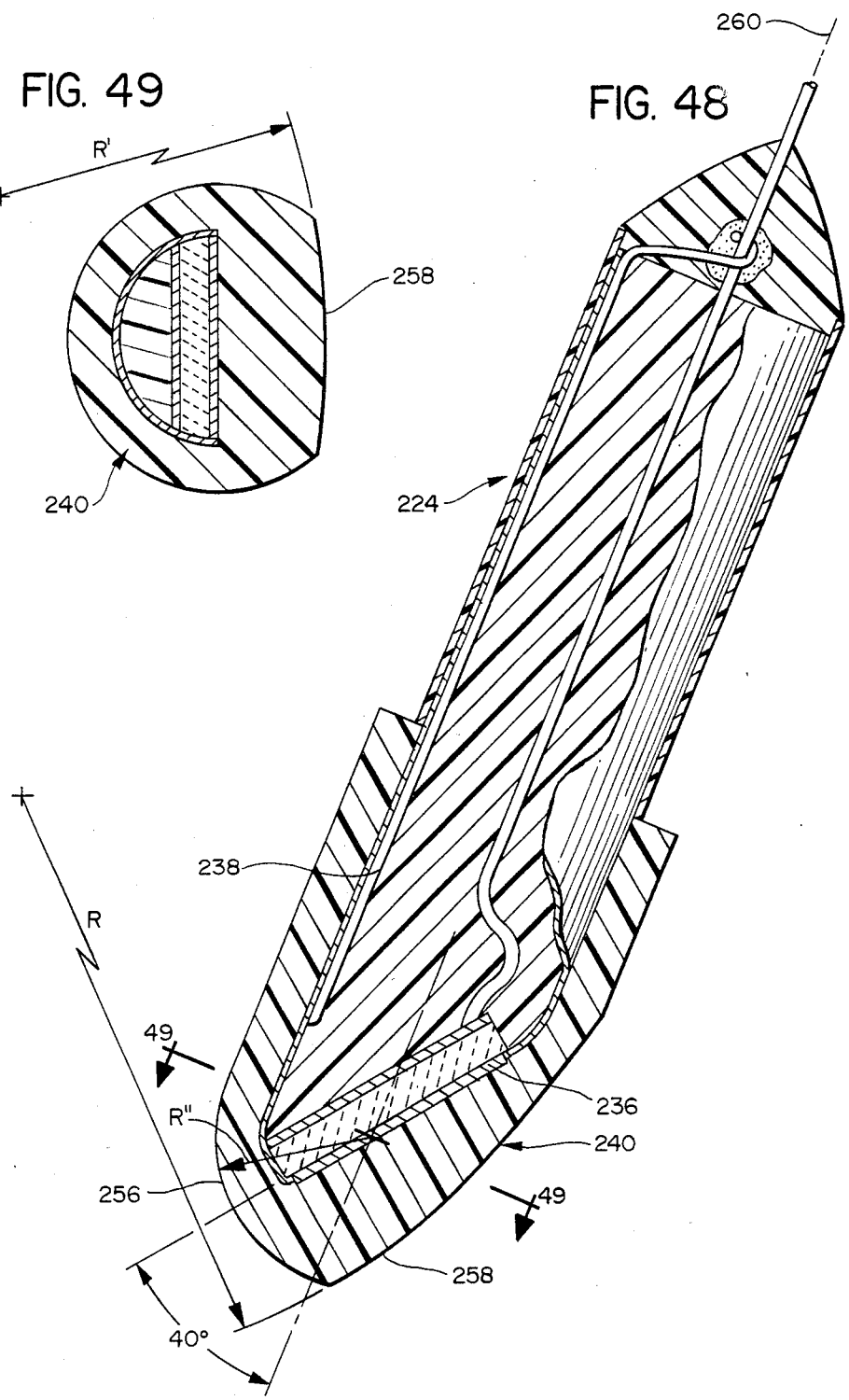
FIG. 48 is a partial section through the esophageal probe illustrated in FIG. 46.

Referring now to FIG. 48, the major components of the esophageal probe's transducer tip 224 include a transducer such as the illustrated conventional, D-shaped dual crystal piezoelectric transducer 236 (or a conventional disc-shaped, single crystal piezoelectric transducer (not shown)); a support 238 for the transducer; and a lens 240.

Of importance, in conjunction with the manufacture of transducer tip 224, is the compound curvature of transducer lens 240. That lens is employed to converge the beam of ultrasonic energy propagated from transducer 236 and to steer that bean at a selected, preferably 45°, angle toward the descending aorta of the patient whose systolic blood velocity is being monitored. The compound curvature of the lens eliminates the air bubble problems that have plagued heretofore proposed esophageal probes by allowing the patient's esophageal wall to collapse tightly around the tip 224 of probe 220. This more than satisfactorily acoustically couples transducer 236 through the mucous in the esophagus to the esophageal wall. Because the esophagus is in intimate contact with the descending aorta over a significant portion of the latter's length, the result is an entirely acceptable acoustic coupling between the transducer and the descending aorta.

Figure 49:
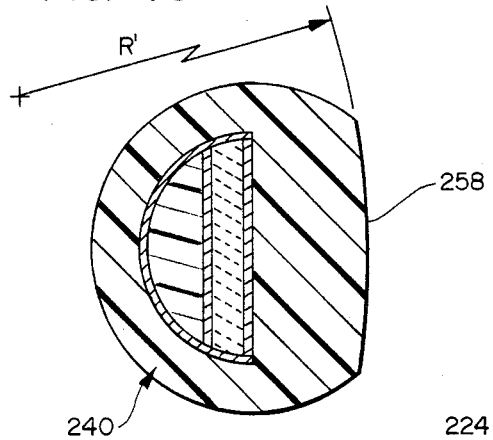
FIG. 49 is a section through FIG. 48 taken substantially along line 49—49 of the latter Figure.

As is best shown in FIGS. 48 and 49, lens 240 has a generally arcuate cross-section and a nose 256 which is similarly configured when viewed in longitudinal section as shown in FIG. 48. That part 258 of the lens which steers the beam of energy emitted from transducer 236 is arcuate in both cross- and longitudinal section.

If the end of the transducer tip were simply cut flat, an air pocket would be created between the tip of the probe and the esophagus when the probe was passed into the latter. As a result, it would not be possible to obtain good acoustical coupling between the transducer and the esophageal wall. As discussed above, the compound curvature and domelike configuration of the transducer lens 240 instead allow the esophageal wall to contract tightly around the lower end of the transducer tip, eliminating any such air pocket and providing the wanted acoustical coupling.

In one exemplary embodiment of the invention, lens 240 is 0.450 inch long and 0.3125 inch in diameter. Radius "R" is 0.75 inch as is radius "R'". Nose radius "R''" is 0.156 inch.

In the transducer tip 224 illustrated in FIG. 48, piezoelectric crystal 236 is mounted at an angle of 40° with respect to the longitudinal centerline 260 of the tip. The compound curvature of lens 240, because of the refraction of the ultrasonic energy in that lens, causes the beam of ultrasonic energy propagated from transducer 236 to be directed at an angle of 45° relative to the descending aorta of the patient whose systolic blood velocity is being monitored.

The esophageal probe 220 just described is introduced into the patient's mouth, typically after he is anesthesized, and passed downwardly through the patient's esophagus until transducer tip 240 is opposite the patient's descending aorta. A thus properly located esophageal probe is illustrated in FIG. 47. In that figure, the patient's esophagus is identified by reference character 262, his descending aorta by reference character 264, the ascending aorta of the patient by reference character 266, and his aortic arch by reference character 268.

As is also shown in FIG. 47, the esophagus collapses tightly around tip 224 of the probe. As discussed above, this furnishes the wanted acoustical coupling from transducer crystal 236 through the esophagus 262 of the patient to his descending aorta 264. The contraction of the esophageal wall stabilizes the transducer over an extended period of time.

As will be apparent from FIG. 47, esophageal probe 220 can readily be rotated in the patient's esophagus 262 after it has been passed down through the esophagus. This allows transducer 224 to be so directed toward descending aorta 264 as to provide optimal coupling between the transducer and the descending aorta of the patient.

In the esophageal probe 220 illustrated in FIGS. 46 and 48, the transducer tip 224 is located immediately adjacent the acoustic ports 226 in esophageal stethoscope 222. This is not critical; and it may indeed prove advantageous to locate the tip as much as one or two inches away from the acoustical ports. This allows stethoscope 222 and transducer 236 to be optimally positioned to pick up heart sounds and to monitor systolic velocity, respectively.

Typically, transducer crystal or crystals 236 will be positioned in the mid to lower thoracic region of the patient. Often, optimal results may be achieved by positioning the transducer opposite the aortic arch of the patient or in the region where the esophagus passes through his diaphragm. The latter location is preferred because the esophagus is necked down as it passes through the diaphragm. This further promotes acoustical coupling between the probe and the esophageal wall.

The return signal from the transducer of the esophageal probe is a Doppler or frequency-shifted signal. To provide a true measurement of cardiac output, that signal must be scaled up so that it represents the systolic velocity of the blood flowing through the patient's ascending aorta. This is accomplished with a suprasternal notch probe, preferably of the character disclosed in U.S. Pat. No. 4,526,509 or of the character illustrated in FIGS. 50 to 55 of the drawing.

The latter, identified by reference character 326, includes a handle 328 and a transducer head 330 integral therewith. Transducer head 330 has a sloping top wall 331 and curved side walls 332 giving the transducer head a generally oval cross-sectional configuration as shown in FIG. 51 and a trapezoidal profile as shown in FIG. 54. The bottom or lower end of the transducer head is essentially flat when viewed from the side; it has a shallow V-configuration when seen from the front (FIG. 54).

In the embodiment of the invention shown in the drawing, the lower end 334 of transducer head 330 extends approximately 0.44" below the bottom side or surface 336 of probe handle 328. This is an important feature of probe 326 as it furnishes sufficient clearance for the operator to wrap his fingers around the handle 328 of probe 326 when the head of the probe is positioned in the patient's suprasternal notch. This facilitates the tactile positioning and manipulation of the probe within the patient's suprasternal notch.

Figure 2:
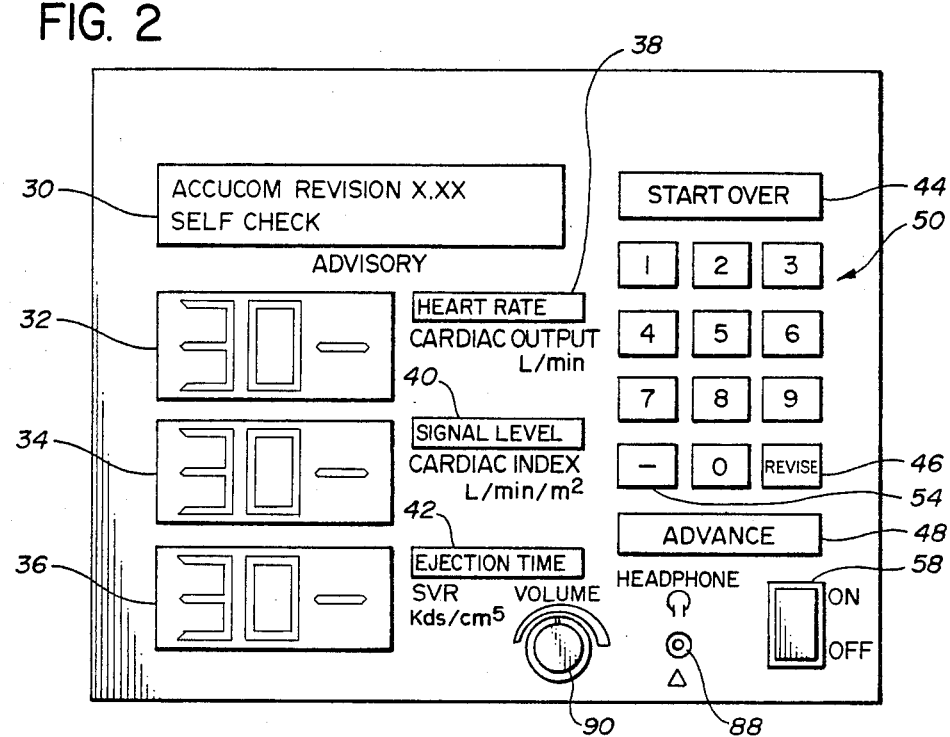
FIGS. 2–43 are illustrations of the visual display of the cardiac output monitoring apparatus shown in FIG. 1; these Figures show the messages that appear as the operator interacts with the cardiac monitoring apparatus in the course of monitoring a patient's cardiac output (or cardiac index or systemic vascular resistance)
Figure 3:
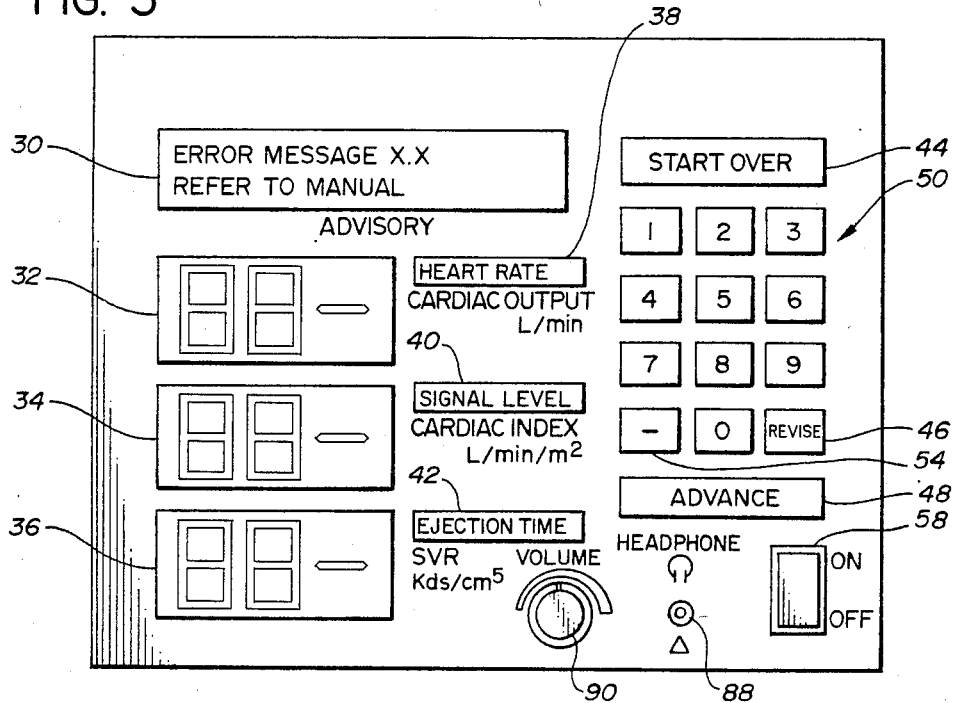

Flat, D-shaped transducers 338 and 340 are flush-mounted in cavities 342 and 344 in the lower end 334 of transducer head 330 with the transducers canted toward a longitudinal plane 346 extending vertically through the transducer head as is shown in FIG. 2. The included angle "A" between the transducers 338 and 340 will typically be approximately 174°.

The illustrated transducers 338 and 340 are of the conventional piezoelectric crystal type; and these will accordingly, not be described further herein. They can be cemented in place by an appropriate adhesive, for example.

Referring now specifically to FIG. 52, ultrasonic energy is propagated from transducer 338 along path 348. This energy, doppler-shifted in frequency, is reflected from the patient's aortic structure and the blood flowing through that vessel back to receptor transducer 340 along path 350.

Transducers 338 and 340 are connected to an external energy source (not shown) through leads 352 incorporated in a conventional insulated cable 354. This cable passes through the head 330 and handle 328 of probe 326 (see FIGS. 52 and 53) and, externally of the probe, terminates in a conventional six-prong connection 356.

As shown in FIG. 52, the path 348 of the propagated ultrasonic energy and the path 350 of the reflected frequency-shifted energy converge in a focal zone 358 which embraces the patient's ascending aorta. In a probe of the character under discussion, this zone should have a focal point which is preferably approximately seven centimeters from the lower end 334 of transducer head 330. This goal can be realized by configuring the lower end of probe 220 that the above-discussed angle A between the two transducers 338 and 340 will be the preferred 174°.

Figure 50:
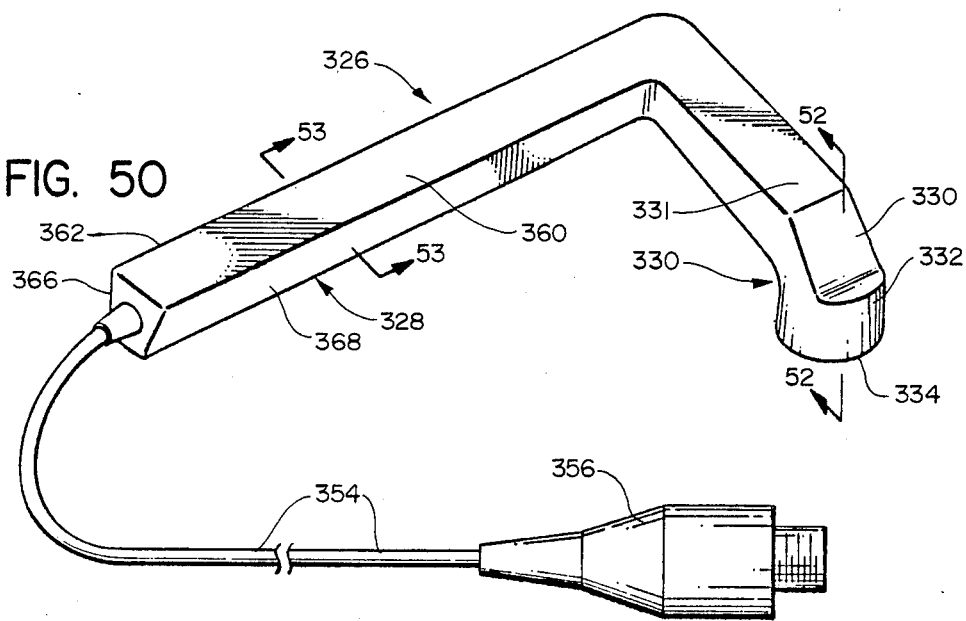
FIG. 50 is a perspective view of an ultrasonic, suprasternal notch probe embodying the principles of the present invention.

Referring now primarily to FIGS. 50 and 51, the handle 328 of probe 326 has a proximate, horizontal portion 360 and, extending at a severe, preferably 90°, angle therefrom, a second, also horizontal, distal portion 362.

As is readily apparent from the drawings, the preferred cross-sectional configuration of handle 328 is one which is essentially approximately rectangular but with the side walls 366 and 368 of the handle's distal portion tapering slightly toward each other from the top toward the bottom of the handle to provide the most secure grasp and optimal operator comfort.

This is not essential, however; and strictly rectangular and other polygonal configurations can be employed, if desired. Also, configurations such as circular may be employed with one or more protruding grips being provided in such cases to furnish a secure operator grip.

These novel ultrasonic probe handle configurations just discussed are an important feature of our invention because, as shown in FIG. 55, they allow the operator to position the transducer head 330 of the probe 326 in the patient's suprasternal notch and to rotate, move rectilinearly, and otherwise manipulate its transducer head 330 with facility and without strain or other discomfort from his position behind a patient's head. These advantages and the minimization of patient discomfort are also promoted by the combined effects of this L-shaped probe handle configuration, the orthogonal relationship among the two sections of the handle and the transducer head, and the curvilinear cross-sectional configuration and trapezoidal profile of the latter.

It will be manifest from the foregoing that accurate positioning of ultrasonic probe 326 is paramount in obtaining data which accurately indicates the diameter of the patient's ascending aorta. In the operating arena, this requires manipulation of transducer head 330 with little or no visual assitance and without discomfort to the patient, goals which are met by probe 326 because of the shape of the transducer head, the multiple graspable surfaces and L-shaped configuration of the probe handle, and the use of rounded edges to avoid discomfort to both the patient and the person manipulating the probe.

In positioning and aligning the transducer head 330 of ultrasonic probe 326 in a patient's suprasternal notch, the anesthesiologist or other person employing the probe reaches past the head of the patient and introduces the transducer head 330 of the probe within the patient's suprasternal notch (see FIG. 55). This maneuver is typically effected while the operator's attention is directed to a visual display of the cardiac output equipment and other monitors (the former assists him in properly positioning the probe). Thereafter, the transducer head may be rotated, shifted rectilinearly, and tilted, again with attention focused on the visual display, until that display shows that the position of the probe has been optimized.

With the operator's fingers and thumb pressed against the distal handle portion 362 of probe 326, a secure grip which optimizes control over these manipulations of the probe with minimal, or even no, view of the patient's suprasternal notch or of transducer head 330 is conveniently available.

The ultrasonic probe 326 illustrated in FIGS. 50-55 and discussed above is configured for use by a right-handed operator positioned behind the head of a supine or reclining patient. An L-shaped, mirror image configuration is provided for left-handed operators. Alternatively, a handle with a T-shaped configuration may be employed so that the probe can be used by either a left-handed or right-handed operator. Details of the manner in which the suprasternal notch probe is employed may be found in the foregoing patent to which the reader may refer if those details are of interest. From the velocity determined from the suprasternal notch and esophageal probe measurements, one can compute a scale or conversion factor which can be applied to the systolic velocity measured by the esophageal probe to scale the latter to a value representing the systolic velocity of the blood flowing through the patient's ascending aorta.

Aortic diameter and the relationship between the systolic velocities of the blood flowing through a patient's ascending aorta and descending aorta are factors which normally do not change appreciably except, perhaps, over extended periods of time, typically several months. Consequently, aortic diameter and the scale factor discussed above normally need be determined only at the start of testing. Nevertheless, as will become apparent hereinafter, our novel cardiac monitoring apparatus is designed so that both of these constants can be easily and quickly recalculated as often as desired.

In the interest of maximizing efficiency and reliability of results, we preferably establish by appropriate software a plurality of signal sampling rates based upon corresponding ranges of statistically anticipated systolic velocities for the patient under examination. High and low threshold values are selected for these separate velocity ranges; systolic velocity is monitored to determine its value within a given one of the ranges as measued with reference to the selected threshold values; and the signal sampling rate is adjusted to that one of the sampling rates corresponding to the systolic velocity.

Our cardiac monitoring apparatus initially processes data at the first sampling rate while monitoring the velocity signal. Upon the occurence of systolic velocities in excess of the high threshold value for the first range, the system automatically adjusts the sampling rate to the second rate for further processing. Monitoring of the velocities continues, now with reference to a high and low threshold value within the second range. Systolic velocities lower than the low threshold cause a downward adjustment to the first sampling rate, while velocities in excess of the high threshold for the second range adjust the sampling rate to the third range. Should the third rate be selected, and subsequent monitoring reveal systolic velocities lower than a low threshold for that range, an adjustment in the sampling rate to the second rate is made. In this manner, processing of data is correlated with the appropriate velocity range, enhancing processing capabilities while simplifying system hardware and software.

The cardiac output is presented on the visual display of the patented equipment during the continuous measurement of systolic velocity and also provides a message to the operator when the signal level is too low, prompting more accurate positioning of the ultrasonic probes.

An audible indication of systolic velocity is also made available to the operator by an audio signal with a frequency directly proportional to velocity.

A conventional frequency spectrum analyzer converts the analog time domain velocity signal appearing at the esophageal probe into its digital frequency domain counterpart at a sampling rate determined by the criteria discussed above and, in more detail, in U.S. Pat. No. 4,526,509. A spectrum analysis is typically completed once every 2.5 to 10 milliseconds, depending upon the sampling rate dictated by the systolic flow velocity of the blood being monitored.

There is a peak frequency in each sampling period. The peak frequencies which are associated with each cardiac cycle (or heartbeat) collectively constitute a velocity profile signal which is accurately indicative of the actual systolic velocity of the patient's aortic blood flow. The velocity profile signal is integrated over the time of the cardiac cycle, producing a systolic flow velocity integral. Stroke volume is computed from the integrated profile and the patient's predictively determined aortic diameter, and his cardiac output is calculated by summing n stroke volumes and dividing the sum by the time span of the n cardiac cycles for which stroke volumes were determined.

Those components of the cardiac monitoring apparatus in which the foregoing frequency analysis and computations are made include both hardware and software. The hardware is shown in FIG. 1 except for the inner components of the monitor. The latter include a Zilog Z8000 series microprocessor system and the hardware illustrated in FIGS. 56-58 of the drawing.

The latter is employed to keep the frequency-shifted return signal from being blanketed by the transmitted signal employed to excite the transducer into an ultrasonic energy emitting mode. The key component in the scheme is a hybrid transformer. That transformer is illustrated in FIGS. 56A and 57 and identified by reference character 370. Hybrid transformers and their mode of operation are described in more detail in HYBRID TRANSFORMERS PROVE VERSATILE IN HIGH-FREQUENCY APPLICATIONS, Gross, T. A. O. Gross & Associates, Lincoln, Mass.

Also shown in FIG. 57 are transmitter 372 and receiver 374 which are employed to excite piezoelectric crystal 236 of probe 220 and to process the reflected, frequency-shifted signal available from that transducer.

Figure 56:
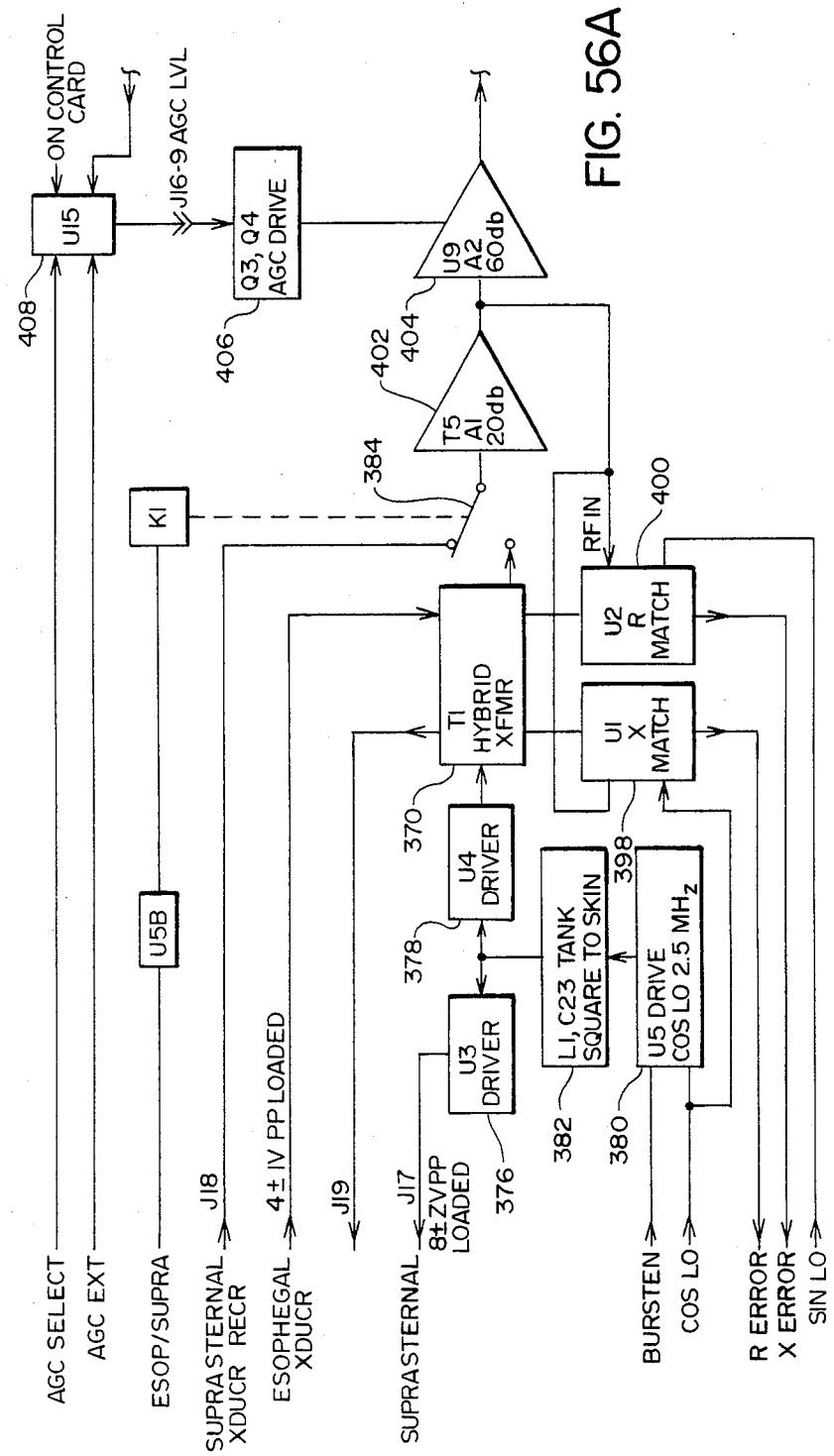
FIG. 56 shows the relationship among FIGS. 56A–56G which, taken together, constitute a block diagram of a transmitter for exciting the transducer of the esophageal probe illustrated in FIGS. 46–49 and a receiver for processing frequency-shifted energy transmitted to it from the transducer of the esophageal probe.
Figure 57:
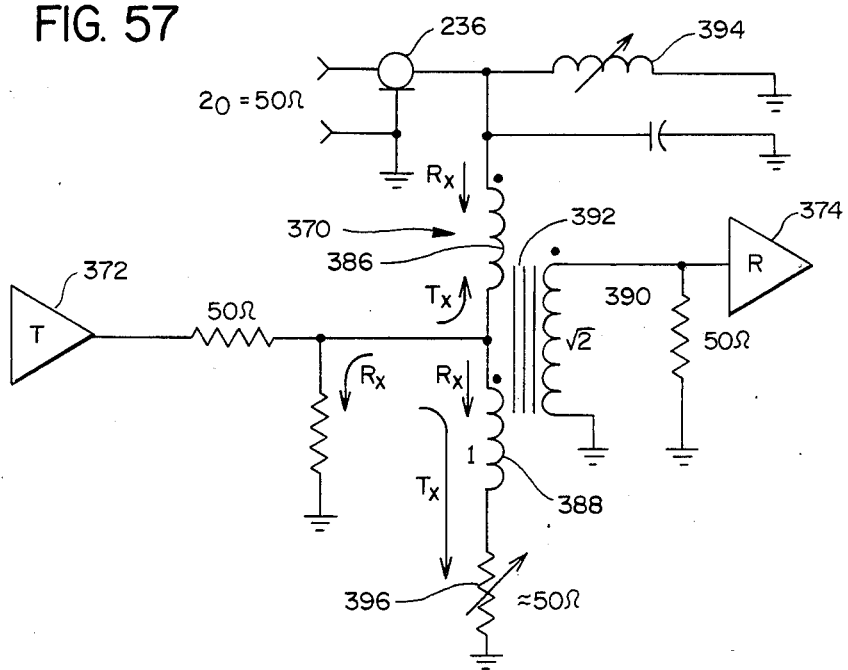
FIG. 57 is a general schematic of the transducer interface circuit employed in the single crystal, continuous wave esophageal probe, the transmitter employed to excite that transducer, the receiver for processing the frequency-shifted electromagnetic energy, and a hybrid transformer employed to keep transmitted energy and/or unwanted reflected energy from blanketing the frequency-shifted signal of interest.

A number of hexagons embracing the letters TP followed by a numeral appear in FIG. 56. These are keyed to the descriptive material in these figures designated OPERATIONAL LEVELS and TEST LEVELS so that, by referring to the latter, one can identify the operational and test level characteristics of transmitter 372 and receiver 374 at each of the several test points.

As best shown in FIG. 56A, transmitter 372 includes drivers 376, 378, and 380 and an LC tank 382. Driver 380 is continuously driven with a 2.5 MHz square wave signal designated COS LO. The tank circuit 382 converts the square wave pulses to a sinusoidal voltage which is amplified by driver 378 and applied to piezoelectric crystal 236 of the esophageal probe 326 to excite that transducer.

As mentioned above, receiver 374 is provided to process the systolic velocity indicative, Doppler-shifted signals detected by transducer 336. It can also be employed to process frequency-shifted signals available from a suprasternal notch probe such as that disclosed in U.S. Pat. No. 4,509,526 or a similarly configured dual crystal transducer configuration.

A two-position switch 384 (see FIG. 56A) allows either the single crystal esophageal probe, dual crystal esophageal probe, or suprasternal notch probe mode of operation to be selected. In the latter two modes of operation, hybrid transformer 370 is bypassed.

The power of the transmitted signal may be as much as 127 to 130 dbm greater than that of the reflected, frequency-shifted signal simultaneously available at transducer 236 in the continuous wave mode of operation for which the single crystal esophageal probe 220 is designed. Because receiver 374 will typically have a dynamic range of only 60 dbm, the transmitted signal would consequently blanket the wanted return signal absent the employment of hybrid transformer 370 to block the transmitted signal from receiver 374.

As discussed above, the suprasternal notch probe is employed in generating a scaling factor. This is used to scale the systolic velocity of the blood flowing through the patient's descending aorta to the systolic velocity of the blood flowing up through his ascending aorta. The latter value is needed to compute the patient's cardiac output by the novel technique disclosed herein.

As shown in FIG. 57, the hybrid transformer includes series-connected primary windings 386 and 388, a secondary winding 390, and magnetic core 392. Coupled to primary windings 386 and 388 are a variable inductance 394 and a dummy load or variable resistance 396.

The variable inductance permits the inductance in windings 386 and 388 to be matched to a particular transducer such as the piezoelectric crystal 236 employed in esophageal probe 220. Consequently, it is not necessary to replace fixed value circuit components every time a new transducer is employed as would be the case absent the variable inductance because a close match between the impedance in the circuitry and in the transducer is required for accurate measurements of systolic velocity.

Variable load 396 permits the impedance in primary transformer windings 386 and 388 to be balanced so that no current will flow through these windings as is shown in FIG. 57. Specifically, transmitter 372 drives through the center of windings 386 and 388 with the current flowing upwardly through winding 386 and downwardly through winding 388 as shown by arrows $T_x$ in FIG. 57. With variable resistance 396 adjusted to match the impedances in windings 386 and 388, the circuit is balanced; there is no flow of current in the primary windings; and no signal is transmitted to receiver 374.

In contrast, the analog frequency-shifted signal detected by transducer 236 flows downwardly through both primary windings 386 and 388 as indicated by arrows $R_x$ in FIG. 57. This generates a signal in secondary winding 390 which is coupled to receiver 374 as is also shown in FIG. 57. Consequently, the systolic velocity indicative signals detected by transducer 336 can reach receiver 374 although the signals simultaneously transmitted by transmitter 372 cannot.

We pointed out briefly above that feedback is employed to continuously adjust variable resistance 396 and thereby provide dynamic balancing of the hybrid transformer primary coils 386 and 388. Also, the characteristics of the signal propagated from the transducer are effected by pressure and temperature, and these parameters constantly vary in a patient's body. The feedback technique we employ also continuously adjusts resistance 396 to compensate for variations in these parameters.

Referring still to FIG. 56A, the active elements of the feedback control are of the phase detector type and are identified by reference characters 398 and 400.

The inputs to the phase detectors in active circuit elements 398 and 400 are signals representing the sums of and differences between the frequency of the signal from the transducer 236 and a reference signal. The outputs from these detectors are designated COS LO and SIN LO. If the the frequency-shifted signal is in phase with the transmitted signal, the signal designated COS LO will be generated in the detector of active circuit element 400 and applied to variable resistance 396 to balance the hybrid transformer primary windings 386 and 388 (the appearance of an in-phase signal means that the impedances in windings 386 and 388 are not balanced). If the transmitted and frequency-shifted signals are out-of-phase, the SIN LO signal will appear and be applied to variable inductance 394 to precision tune the inductance in the primary windings of the hybrid transformer to transducer 236.

The frequency-shifted signals reflected from bones or other large anatomical structures are blocked from receiver 374 because the circuitry shown in FIG. 57 is capable of discriminating between reflected signals of different frequencies. The reflected signals of interest will typically have a frequency ranging from 100 to 10,000 Hz away from the frequency propagated from transducer 236. With signals of this character present, the primary and secondary windings of the hybrid transformer are coupled and the signal transmitted to receiver 374. In contrast, the unwanted signals will typically have much lower frequencies. The detectors in active circuit elements 398 and 400 perceive a slow signal in the same manner as they do a signal originating from transmitter 372, and they balance the impedance in the hybrid transformer primary coils as necessary to cancel the slower moving signal.

The tunable inductance 394 allows transducers and transmitter/receiver systems to be matched automatically in the field, making it possible to supply the esophageal probes and a transmitter/receiver separately. This is an important practical advantage of our invention as it allows the esophageal probes to be disposed of after a small number of uses or even after a single use, if desired, or in the event of a failure, all without the necessity of returning the transmitter/receiver hardware for matching with a new probe.

From hybrid transformer 370, the frequency-shifted signal of interest, typically having frequency components of 2.5 MHz plus 100–1,000 Hz and 2.5 MHz minus 100–10,000 Hz, is amplified in amplifier 402 (see FIG. 56B) after the frequency-shifted velocity indicative return signal is picked off for the detectors in active circuit elements 398 and 400. After amplification, the return signal is transmitted to an integrated circuit 404 which is an automatic gain control and converts the frequency-shifted signal to one or more-or-less constant amplitude.

Automatic gain control 404 is feedback controlled by a controller 406 coupled to switch 408. The latter allows the feedback employed to regulate the automatic gain control to be taken from either receiver 374 or from an external source. The latter might be, for example, a computer supplying a signal such as that designated AGC EXT in FIG. 56A.

From automatic gain control 404, the velocity indicative return signal is amplified in a radio frequency amplifier 409. The amplified signal is transmitted to mixers 410 and 411. The return signal is multiplied by COS in one mixer and by SIN in the other as is conventional in a quadrature circuit. The mixers generate in-phase and quadrature signals identified as I and Q in FIG. 56B.

The next stage in receiver 374 consists of a pair of DC notches 412 and 414 which are passive, high-pass filters. These are followed by integrated track-and-hold circuits 416 and 418 which allow receiver 374 to be employed in a pulse as well as a continuous wave mode of operation. Next in line are two-stage amplifiers—420/422 and 424/426.

After the second stage of amplification, the I and Q channels are split between the receiver circuitry shown in FIGS. 56B–56F and detectors 428 and 430 which generate the feedback signals for automatic gain control 404. The signals from detectors 428 and 430 are converted to DC in rectifiers 432 and 434, and the rectified signals are summed with the gain of the summation signal being increased in amplifier 436. The amplified signal is applied to integrator 438 which is a low-pass filter. Rectification is employed so that the feedback signal available from integrator 438 will represent the amplitude of the frequency-shifted signal made available to receiver 374 from the transducer 336 of the esophageal probe 220.

As is shown in FIG. 56E, and I and Q signals are also applied to buffers 440 and 442. These active circuit elements provide impedance matching of the circuit with automatic gain control feedback detectors 428 and 430.

To filter out any remaining components of the frequency-shifted signal that would have the frequencies associated with reflection of the transducer propagated energy from large anatomical structures such as bones and slow moving structures such as lungs, the signals processed in buffers 440 and 442 are transmitted to high-pass filters 444 and 446. These are conventional integrated circuits designed to filter out low frequencies.

Systems such as those illustrated in FIG. 56 can confuse very high frequency signals with low frequency signals if both arise simultaneously. To eliminate very high frequency components of the I and Q signals, they are processed through low-pass, anti-alias PRF filters 448 and 450. These are also conventional integrated circuits.

The filtered signal components are amplified in amplifiers 452 and 454 and applied to integrated track-and-hold circuits 456 and 458. These conventional circuits hold the analog signal components designated I and Q so that they can be converted to digital signals and processed by the fast Fourier transform technique described in U.S. Pat. No. 4,509,526.

The final active circuit components 460 and 462 illustrated in FIG. 56F are conventional audio drives which provide buffering between the circuit components just described and those (not shown) in which the analog-to-digital conversions of signal components I and Q are performed. These, and the components for converting the return signal appearing at transducer 236 to a visual display of the systolic velocity of the blood flowing through a patient's descending aorta, are not shown in the drawing and will not be discussed herein because they are not part of the present invention and because those system components can be akin to the corresponding circuit elements of the equipment disclosed in U.S. Pat. No. 4,509,526.

As shown in FIG. 56F, the in-phase and quadrature signal components designated I and Q are also picked off between amplifier 452 and track-and-hold circuit 456 and between amplifier 454 and track-and-hold circuit 458. These signal components are combined, and the resulting signal is applied to an attenuator 464 which is conventional and acts as an audio volume control. Volume can be adjusted by a potentiometer 466 available to the operator of the system in which the esophageal probe and transmitter/receiver are incorporated.

From volume control 464, the processed signal indicative of the patient's systolic velocity is applied to a speaker driver 468. This drives a speaker 470 which allows the operator to listen to the blood flowing through the patient's decending aorta. This enables him to optimally position the esophageal probe 220 as he can float the probe downwardly through the patient's esophagus and rotate it, continuing until the loudest sound (indicative of optimum position) is obtained.

Figure 58:
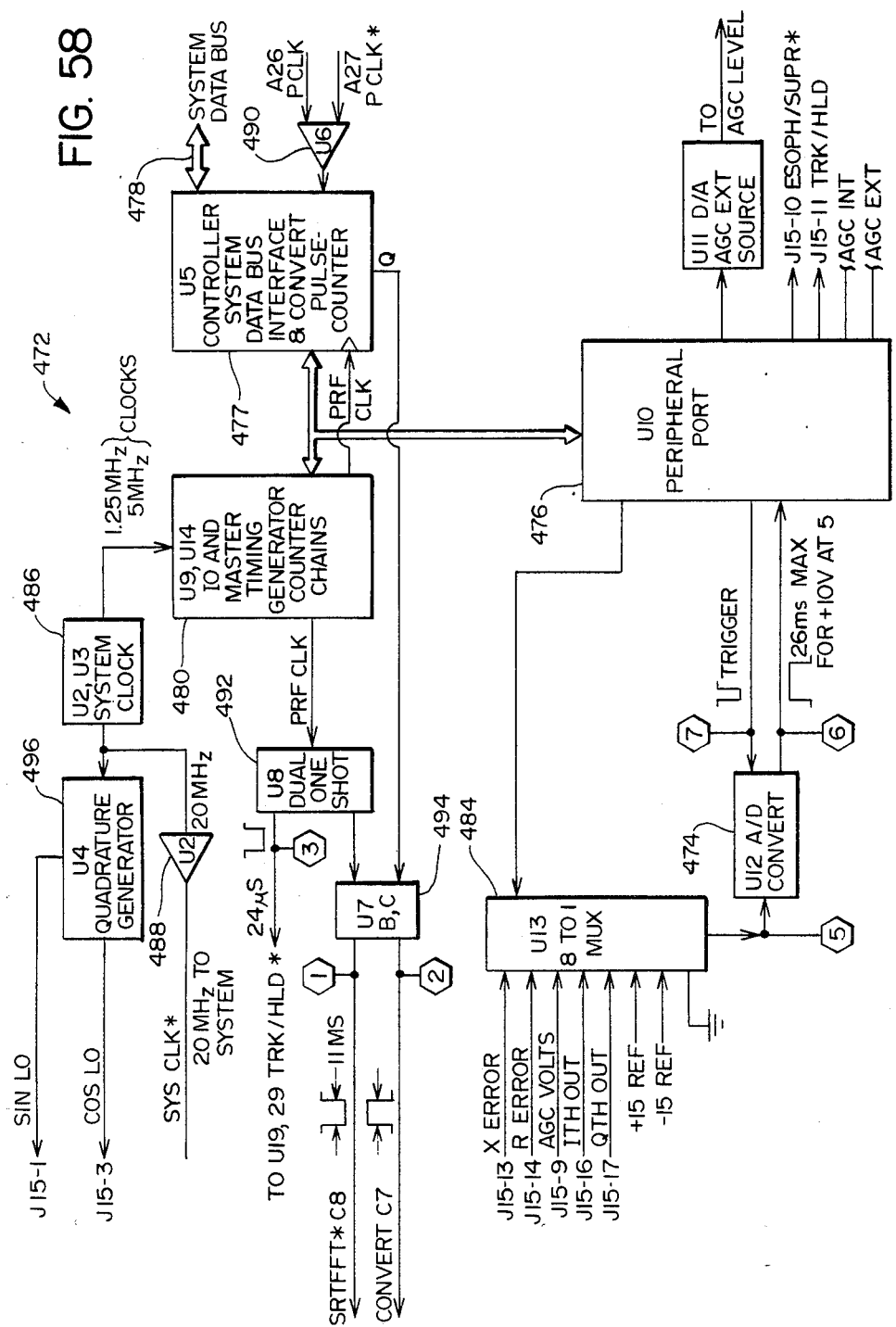
FIG. 58 is a block diagram of an interface which can be employed to couple the signal processing circuitry to a microprocessor or other general purpose computer.

It will be apparent to the reader that the transmitter/receiver system just discussed is intended to be computer controlled. An appropriate interface between the transmitter/receiver hardware and a general purpose computer provided for controlling the operation of that hardware (not shown) is illustrated in FIG. 58 and identified by reference character 472. Among the active circuit devices in interface 472 is an analog-to-digital converter 474. This converter enables the computer to ascertain whether the inductance in the receiver circuitry is properly matched to the transducer 236 in prove 220 and whether the impedances in the primary windings 386 and 388 of hybrid transformer 370 are balanced. It also allows the computer to identify the amount of gain being affected by automatic gain control 404. The signals designated +15 Ref and −15 Ref can also be digitized to ascertain whether the transmitter/receiver system is operating properly.

In addition to the analog-to-digital converter, interface 472 includes a peripheral port 476 and a controller 477. The latter is an integrated circuit that provides an interface between: (a) a system data bus 478 and (b) peripheral port 476 and master timing generator 480.

The master timing generator allows the transmitter/receiver controlling computer to set clock rates which control high-pass wall filters 444 and 446 and anti-aliasing filters 448 and 450 as well as the four track-and-hold circuits 416, 418, 456, and 458.

Figure 56B:
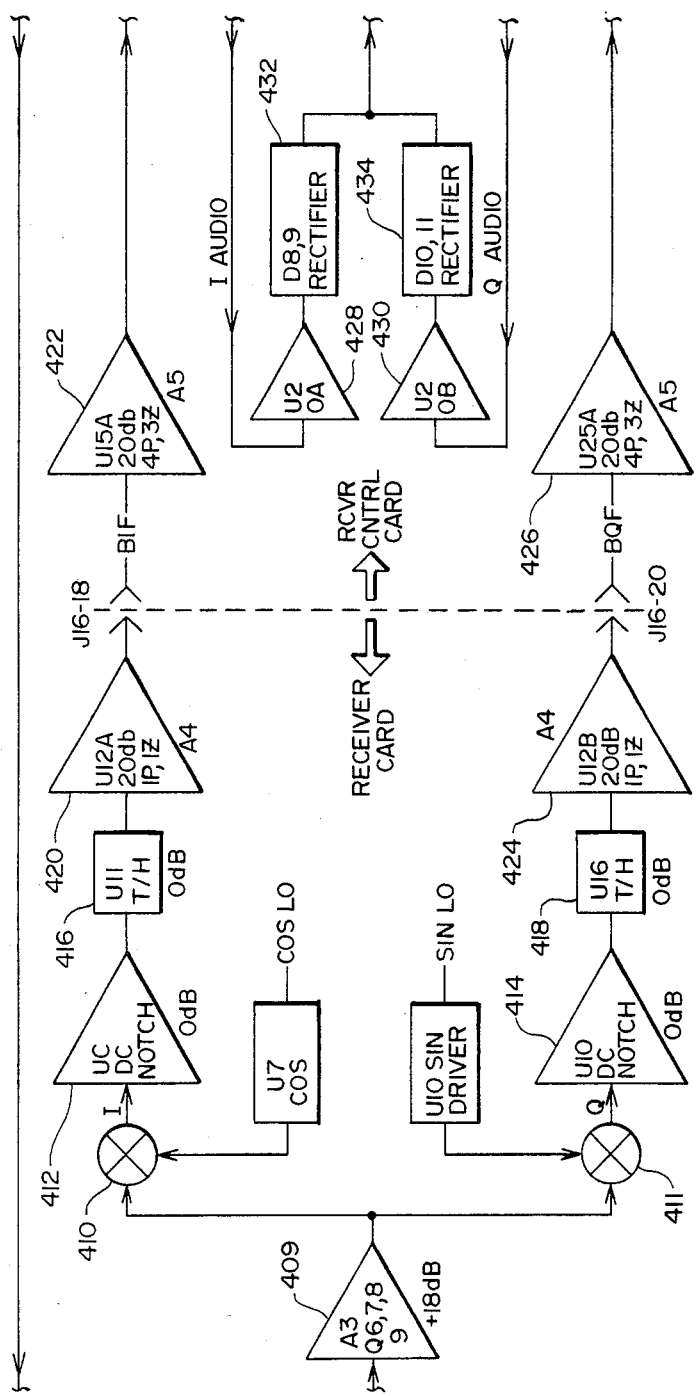
Figure 56D:
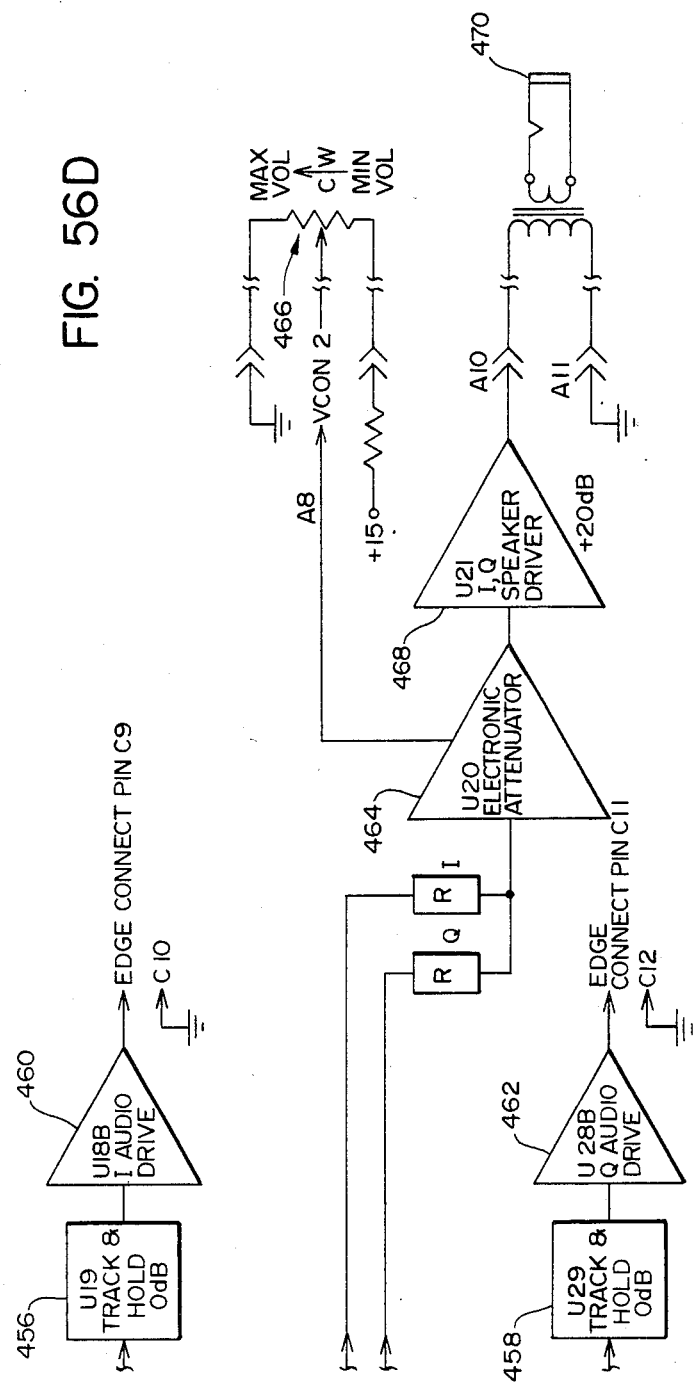

Peripheral port 476 controls various ones of the active circuit elements in the transmitter/receiver system; viz., the switch 384 which determines whether receiver 374 will accept signals from an esophageal or a suprasternal notch probe, the switch 408 shown in FIG. 56B which allows the gain afforded by automatic gain control 404 to be computer controlled, and the several track-and-hold circuits. Peripheral port 476 also controls the operation of an 8:1 multiplexer 484 through which the signals to be analyzed are brought into analog-to-digital converter 474.

Also incorporated in interface 472 is a clock 486 which controls the operation of the transmitter/receiver system. And another active circuit component included in interface 472 is a buffer 488 for the clock pulses.

Circuit element 490 gates clock pulses into the interface controller 477; and circuit elements 492 and 494 are, respectively, a dual one-shot and a flip-flop which provide appropriate signals for controlling the operation of the track-and-hold circuits and electrically interface the transmitter and receiver with the host computer.

Finally, interface 472 includes a quadrature generator 496 which generates the reference signals SIN LO and COS LO discussed above.

The software employed in the novel cardiac monitoring apparatus disclosed herein includes the algorithms employed in performing the fast Fourier transform of the analog systolic flow velocity signal and those used in the various computations identified and discussed above.

We pointed out in the foregoing discussion of our invention that a systolic flow velocity measured by insonification of the patient's ascending aorta with an ultrasonic suprasternal notch probe is employed to generate a scaling factor in our novel cardiac monitoring apparatus. The frequency-shifted signal made available by the suprasternal notch probe is processed in the same manner as the signal generated by the ultrasonic esophageal probe and for the same reasons.

Both stroke volume and cardiac output are measurements that can be employed to advantage in determining a patient's bodily condition. Related, and perhaps equally useful, indicia of a patient's condition are stroke index and cardiac index. As discussed above, cardiac index is cardiac output normalized across the general population by dividing that measurement by the patient's body surface area so that one can make a determination of a patient's condition simply by comparing the patient's cardiac index to a standard.

Stroke index is useful for the same reasons and is determined in an analagous manner; viz., by dividing stroke volume by the patient's body surface area.

Our novel cardiac monitoring apparatus is designed to also make the calculations necessary to determine stroke index and cardiac index.

Another calculation which that apparatus is designed to make is systemic vascular resistance. We pointed out earlier herein that systemic vascular resistance (blood pressure divided by cardiac output) is particularly useful in developing a drug regime for a patient requiring medical intervention.

Referring now to FIG. 1 of the drawing, the hardware of the cardiac monitoring apparatus 26 we have invented more specifically includes ultrasonic esophageal probe 220, the above-mentioned circuitry (transmitter/receiver system and computer interface), suprasternal notch probe 326 as described above, and the microprocessor for computing cardiac output from the systolic velocity monitored by probe 220 and the predictively determined area of the patient's aorta. The transmitter/receiver circuits, the computer interface, and the microprocessor system are housed in cabinet 27 which also includes a touch-sensitive screen 28 with a two-line 20 character per line display 30 labeled ADVISORY, dual-mode LED displays 32, 34, and 36 for values of cardiac output or heart rate, cardiac index or signal level, and SVR (systemic vascular resistance) or injection time.

Heart rate, signal level, and ejection time are displayed during a mode of operation employed in the positioning of ultrasonic esophageal probe 220 and ultrasonic suprasternal notch probe 326; they assist the operator in optimally orienting the probes.

Specifically, the aorta has a different duration of systole or ejection time than other major blood vessels in its vicinity. By observing the EJECTION TIME display, therefore, the operator can ascertain whether the return signal is one reflected from the patient's aorta or from a different blood vessel. The display designated SIGNAL LEVEL is used by repositioning the ultrasonic probe until that probe orientation produces a signal of maximum strength.

LED displays 38, 40, and 42 with the legends HEART RATE, SIGNAL LEVEL, and EJECTION TIME and opposite value-indicating LED's 32, 34, and 36 are backlighted when the monitor is operating in the mode just discussed.

Also appearing on screen 28 of the cardiac monitoring apparatus are touch sensitive areas that furnish START OVER, REVISE, and ADVANCE kets 44, 46, and 48 and a keyboard 50 with keys 1 through 0 and a MINUS key 54.

A final component of cardiac monitoring apparatus 26 is a footswitch 56. The footswitch may be employed by the operator to initiate a number of the steps in the cardiac output measuring protocol. This may be more convenient than employing the touch sensitive screen—for example, when the operator is occupied in positioning ultrasonic probe 326 in the patient's suprasternal notch or in positioning ultrasonic probe 220 in the patient's esophagus.

The operation of the novel cardiac monitor discussed above and illustrated in FIG. 1 will be apparent from the ensuing discussion of FIGS. 2–43. These figures depict the instructions and other messages that appear on the advisory 30 of screen 28 as the operator of the cardiac monitoring apparatus follows the protocol we employ to measure the cardiac output of a patient.

Turning first to FIG. 2, the initial step in this procedure is to press on-off switch 58. That turns on the monitoring apparatus 26 and initiates a self-check of the apparatus. LED displays 32, 34 and 36 are illuminated with the number 30 when the self-check starts. This number decreases at the rate of one digit per second and indicates that the self-check is in progress.

Keyboard 50 ignores all attempts to input data through it while the self-check is in progress.

If a real or suspected fault is detected during the course of the cardiac monitor self-check, the LED displays will stop counting; and advisory 30 will continue to ignore inputs.

The illustrated error message is not displayed if the cardiac monitor 26 has not been correctly set up; i.e., if the ultrasonic esophageal probe 220 has not been connected. Instead, display 30 will display the message NO ESOPH PROBE DETECTED, ADVANCE IF OK, or FIX.

Figure 4:
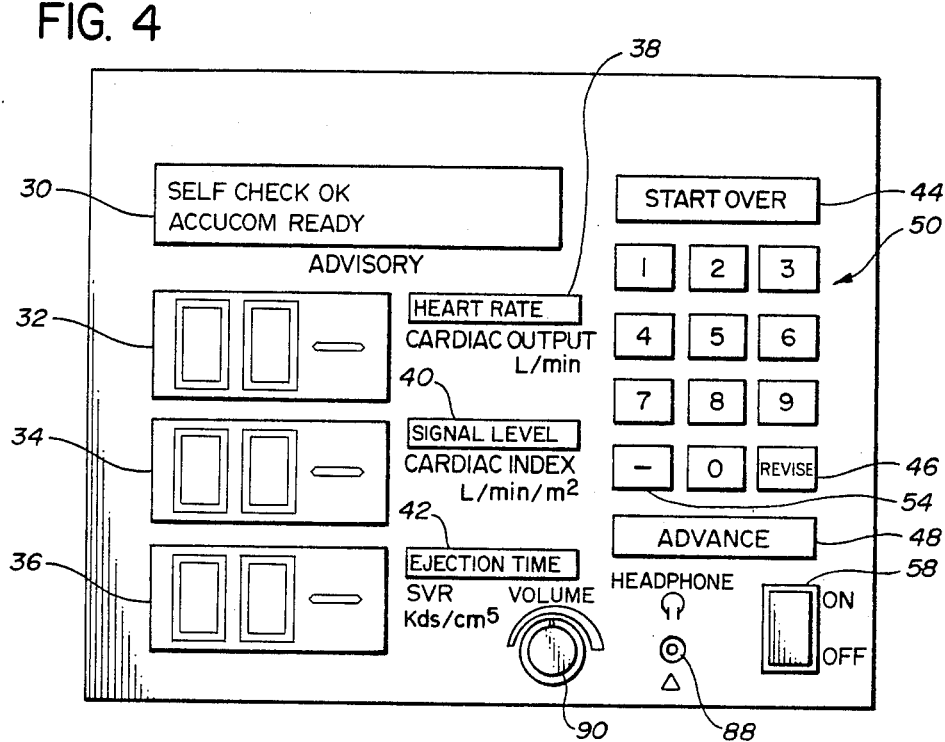
Figure 5:
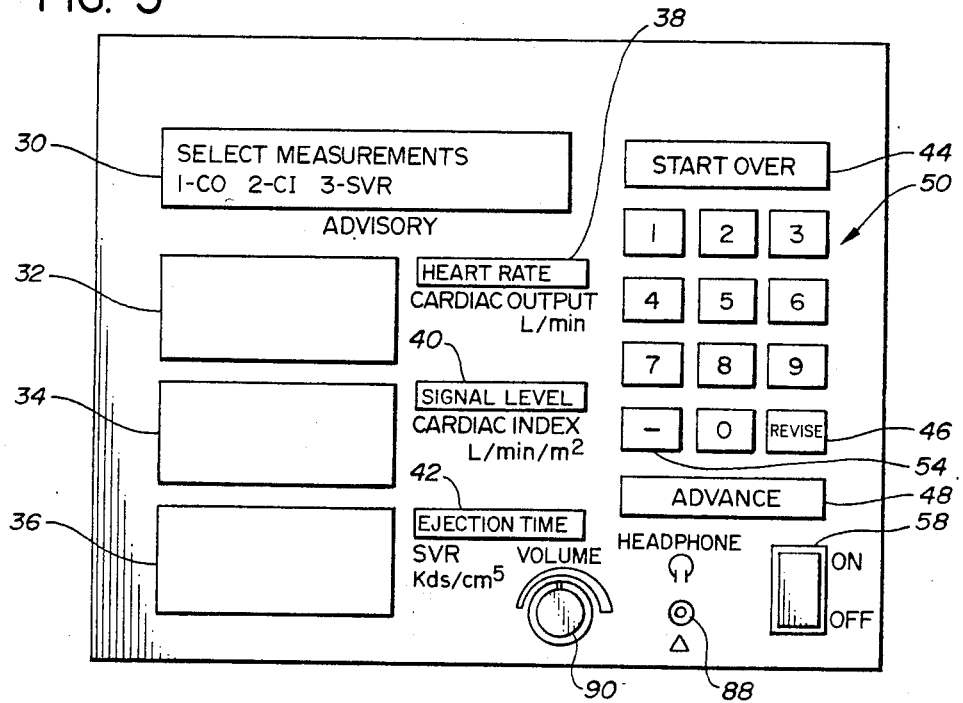
Figure 6:
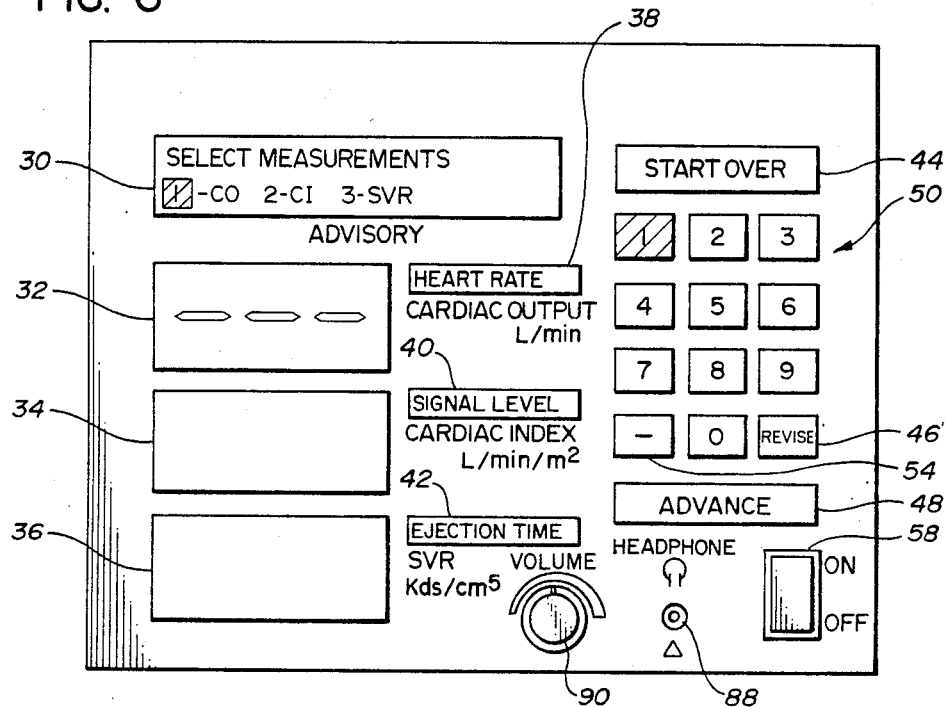
Figure 7:
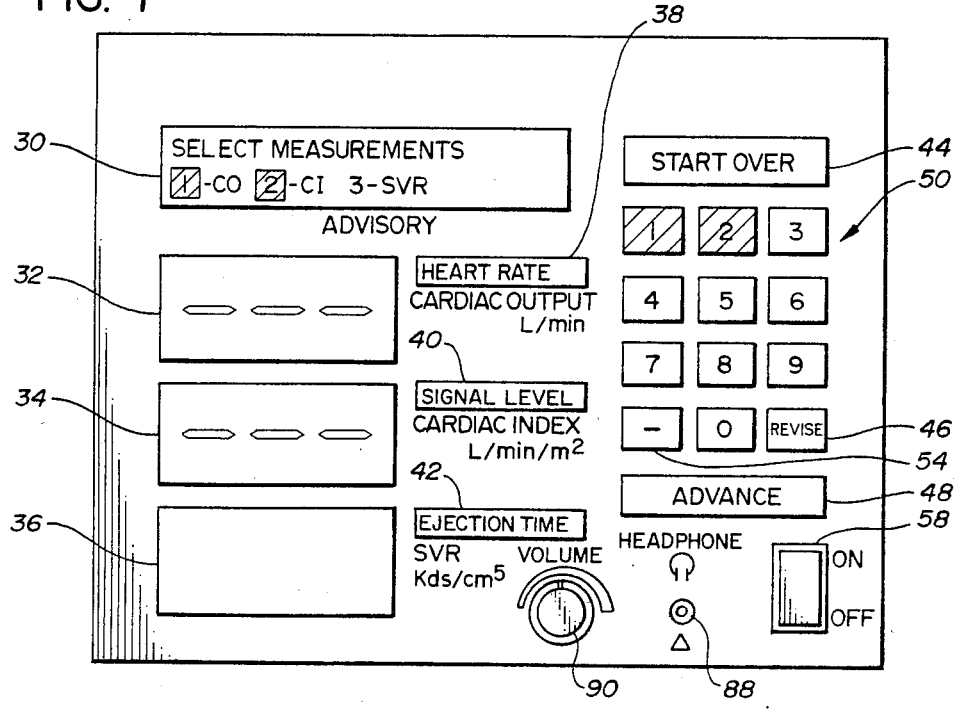

Upon completion of the self-check, the double digit 00 in LED displays 32, 34, and 36 will flash on and off three times at the rate of one cycle per second, and advisory 30 will display the message shown in FIG. 4, indicating that the cardiac monitor is operating satisfactorily and that the cardiac output measuring sequence can be initiated. Keyboard 50 will continue to ignore inputs.

When he has been advised that the machine is in a ready status, the operator pushes ADVANCE key 48. This results in advisory 30 displaying a message (shown in FIG. 5 and in block 60 in FIG. 44A) which instructs the operator to select the measurement he wishes to obtain—cardiac output, cardiac index, systemic vascular resistance, or any combination of the foregoing measurements. Cardiac output, cardiac index, and systemic vascular resistance are selected by depressing keys 1, 2, and 3, respectively, in keyboard 50. The number of the key which has been pressed in the measurement selection step flashes on message unit 30. In addition, bars appear in the appropriate LED display 32, 34, and 36 as a measurement is selected.

The keyboard 50 ignores attempts to enter instructions through the other keys while one or more of the foregoing measurements is being selected.

Table 2 below shows the measurements which can be selected and the figure of the drawing which has the advisory message for each of the seven possible selections.

TABLE 2

| Drawing Figure | Measurement(s) Selected |
| --- | --- |
| 6 | Cardiac Output |
| 7 | Cardiac Output and Cardiac Index |
| 8 | Cardiac Output, Cardiac Index, and Systemic Vascular Resistance |
| 9 | Cardiac Index |
| 10 | Systemic Vascular Resistance |
| 11 | Cardiac Output and Systemic Vascular Resistance |
| 12 | Cardiac Index and Systemic Vascular Resistance |

Figure 44B:
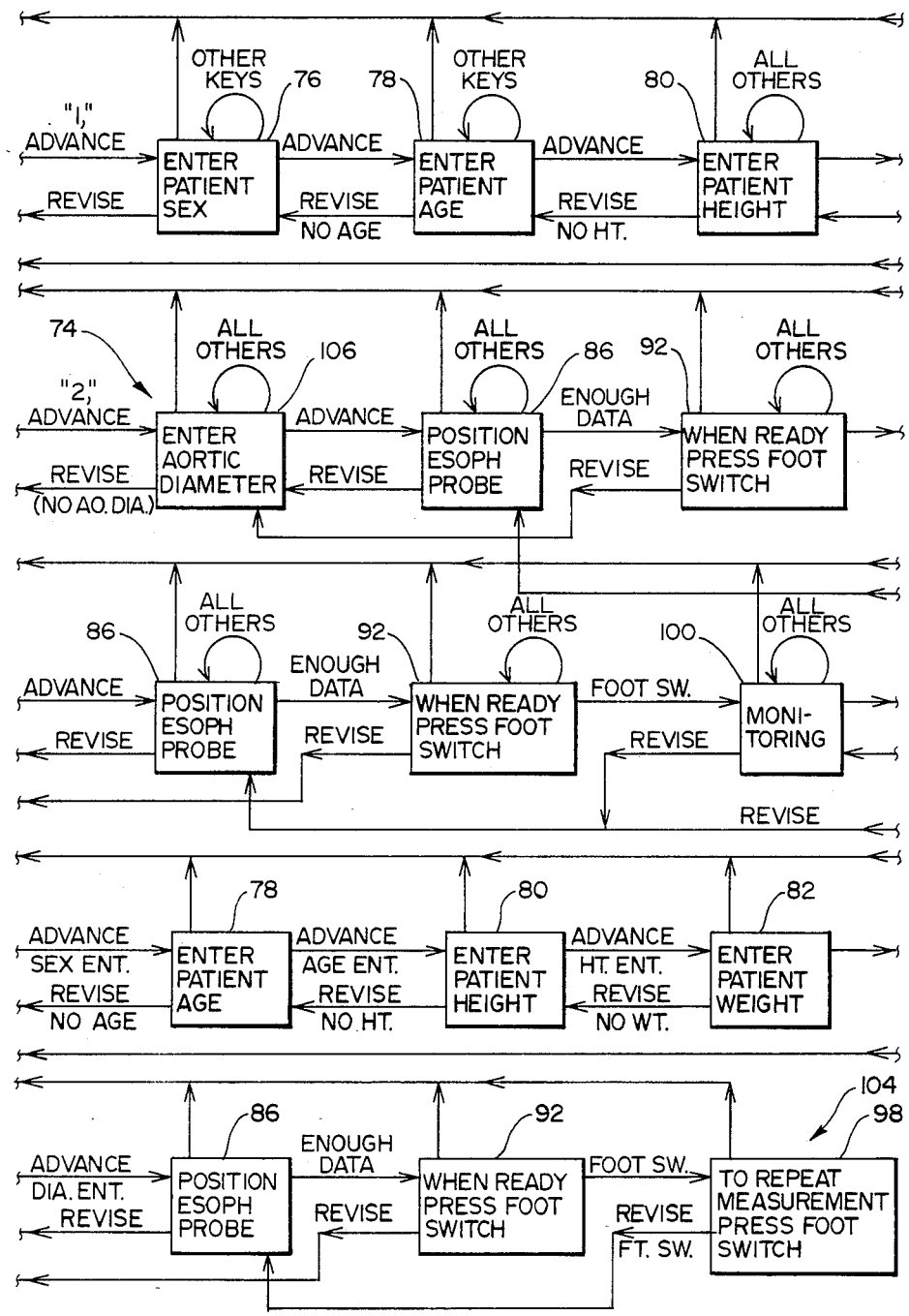
FIG. 44 shows the relationship among FIGS. 45A–45C which, collectively, show what is happening in the cardiac output monitoring apparatus as the operator interacts with that apparatus in the course of determining a patient's cardiac output.
Figure 44C:
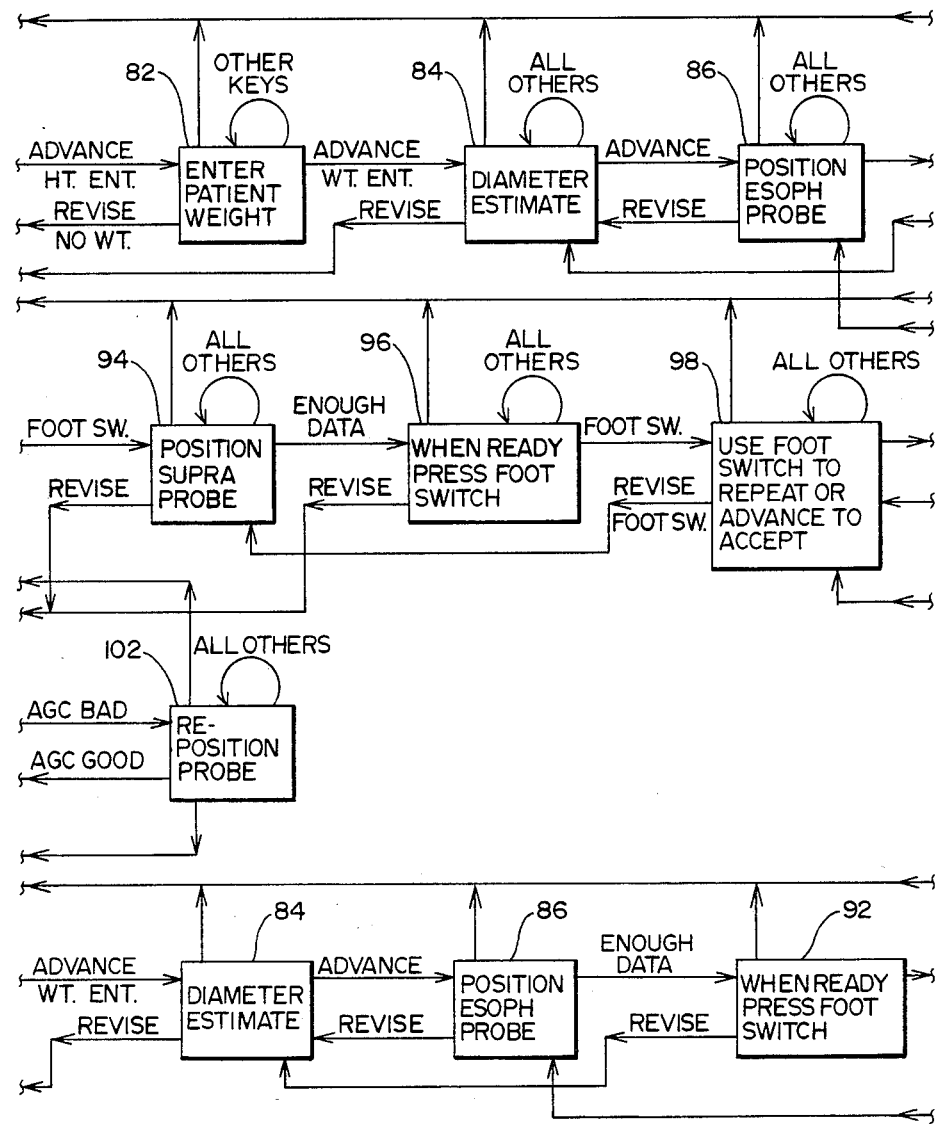
Figure 44E:
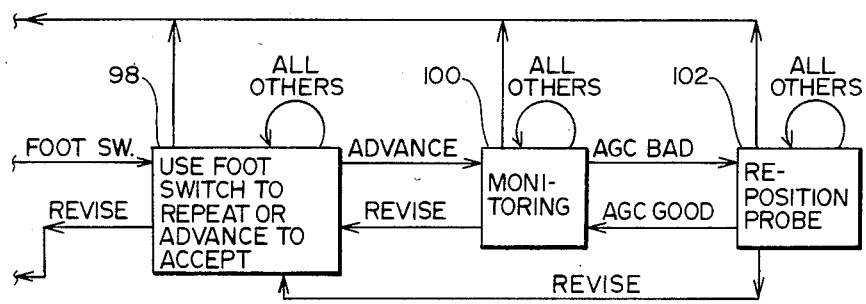

In the discussion of the operating sequence which follows, reference will also be made to FIG. 44 which is a state diagram. That diagram shows the options available to the operator at each of those steps in the operating protocol of cardiac monitor 26 following the completion of the self-check.

Labelled loops appear above certain of the blocks in the state diagram. Those labelled OTHER KEYS mean that the cardiac monitor will ignore attempts to enter data or instructions through certain of the keys in keyboard 50. The label ALL KEYS means that all attempts to employ these keys will be ignored.

Figure 13:
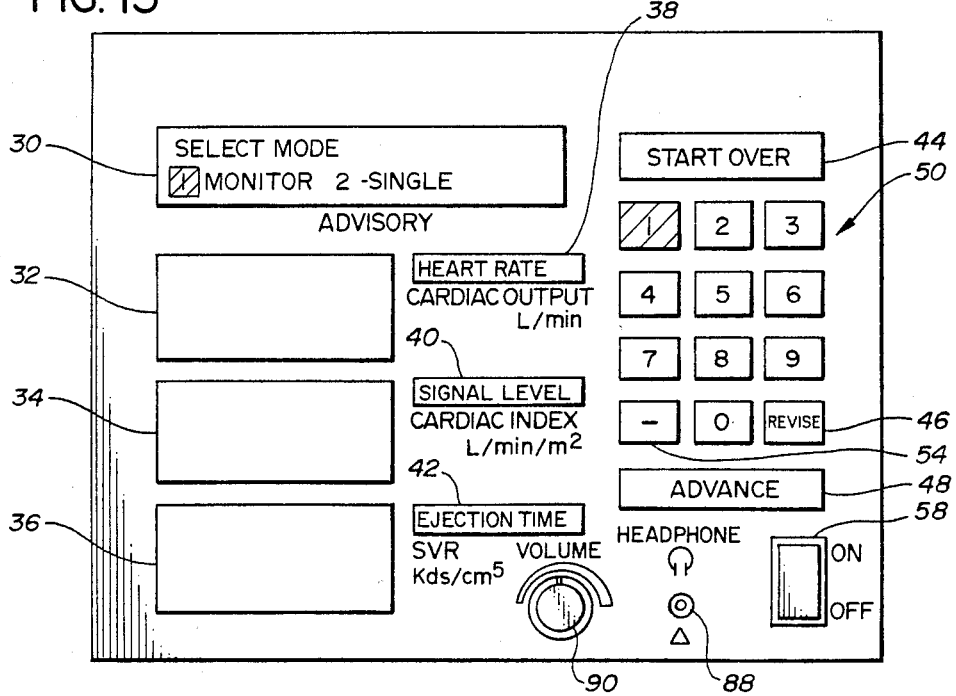

Following the selection of one or more measurements, the operator proceeds to the next step in the measurement protocol by pressing ADVANCE key 48, causing advisory 30 to display the message shown in FIG. 13 and in block 62 in FIG 44A. This instructs the operator to elect either a continuous mode of measurements or a single mode. The former is selected in circumstances where it is desirable to continuously monitor a measurement such as the cardiac output of a patient undergoing surgery. The single mode of measurement is employed when suprasternal notch probe 326 is used as discussed above to provide a one-time or infrequent determination of cardiac output.

Figure 14:
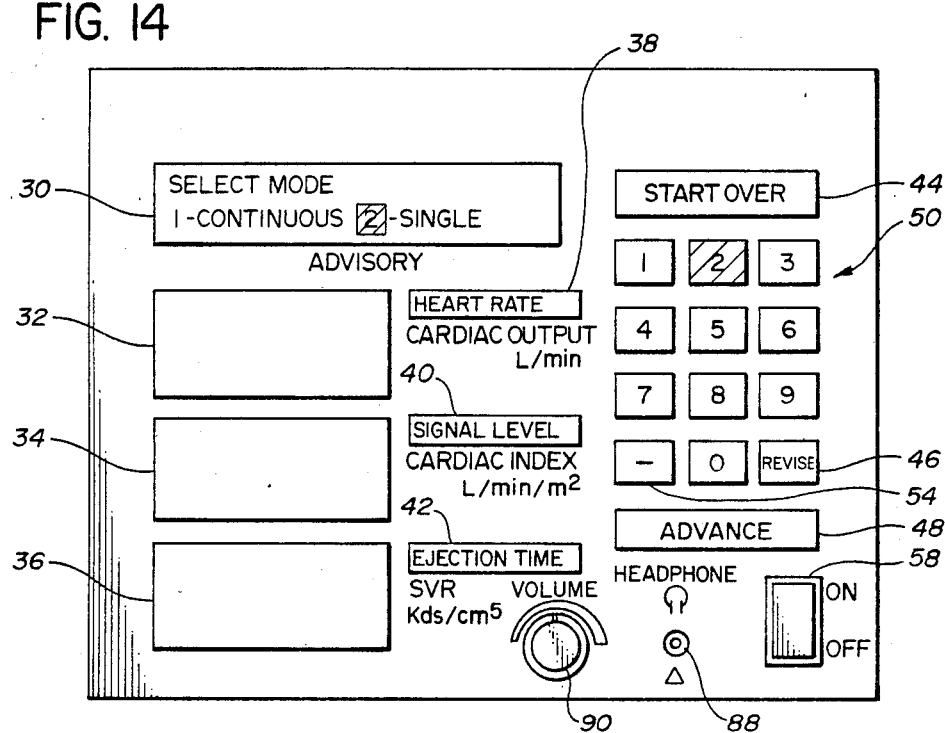

Only one mode may be selected. A second entry erases the first entry. As shown in FIGS. 13 and 14, the number 1 flashes in advisory 30 if the continuous mode of measurement is selected; "2" flashes if the single mode is selected.

Appropriate ones of the LED displays 32, 34, and 36 remain lit to identify the measurement or measurements that the operator elected.

As shown in FIG. 44A (see block 62), the operator can now press either START OVER key 44 or REVISE key 46 if he wishes to select a different measurement, or he can press ADVANCE key 48 to proceed to the next step in the operating sequence which is labelled SELECT CAL MODE in block 64 of FIG. 44A (in this and the other steps of the protocol for measuring cardiac output, the pressing of REVISE key 46 will backspace the program one step unless indicated otherwise).

As is shown in FIGS. 44A-44C, the operating sequence of cardiac monitor 26 branches at this juncture. If the operator has pressed key 1 to select a continuous mode of operation, branch 64 will automatically be followed. If, instead, key 2 is pressed to elect the SINGLE mode of operation, the branch 66 appropriate to that selection is followed. Pressing ADVANCE key 48 after key 1 brings up the SELECT CAL METHOD advisory shown in block 68 in FIG. 44A. This advisory also appears on message unit 30 of screen 28 as is shown in FIGS. 15 and 16.

The advisory also instructs the operator to press key 1 of keyboard 50 if the suprasternal notch probe method of calibrating the systolic flow velocity is to be employed and to press key 2 if a known calibration factor is to be used.

Figure 15:
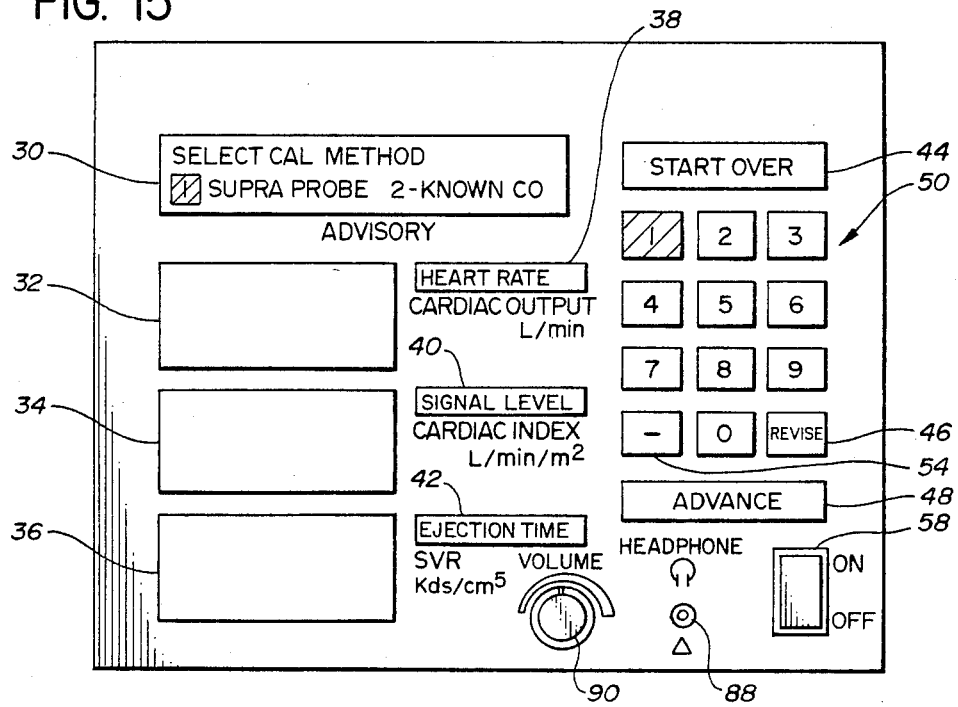
Figure 16:
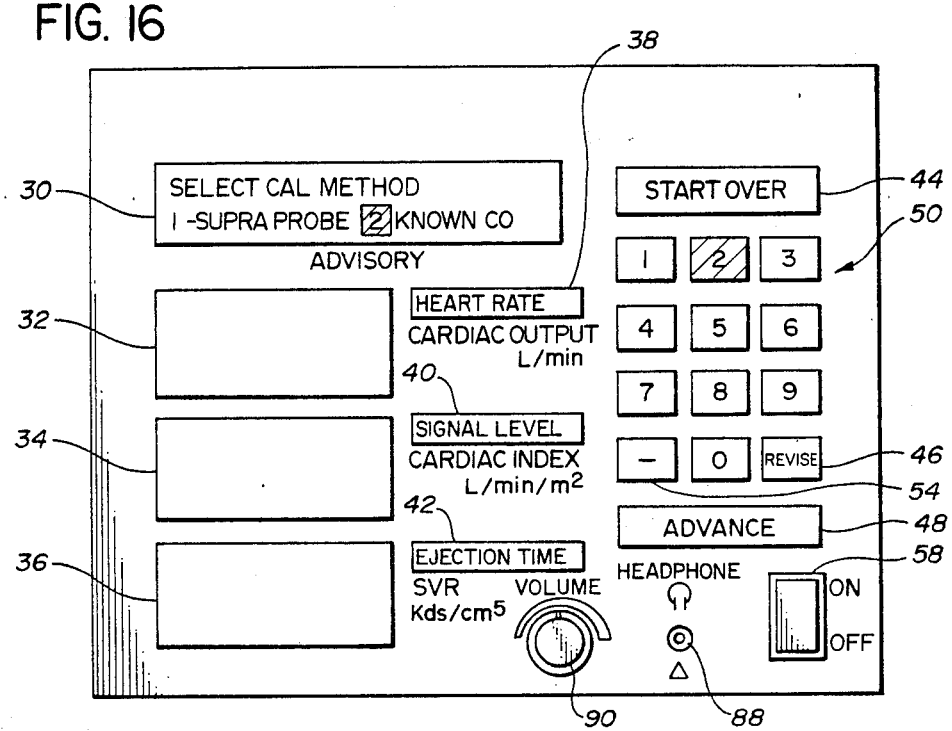

As is also shown in FIGS. 15 and 16, the numeral 1 flashes in message unit 30 if key 1 is depressed to select the suprasternal notch mode of calibration while the numeral 2 flashes if key 2 is depressed.

Only one calibration is permitted. A second selection will void the first.

The appropriate LED display or displays 32, 34, and 36 remain lighted to advise the operator of his choice of measurement or measurements.

It will be noted from FIG. 44A, that the operating protocol branches again at this point. If the SUPRA PROBE mode of calibration is elected, the sequence of steps in branch 64 will continue to be followed. Alternatively, if the patient's aortic output is known and is to be employed, the cardiac monitor 26 will automatically cause the sequence of operating steps shown in branch 70 to be followed.

Figure 17:
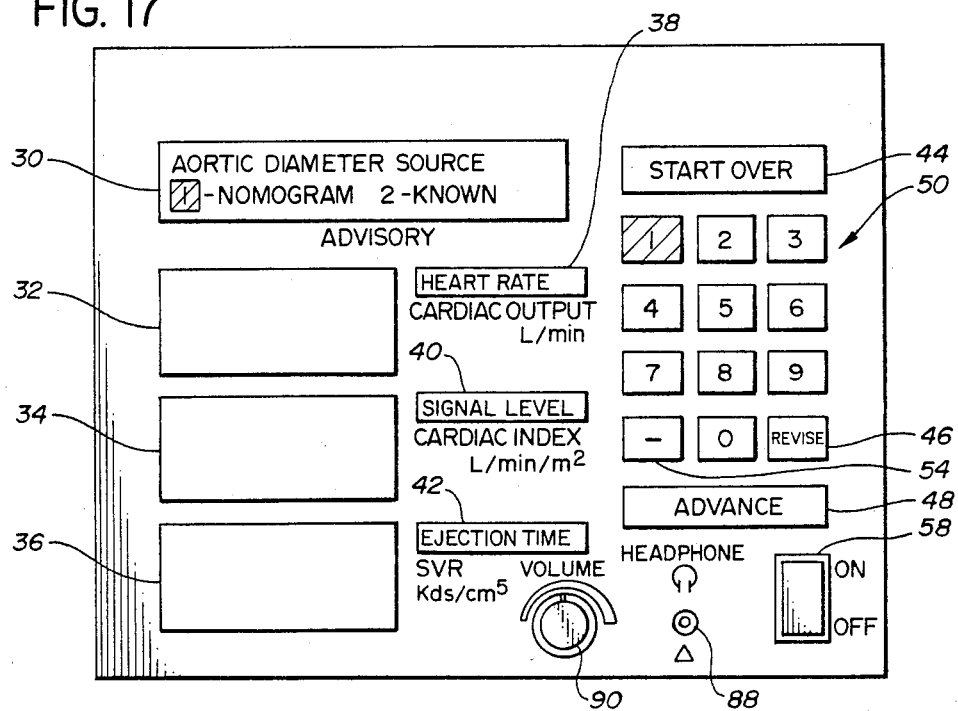
Figure 18:
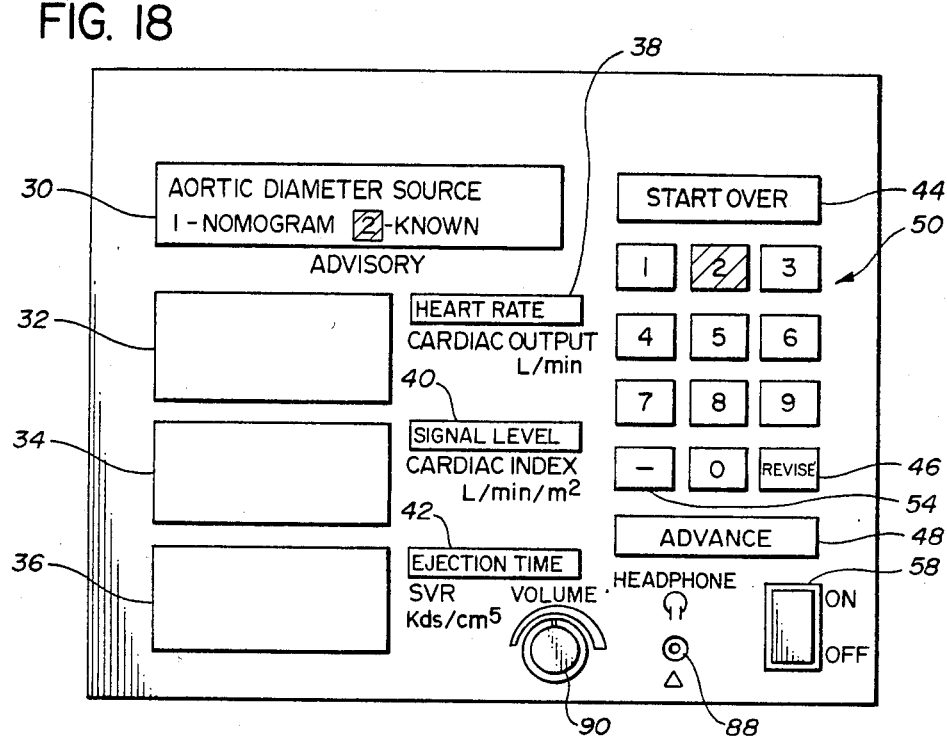

For the purposes of discussion, it will first be assumed that key 1 has been depressed to select the SUPRA PROBE method of calibration. The pressing of ADVANCE key 48 following this election brings up the message AORTIC DIAMETER SOURCE shown in block 72 of FIG. 44A. This advisory also appears on message unit 30 as shown in FIGS. 17 and 18.

Two choices are available. The diameter of the patient's ascending aorta may be automatically calculated from his height, weight, age, and sex by solving the algorithm discussed above. Alternatively, this diameter may be known and the electron be to use the known value.

Key 1 is pushed to elect the NOMOGRAM method, and key 2 is pushed to select KNOWN. The number 1 will flash on message unit 30 if NOMOGRAM is selected, and numeral 2 will flash if KNOWN is chosen.

Only one selection is permitted with a subsequent entry voiding a preceding one.

Appropriate LED displays 32, 34, and 36 remain lighted.

The operator may proceed to the next step in the operating sequence by pressing ADVANCE key 48. The depression of key 48 is accompanied by still another branching of the operating sequence. If the NOMOGRAM method of determining aortic diameter is elected, the sequence of steps shown in original branch 64 will be followed. Alternatively, if KNOWN is selected, the sequence of steps shown in branch 74 will be followed instead.

Here, again, an explanation of the steps in the sequence designated branch 64 will be continued in the interest of clarity.

Figure 19:
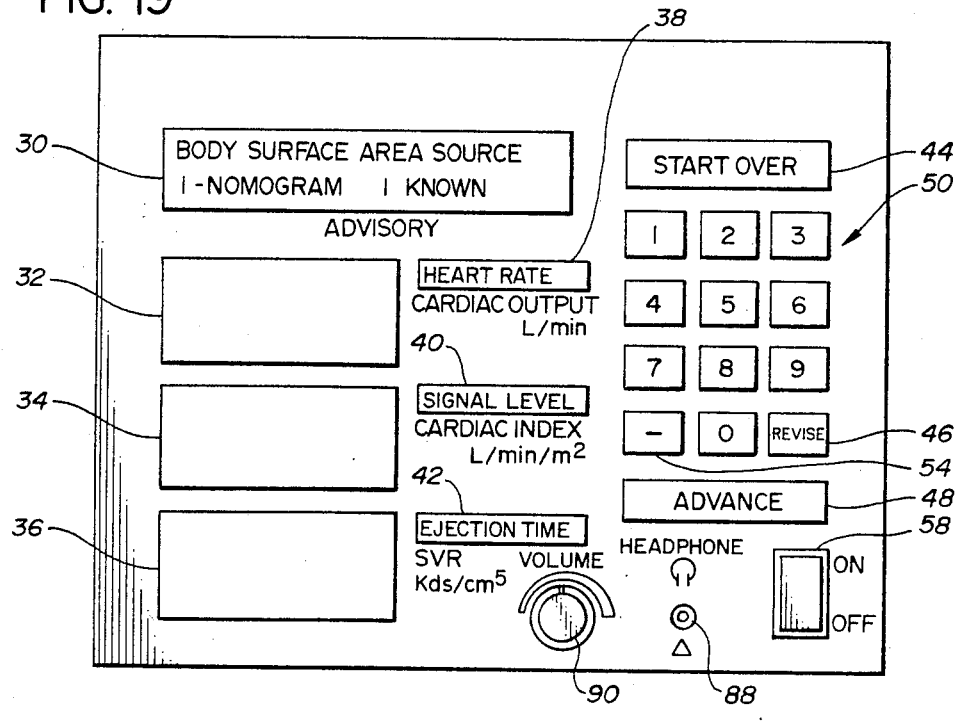

The depressing of key 1 to select the NOMOGRAM method of ascertaining the patient's aortic diameter followed by the pressing of ADVANCE key 48 brings up the advisory ENTER PATIENT'S SEX shown in block 76 in FIG. 44A with the same instruction being displayed in advisory unit 30 of visual display 28 as is shown in FIGS. 18 and 19. The advisory also instructs the operator to press key 1 if the patient is a male and to press key 2 if she is a female.

Figure 21:
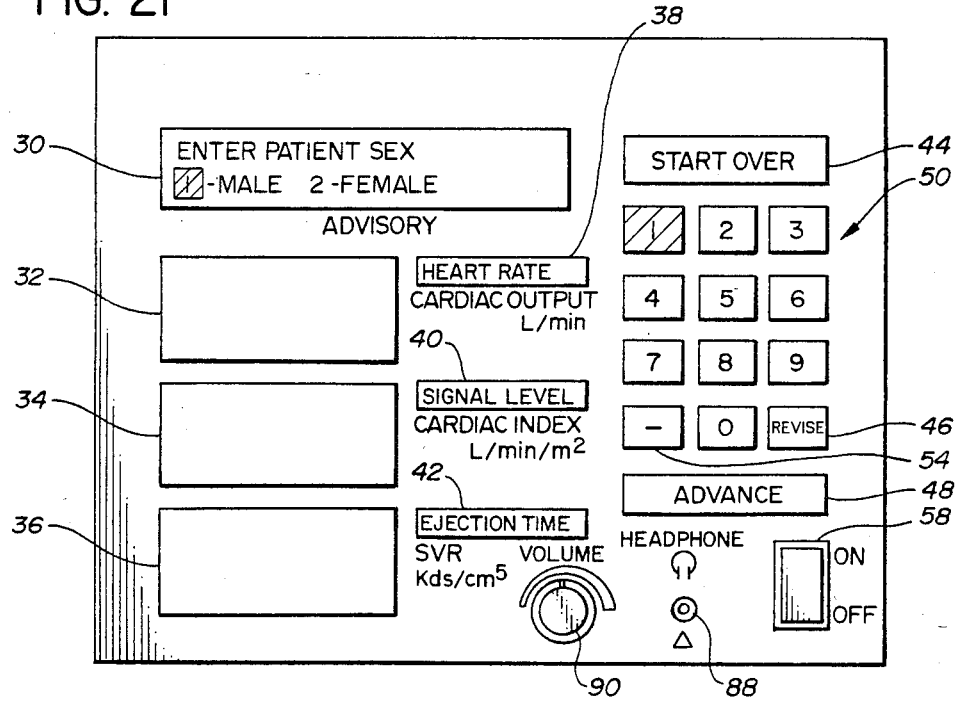
Figure 22:
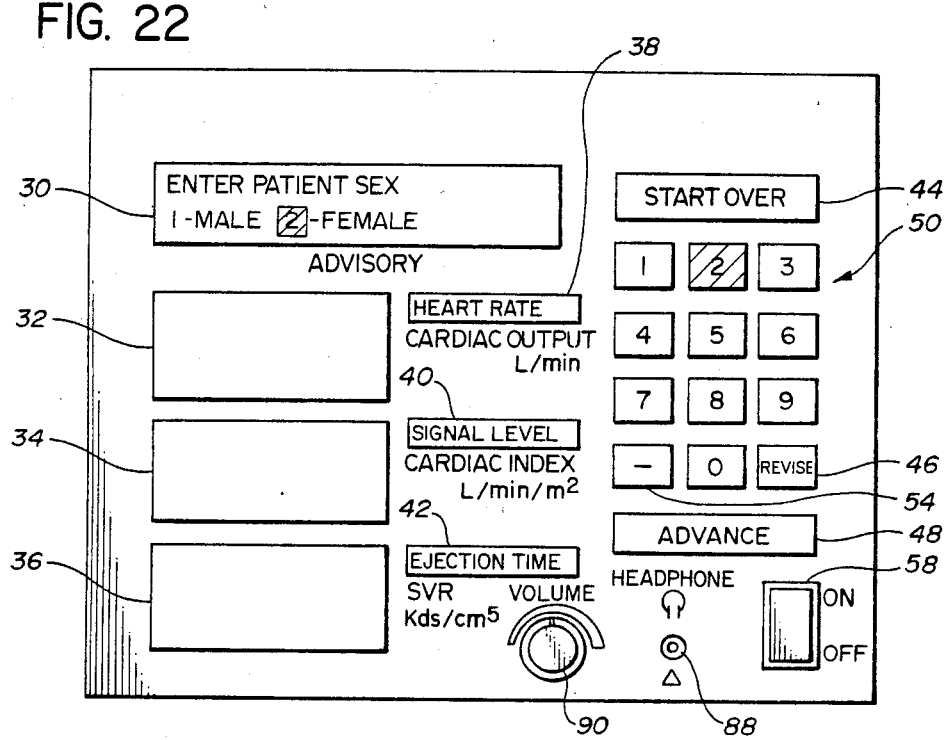
Figure 23:
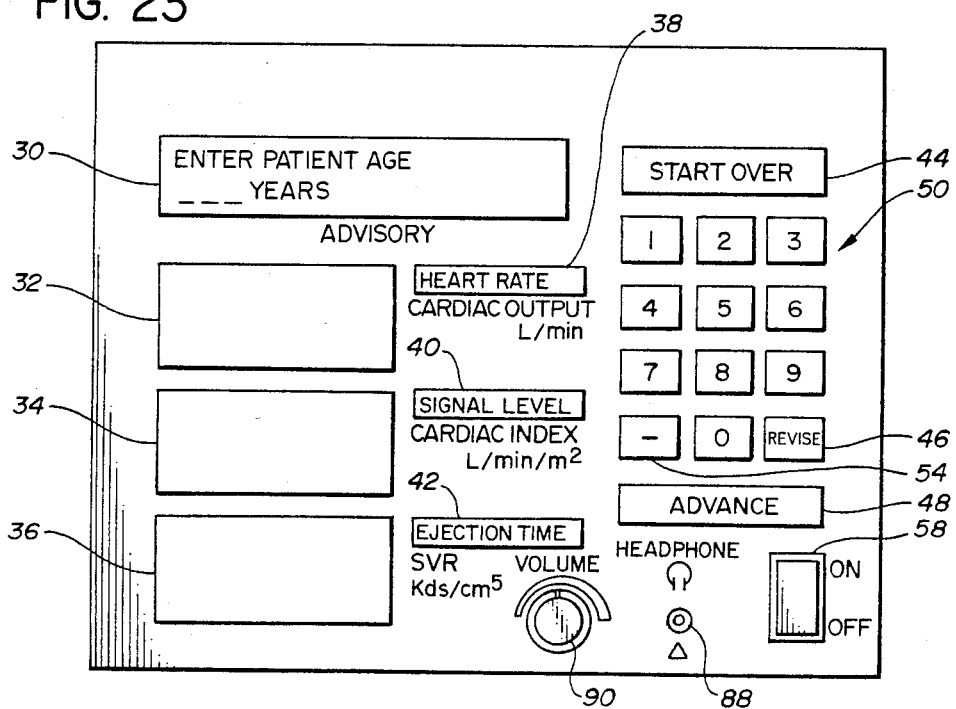

The numeral 1 will flash on the advisory if key 1 is pressed, and the numeral 2 will flash if key 2 is pressed (see FIGS. 21 and 22, respectively). Only one choice is permitted; any subsequent entry voids the preceding one.

Again, the appropriate LED displays 32, 34, and 36 remain lighted so that the operator will remain aware of the measurements (cardiac output, cardiac index, and systemic vascular resistance) he has elected.

To advance to the next step in the operating sequence, the operator presses ADVANCE key 48, bringing up instructions to enter the patient's age. The message, ENTER PATIENT's AGE, is shown in block 78 in FIG. 46B and in FIG. 23.

The patient's age (in years) is entered by pressing the appropriate keys on keyboard 50. The numbers which are entered (maximum of three) are displayed in advisory 30 so that the operator can visually confirm that he has correctly entered the patient's age.

The appropriate LEDS 32, 34, and 36 still remain lighted to call to the operator's attention the measurement choices he has made.

Figure 24:
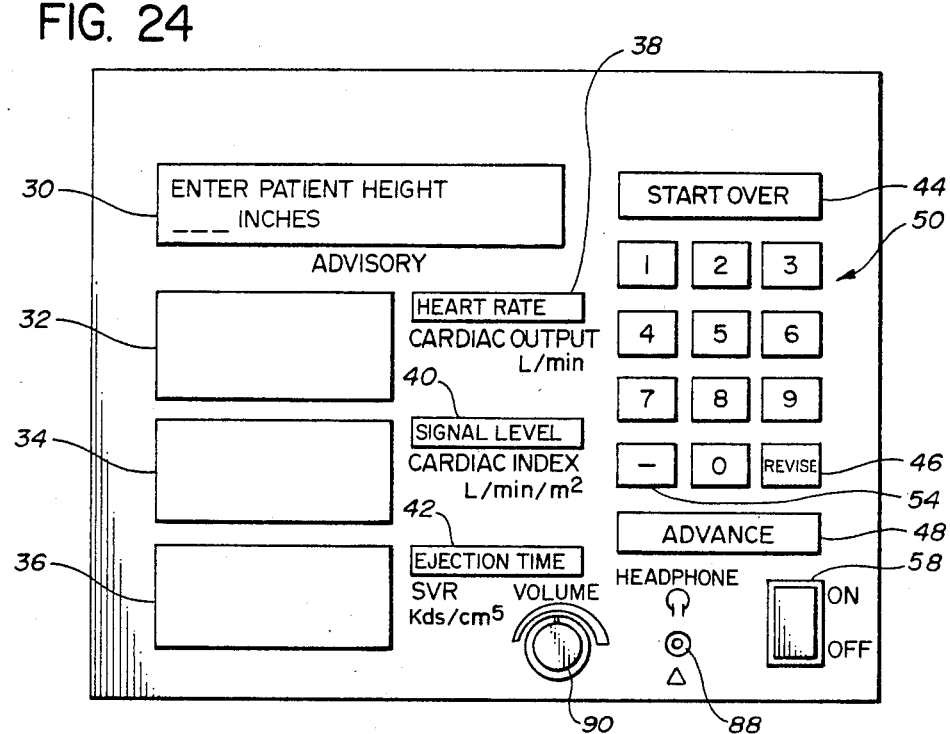
Figure 25:
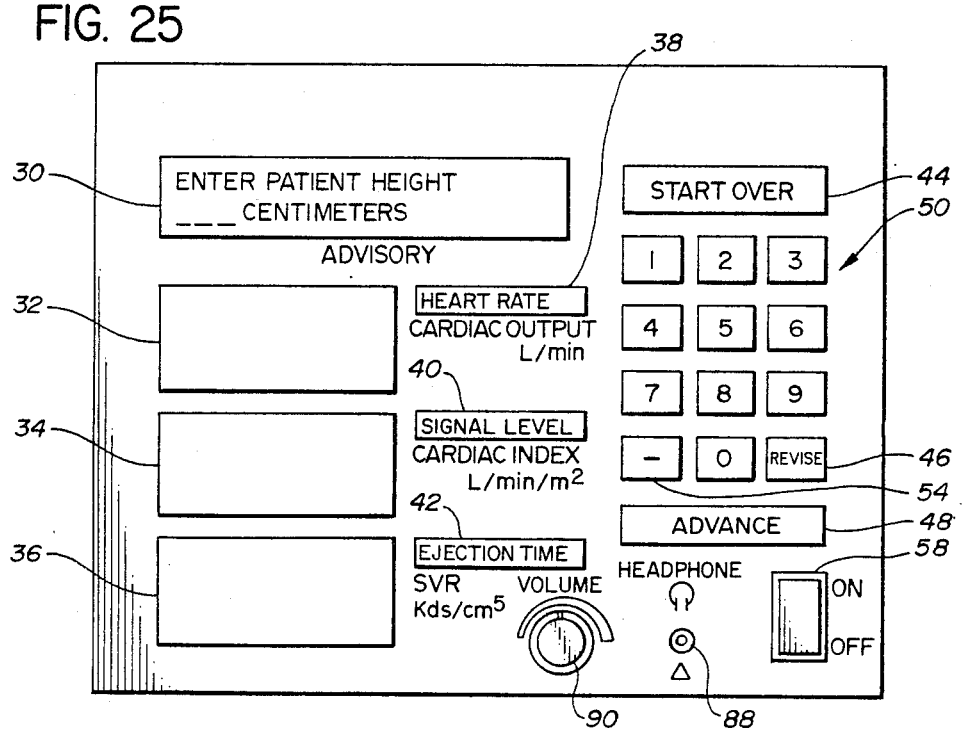
Figure 26:
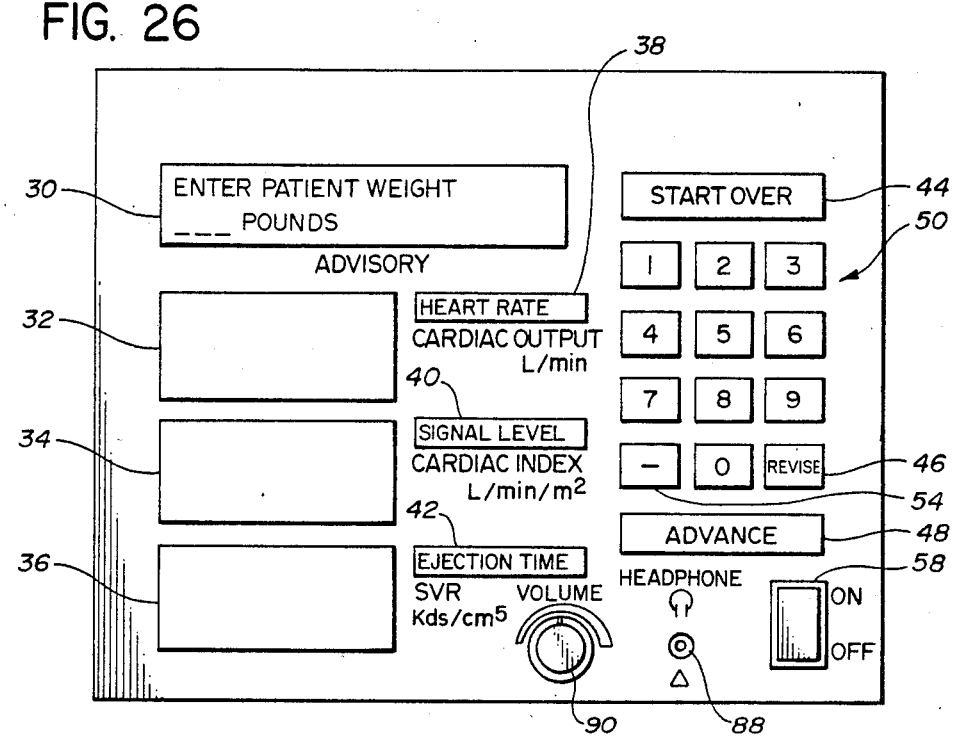

Pressing the ADVANCE key 48 after the patient's age has been entered brings up the instruction ENTER PATIENT HEIGHT (block 80 of FIG. 46B) and FIGS. 24 and 25. The patient's height in inches (FIG. 23) is entered by pushing not more than three keys on keyboard 50. The entry is displayed in advisory 30, allowing the operator to confirm that the entry was correctly made.

The LED displays remain unchanged at this point.

Referring now to FIG. 25, the patient's height can be entered in centimeters instead of inches. Cardiac monitor 26 is programmed to automatically identify the system of measurement. It will be appreciated that this is easily accomplished because the sets of numbers are quite different in the two systems. For example, if the patient is six feet tall, 72 will be entered if the information is available in the English system while 178 will be entered if the information is instead in the metric system.

After the height entry has been completed, the operator presses ADVANCE key 48 to bring up the next step in the sequence shown in branch 64. This step is designated ENTER PATIENT WEIGHT in block 82 of FIG. 64A and in advisory 30 (see FIGS. 26 and 27).

Figure 27:
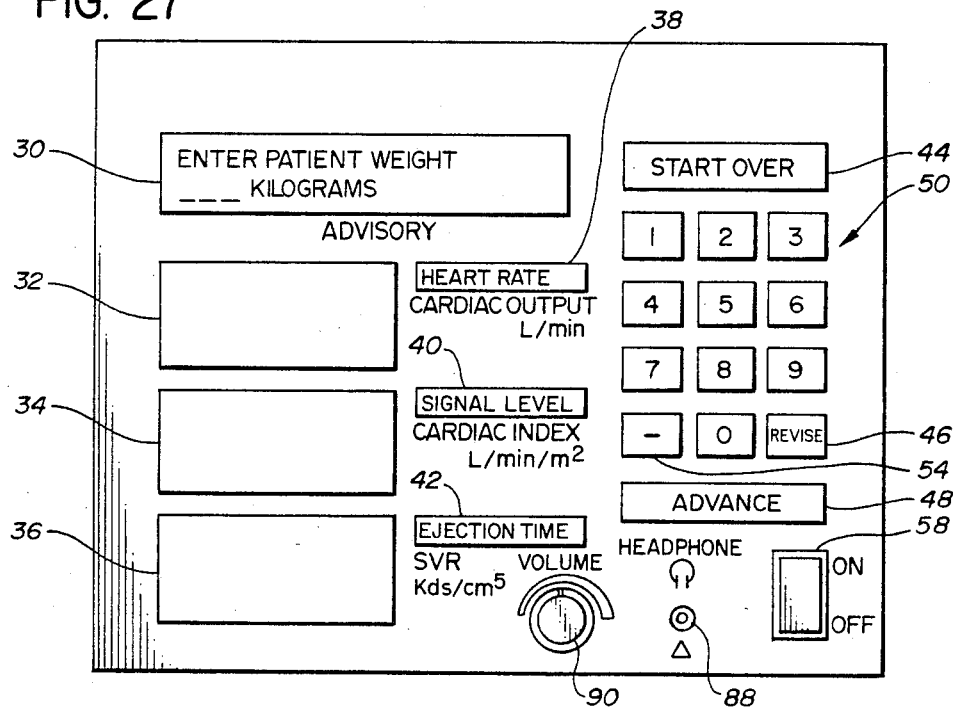
Figure 28:
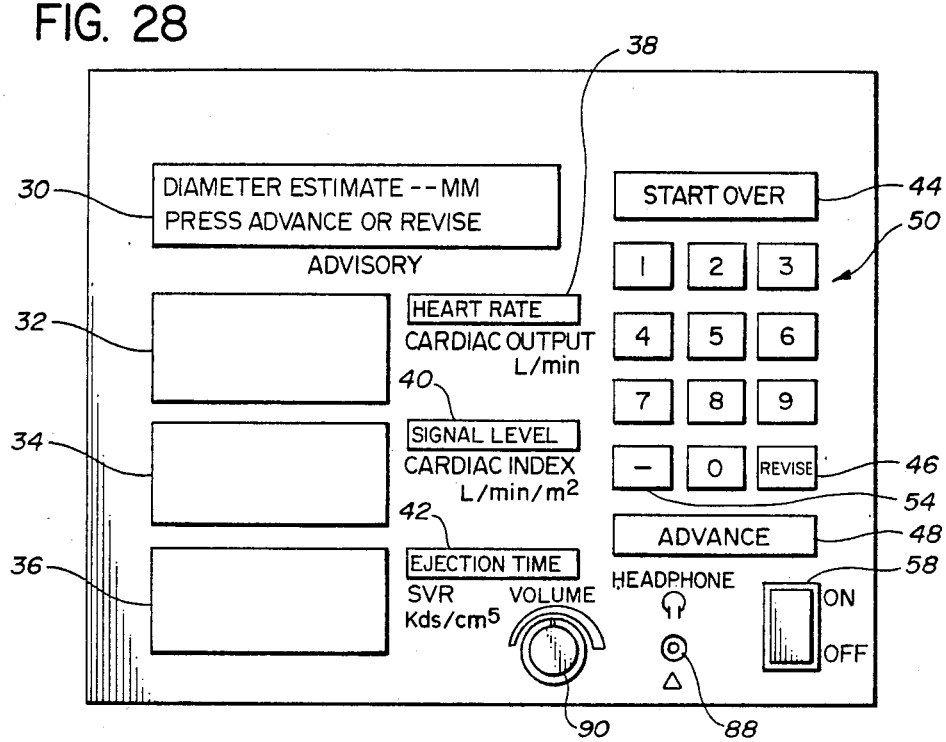

The patient's weight is entered from keyboard 50, and it may be entered in either pounds (FIG. 26) or in kilograms (FIG. 27). Again the cardiac monitor is capable of discriminating between English and metric system entries without input from the operator.

No more then three weight indicating digits can be entered. These are displayed in advisory 30, again allowing the operator to confirm that his entry was properly made.

After the patient's weight is entered, the operator presses ADVANCE key 48 to proceed. At this point, the message DIAMETER ESTIMATE appears (see block 84 in FIG. 46B). That message also appears in advisory 30 along with the aortic diameter calculated in cardiac monitor 26 from the patient's height, weight, age, and sex. If the displayed aortic diameter appears credible, the operator can press key 48 and advance to the next step in the operating sequence shown in branch 64. If the information appears inaccurate, the operator presses REVISE key 46 which, in this case, brings up AORTIC DIAMETER SOURCE (see block 72 in FIG. 44A). This allows the patient's aortic diameter to be recalculated or replaced with an otherwise obtained aortic diameter measurement.

The LED displays 32, 34, and 36 indicative of the measurement or measurements selected by the operator continue to be lighted while DIAMETER MEASUREMENT is displayed.

By pressing ADVANCE key 48, the operator next brings up the instruction POSITION ESOPH PROBE shown in block 86 and in FIG. 44B. This message also appears in advisory 30 (see FIG. 35).

At this point, the backlighted LED displays, 38, 40, and 42 designated HEART RATE, SIGNAL LEVEL, and EJECTION TIME are illiminated.

The operator now introduces esophageal probe 220 into the patient's mouth, floats it downwardly through his esophagus, and rotates the probe's ultrasonic transducer until the optimal return or reflected-energy signal is obtained.

We pointed out above that this positioning of probe 220 is facilitated by both visual and aural signals. The visual indicators are heart rate, signal level, and ejection time. The values of these measurements appear on LED displays 32, 34, and 36.

The audio signals are monitored by headphones (not shown) plugged into a jack 88 which is accessible from the front panel of the console. Also accessible from this panel is a volume control 90 which is coupled to potentiometer 466 (see FIG. 56G).

Appropriate circuitry for deriving the audio signal from the frequency-shifted signal generated by the esophageal probe is described above.

Advance key 48 is ignored during the POSITION ESOPH PROBE step.

Revise key 46 resumes its more commonn function at this junction. Depression of that key only backspaces the protocol to DIAMETER ESTIMATE.

Figure 36:
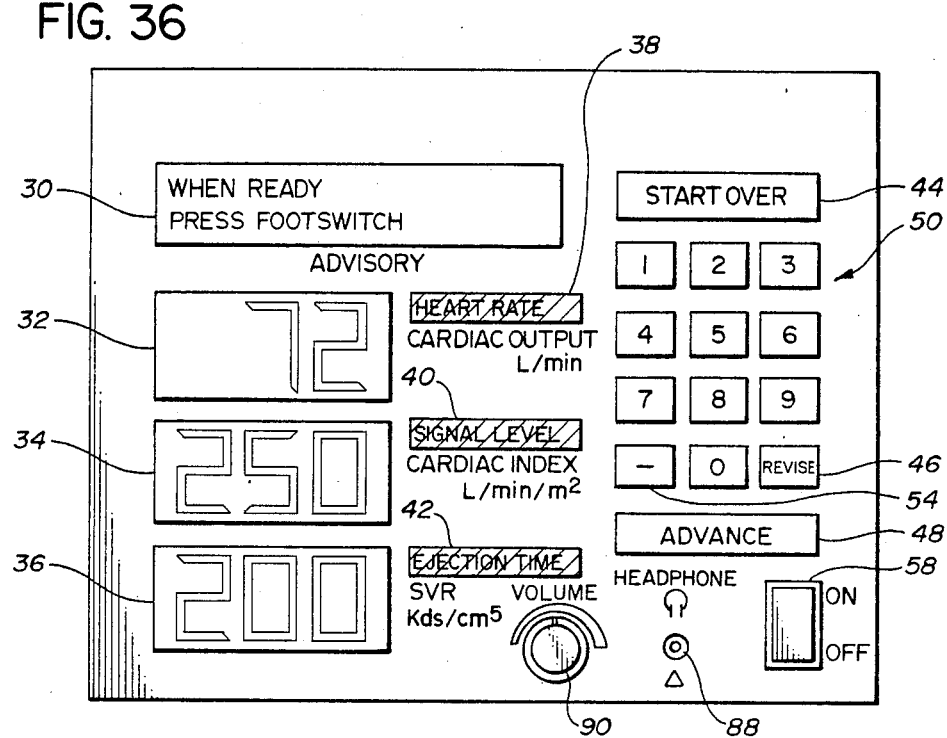

If the operator is satisfied that the esophageal probe 220 has been located in an optimal position and that he has entered the data needed for an accurate measurement of the patient's cardiac output, he presses ADVANCE key 48, bringing up the instruction WHEN READY PRESS FOOT SWITH shown in block 92 in FIG. 44C and in FIG. 36. This decision is based on the heart rate, signal level, and ejection time values (LED displays 32, 34, and 36) and by the protocol the operator is employing to aim the esophageal probe.

The values shown in FIG. 36 are typical. The actual values will depend on the patient's condition and will vary from patient-to-patient.

The cardiac monitor ignores ADVANCE key 48 while the WHEN READY message is displayed.

Unless he wishes to start over, or return to the POSITION ESOPH PROBE step, the operator next presses footswitch 56.

Figure 37:
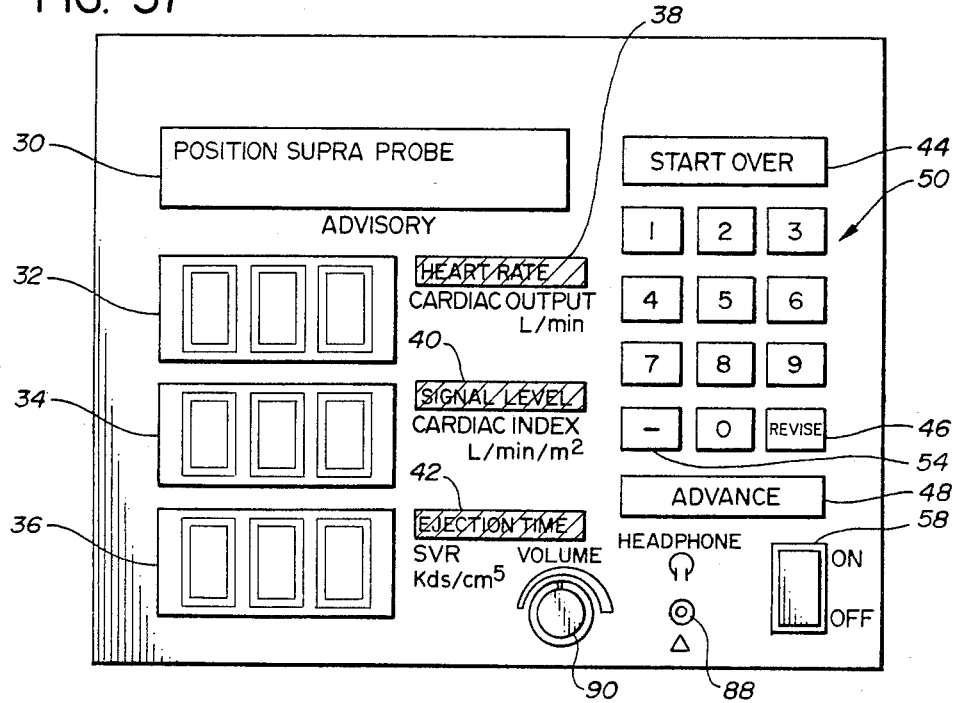

The pressing of footswitch 56 following the appearance of the when ready message brings up the instruction POSITION SUPRA PROBE shown in block 94 in FIG. 46C and in FIG. 37. At this point the HEART RATE, SIGNAL LEVEL, and EJECTION TIME displays 38, 40, and 42 will still be lighted; and the values of these measurements will appear in LED displays 32, 34, and 36, respectively.

The operator now proceeds to position suprasternal notch probe 220 as discussed above and in more detail and obtains a measurement of the patient's cardiac output that can be used to calibrate the systolic velocity of the blood flowing through his descending aorta.

While the calibration measurement is being calculated, the operator can start over or press REVISE key 46 to return to the step designated POSITION ESOPH PROBE. ADVANCE key 48 is ignored.

Figure 38:
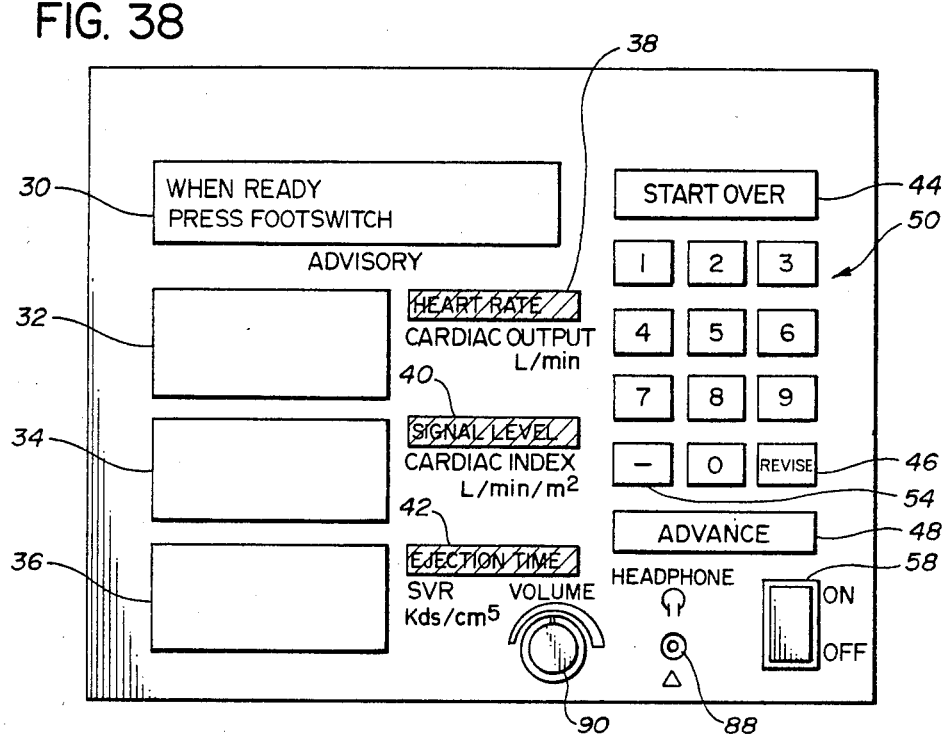
Figure 39:
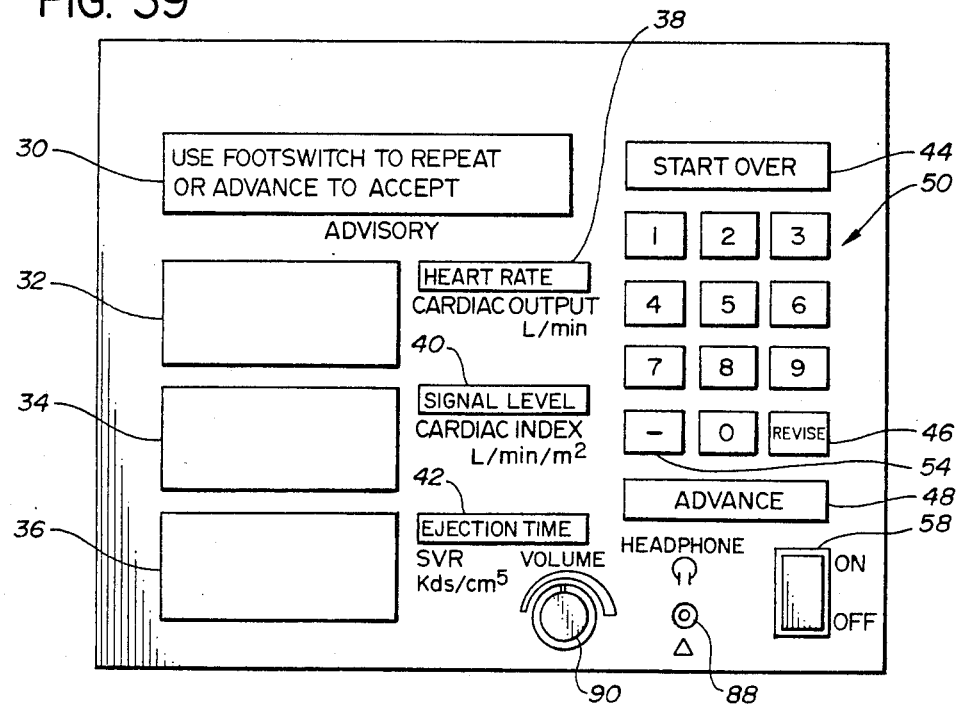
Figure 40:
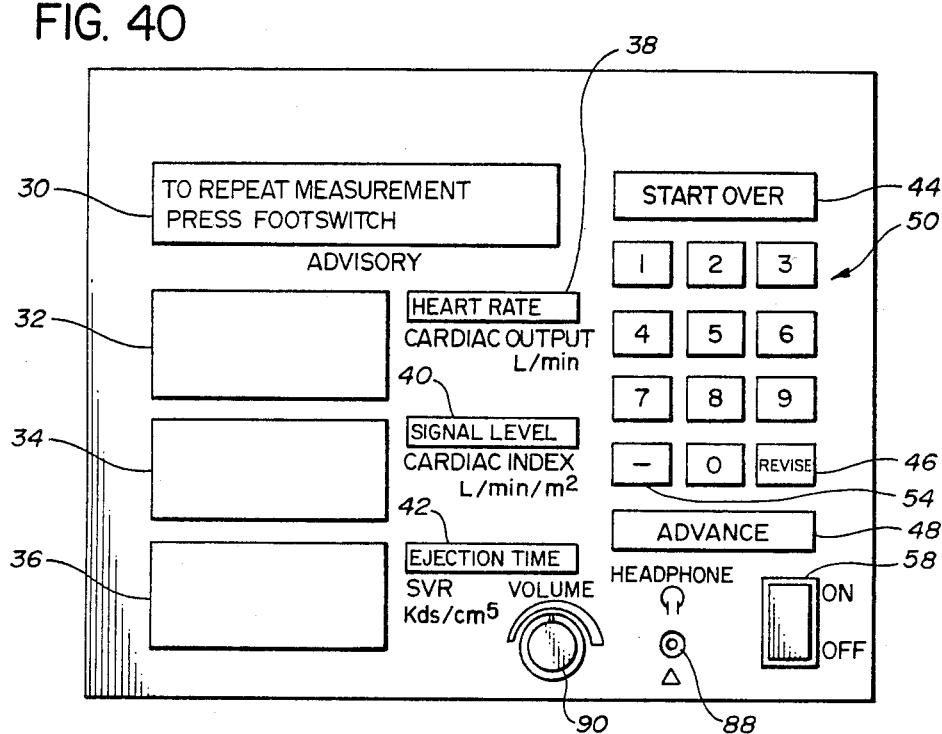
Figure 41:
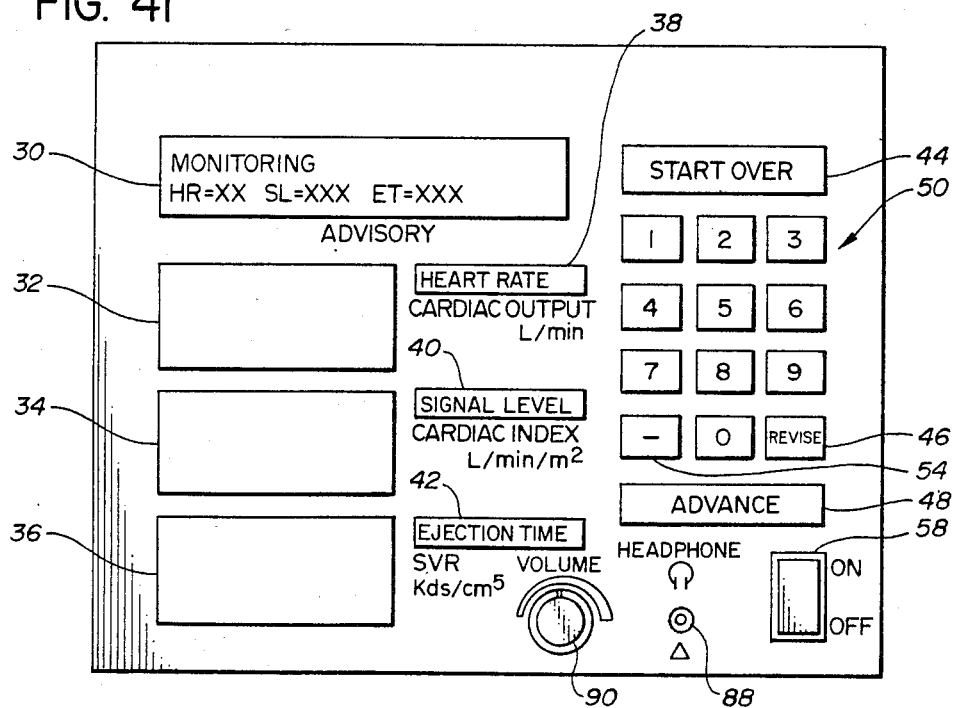
Figure 42:
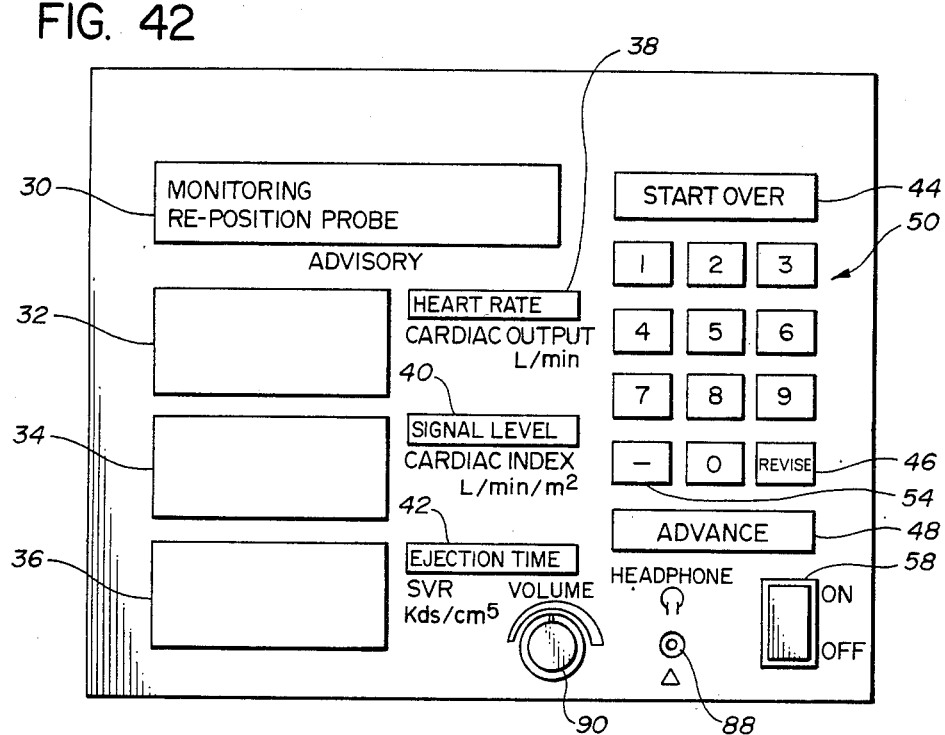
Figure 43:
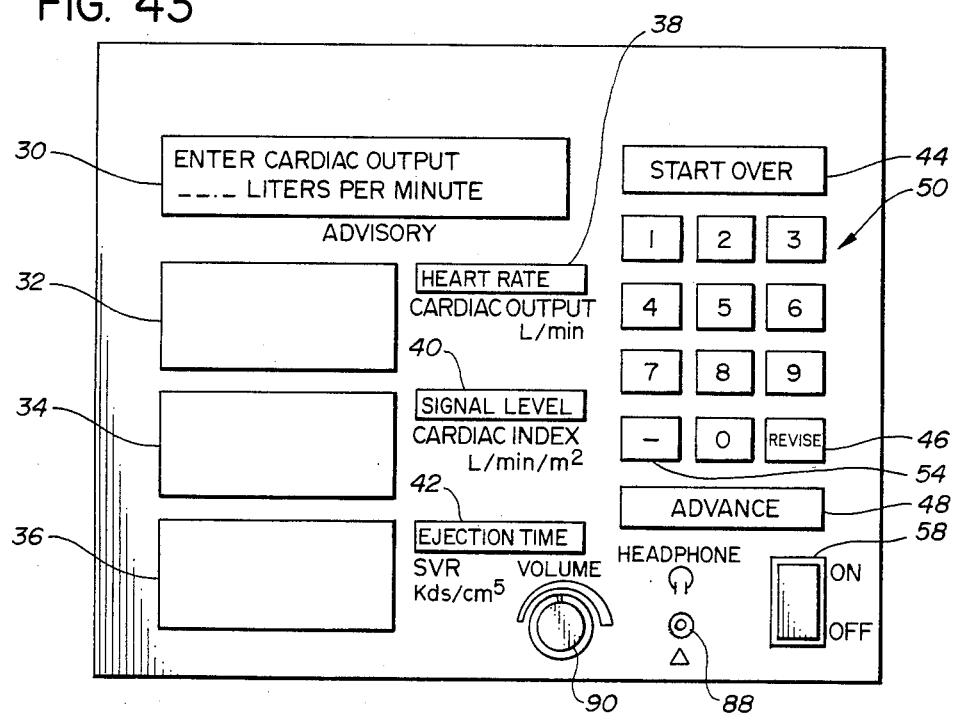

When enough data to calculate the conversion factor has been accumulated, a second instruction labelled WHEN READY PRESS FOOTSWITCH will appear as shown by block 96 in FIG. 44C and in FIG. 38. From the values of heart rate, signal level, and ejection time appearing in LED displays 32, 34, and 36 and the protocol for aiming the suprasternal notch probe, the operator can determine if the probe has been manipulated into an orientation that will provide a satisfactory measurement of the patient's ascending aorta systolic blood flow. If he is convinced that it has, he depresses footswitch 56, calling up the instruction USE FOOTSWITCH TO REPEAT OR ADVANCE TO ACCEPT (block 98 and FIG. 39).

If the operator is not satisfied with the results displayed by the LED displays, he can use the footswitch to return to the step designated POSITION ESOPH PROBE. Or he can use ADVANCE key 48 to bring up the next advisory, MONITORING, (block 100 and FIG. 42).

Pressing footswitch 56 will cause the LED displays HEART RATE, SIGNAL LEVEL, and EJECTION TIME to be extinguished.

If the ADVANCE TO ACCEPT alternate is elected, the cardiac monitor will calculate the factor for converting the systolic flow velocity in the patient's descending aorta to the systolic velocity in his ascending aorta and monitor the cardiac output of the patient on a continuous or beat-to-beat basis.

The advisory 30 will display the current value of the measurement or measurements selected by the examiner in the SELECT MEASUREMENT step of the operating sequence.

The operator has the option of employing START OVER key 44 and REVISE key 46 while the cardiac monitor is monitoring the selected measurement or measurements.

It is possible that esophageal probe 220 may shift while the vital signals are being monitored. If so, an automatic gain controller as disclosed above will cause the message REPOSITION PROBE shown in box 102 in FIG. 46C to appear. At this juncture the operator has the option of starting over, pressing REVISE key 46, or of repositioning the probe. If the latter option is excercised, and the gain returns to an acceptable level, the monitoring of the selected measurements will resume as is apparent from FIG. 46C.

Referring now back to FIG. 44A, that branch of the protocol we employ for determining a patient's cardiac output was followed because the operator elected to employ a continuous as opposed to single or one-time mode of measurement. Had he instead elected the single mode (see FIG. 13), the sequence of steps in branch 66 would be followed. The first of these, discussed above and brining up the message AORTIC DIAMETER SOURCE (see FIG. 17), requires that the diameter of the patient's ascending aorta be calculated from his height, weight, age, and sex in the manner discussed above and in more detail or that a known aortic diameter be available. If the operator elects the former option, the steps in branch 66 will be followed to completion. If he instead employs the alternate option, the steps in yet another branch 104 of our novel operating protection will be followed.

The steps discussed above in conjunction with branch 64 of the operating sequence and identified by reference characters 76, 78, 80, 82, 92, and 98 (see, also, FIGS. 17, 18, 21, 22, 23, 24, 25, 26, 27, 28, 29, 37, 38, and 40) are followed in branch 66 to provide one or more measurements of the patient's cardiac output via the suprasternal notch probe approach.

If, in responding to the message designated AORTIC DIAMETER SOURCE, the operator elects to employ a known measurement by pushing key 2 on keyboard 50 and then ADVANCE key 48: (1) branch 104 will be followed instead of branch 66; (2) the message ENTER AORTIC DIAMETER shown in block 106 in FIG. 46A will be brought up; and (3) the operator will enter the known aortic diameter, employing keyboard 50 for that purpose.

Next, the examiner can press ADVANCE key 48, bringing up the message POSITION SUPRA PROBE which is followed by the steps shown at 96 and 98 in branch 64 of the operating sequence and discussed above in conjunction with that branch.

The result of employing the steps in branch 104 is, again, one or more measurements of the patient's cardiac output employing the suprasternal notch probe approach.

It will also be remembered from the discussion of the instruction SELECT CAL METHOD (block 68 in FIG. 44A and FIGS. 15 and 16) that the systolic velocity of the blood flowing through the patient's descending aorta can be calibrated, or scaled upwardly, by either the suprasternal notch probe approach or by employing a known calibration factor. The former approach is employed in the sequence of operating steps designated branch 64. If the operator instead presses key 2 of keyboard 50 and then ADVANCE key 48 (see FIG. 16), the message ENTER CARDIAC OUTPUT shown in box 108 in FIG. 46A will be brought up. The operator enters this requested information through keyboard 50.

Pressing ADVANCE key 48 again brings up the advisories shown in boxes 86, 92, 100, and 102 (FIGS. 44A and 44B) and in FIGS. 35, 36, 41, and 42 to provide continuous or beat-by-beat measurement of the patient's cardiac output.

The sequence of steps in the fifth branch 74 of the operating protocol is followed when, in response to the advisory ENTER DIAMETER SOURCE (see box 72 in FIG. 44A and FIG. 18), the operator first depresses key 2 in keyboard 50 and then ADVANCE key 48. This brings up the advisory ENTER AORTIC DIAMETER shown in box 106 in FIG. 44A. The information requested by this advisory is entered by using the keys in keyboard 50.

The next seven steps in the sequence identified as branch 74 are identical to the last seven steps designated by reference characters 86, 92, 94, 96, 98, 100, and 102 in branch 64 of the operating protocol (see FIGS. 44B and 44C). Following these steps produces continuous or beat-by-beat monitoring of the patient's cardiac output.

As will be obvious from FIGS. 44A–44C, the operator has the same revise and start over options in following the branches 74, 70, 66, and 104 of the operating protocol that he does in following the first-discussed sequence of steps designated branch 64.

Figure 8:
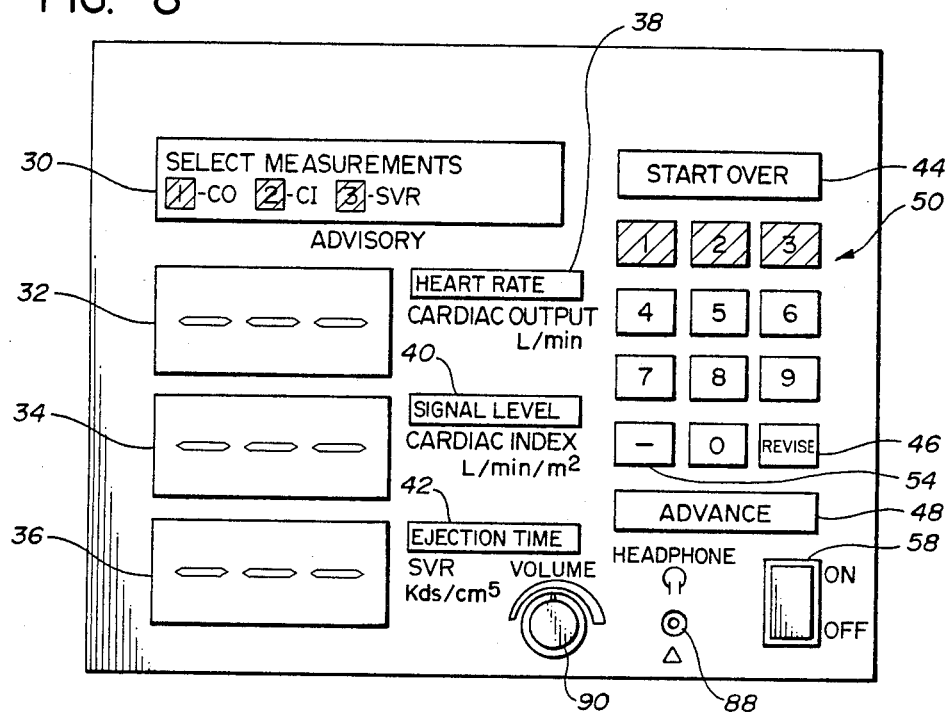
Figure 9:
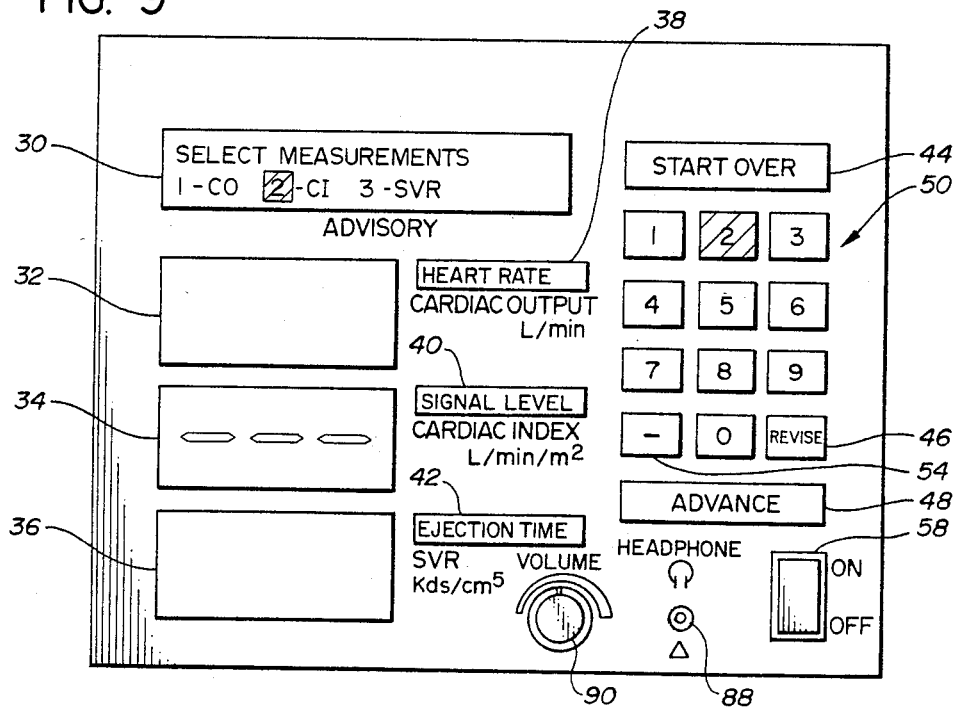
Figure 10:
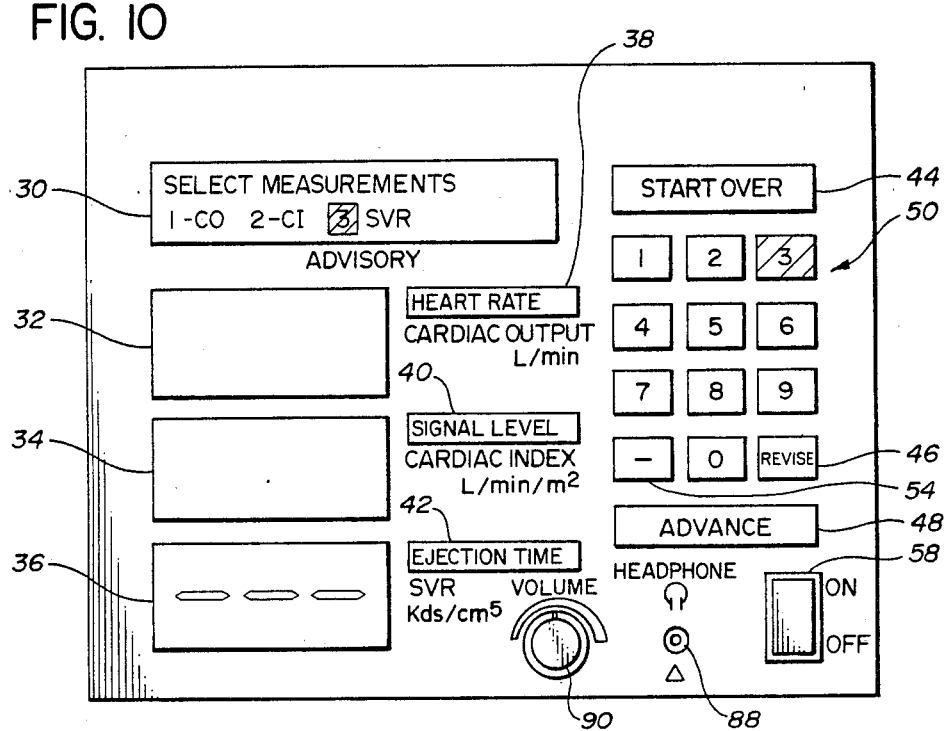
Figure 11:
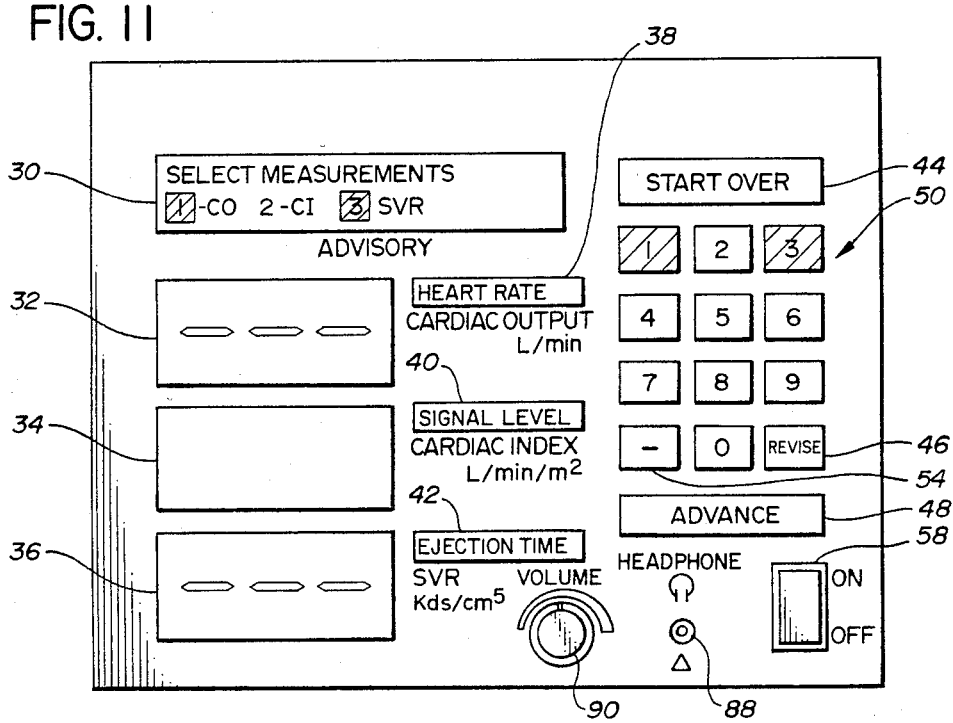
Figure 12:
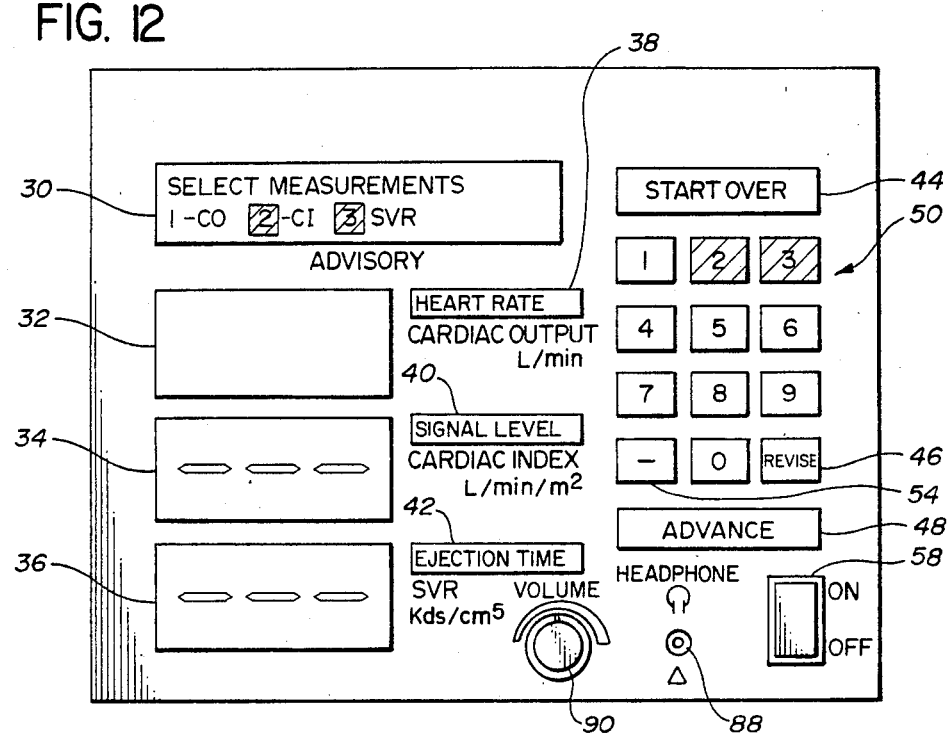
Figure 45B:
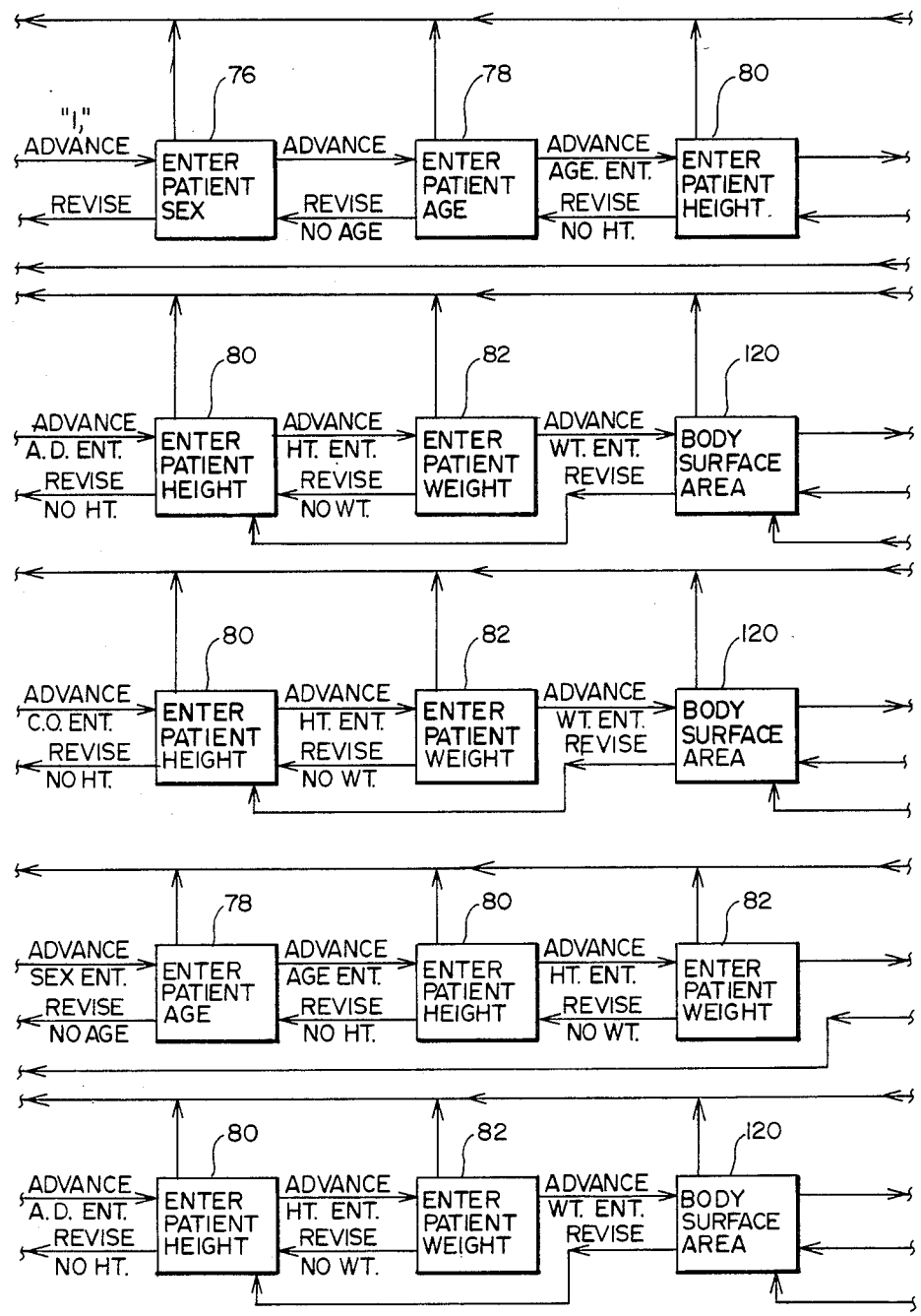
FIG. 45 shows the relationship among FIGS. 44A–44C which, collectively, show what is happening in the cardiac output monitoring apparatus as the operator interacts with that apparatus in the course of determining a patient's cardiac index.
Figure 45C:
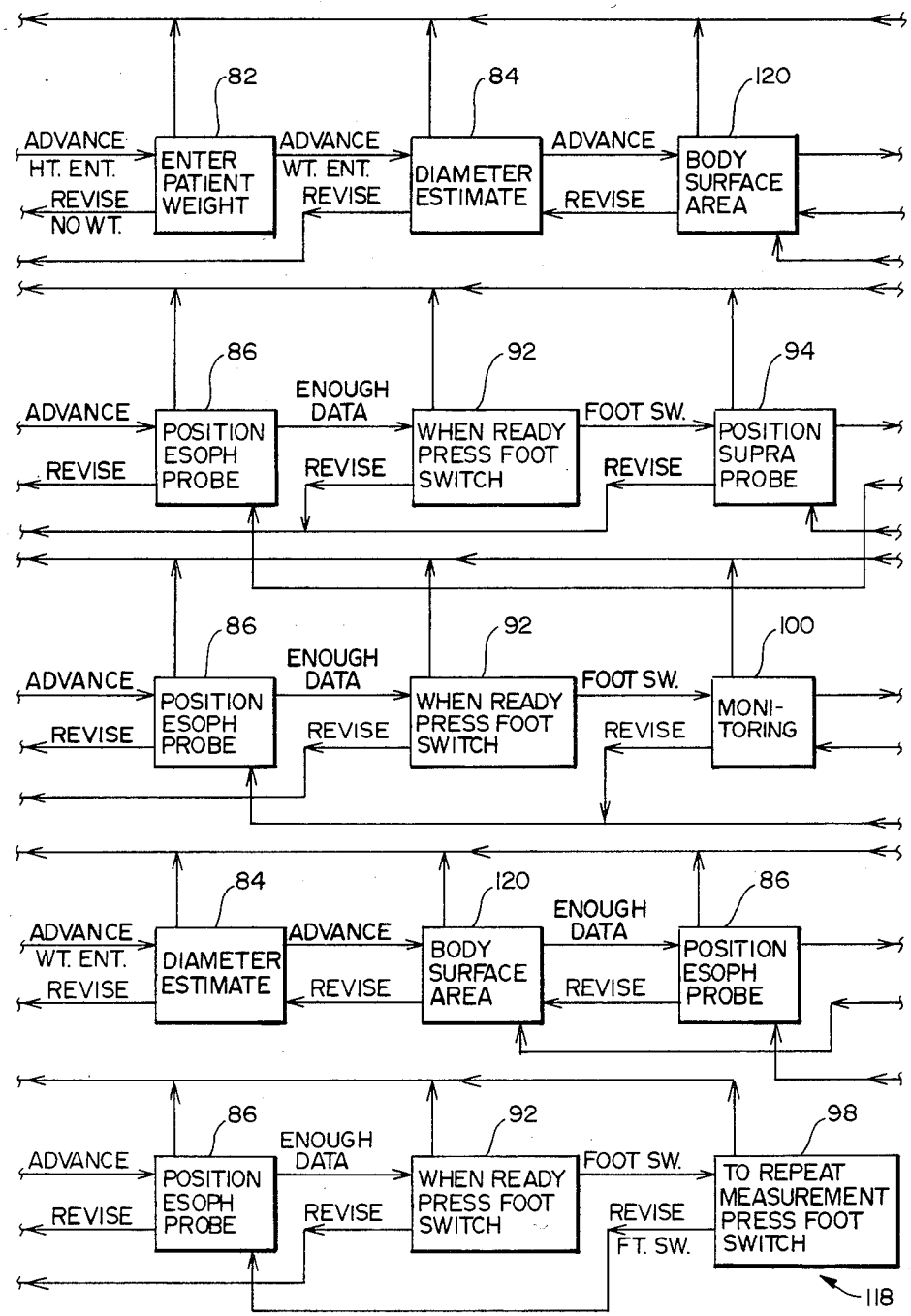
Figure 45D:
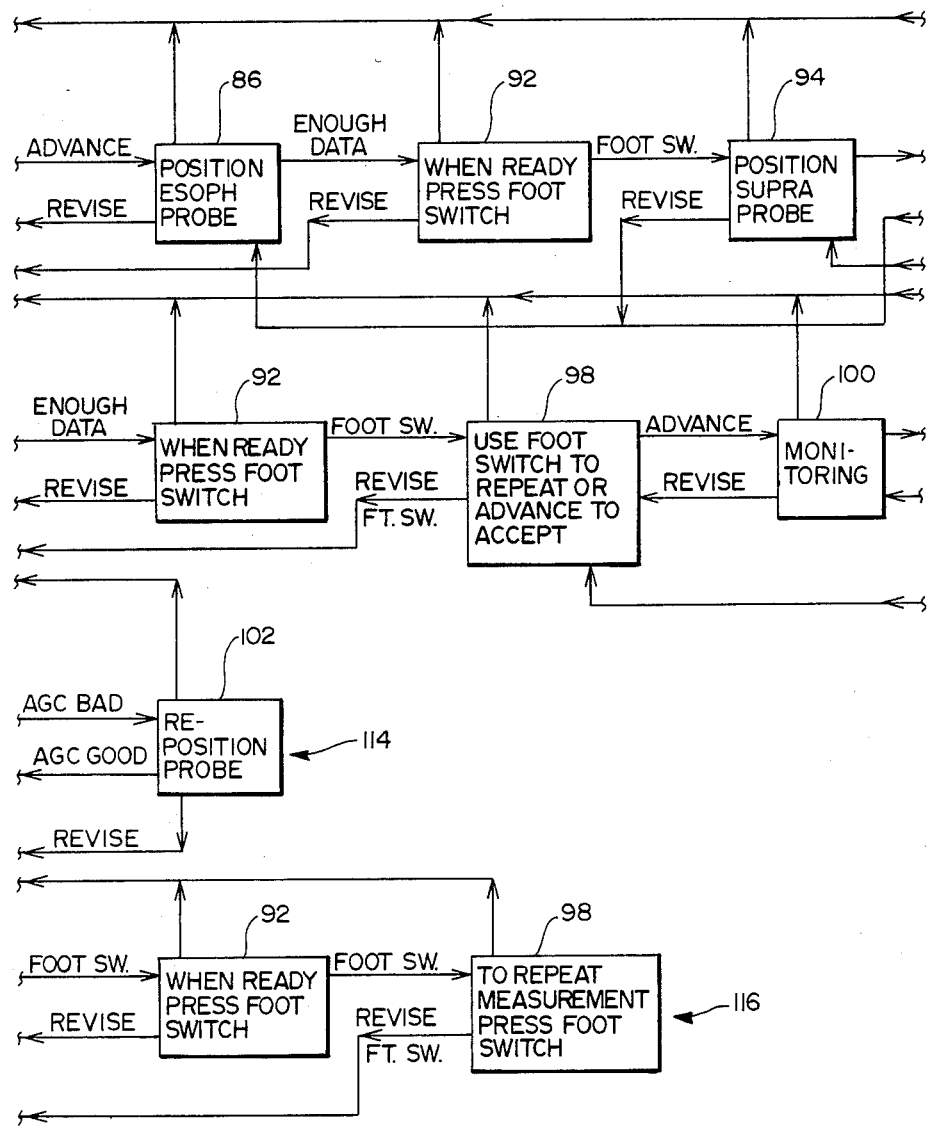
Figure 45E:
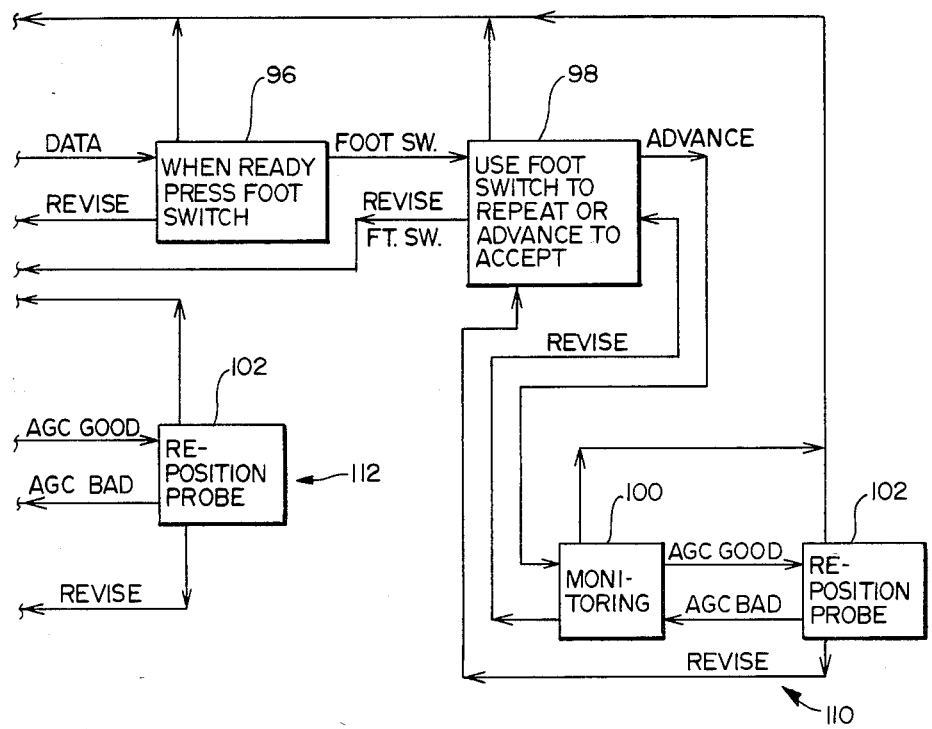

Referring still to the drawing, FIGS. 45A–C show the options available to the operator of cardiac monitor 26 if he presses key 2 to select cardiac index in response to the advisory SELECT MEASUREMENT shown in box 60 of FIG. 44A and in FIGS. 8 and 9.

Like that illustrated in FIGS. 44A–C, the protocol for determining cardiac index has five branches. These are designated 110, 112, 114, 116, and 118 in FIGS. 45A–C.

These branches contain sequences of steps for: (1) continuously measuring a patient's cardiac index employing a calibration factor determined by the suprasternal notch probe approach and a predictively determined aortic diameter; (2) monitoring the patient's cardiac index employing the same calibration method and a known aortic diameter; (3) monitoring the patient's cardiac index using a known calibration factor and a predictively determined measurement of the patient's aortic diameter; (4) providing a single or one-time measurement of the patient's cardiac index employing a predictively determined aortic diameter and a suprasternal notch probe-based calibration factor; and (5) providing a single or one-time measurement of the patient's cardiac index using a known aortic diameter and the suprasternal notch probe approach for determining an appropriate calibration factor.

Figure 29:
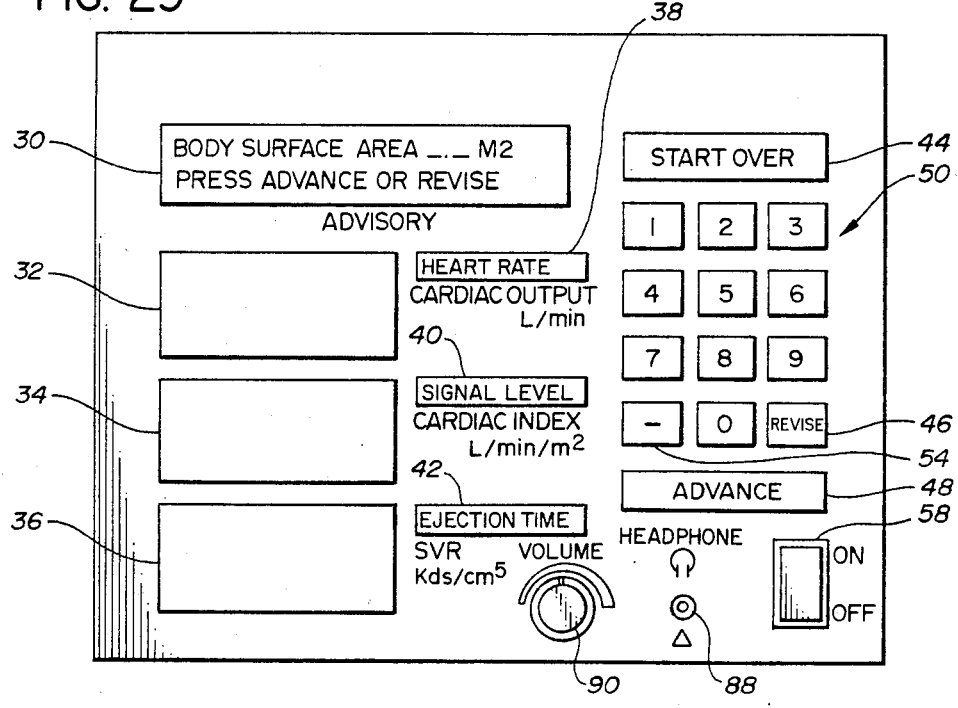
Figure 30:
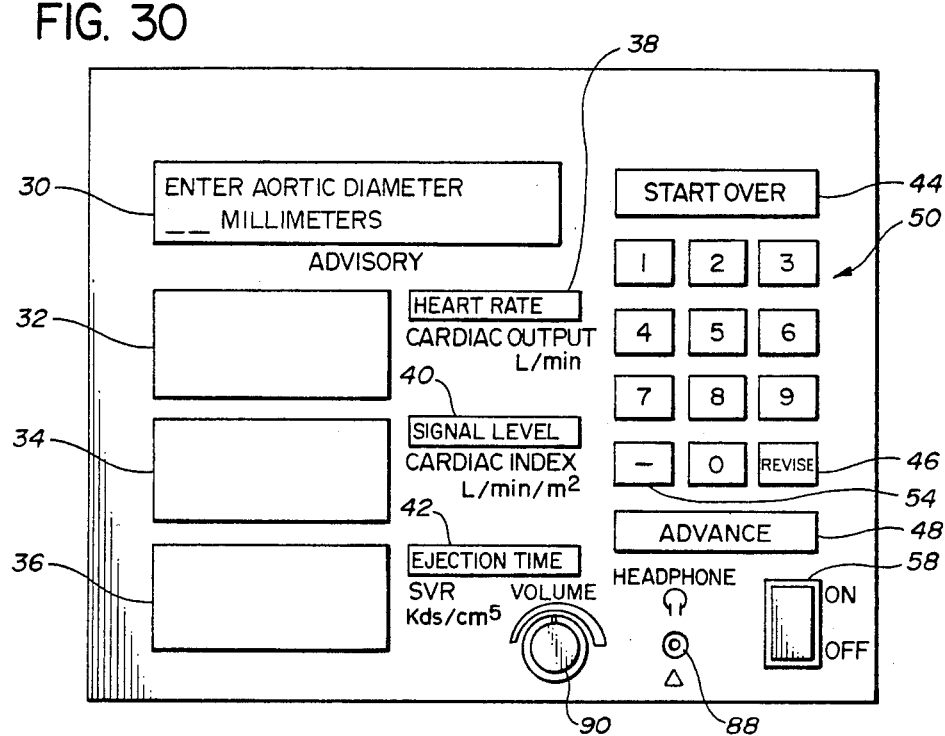
Figure 31:
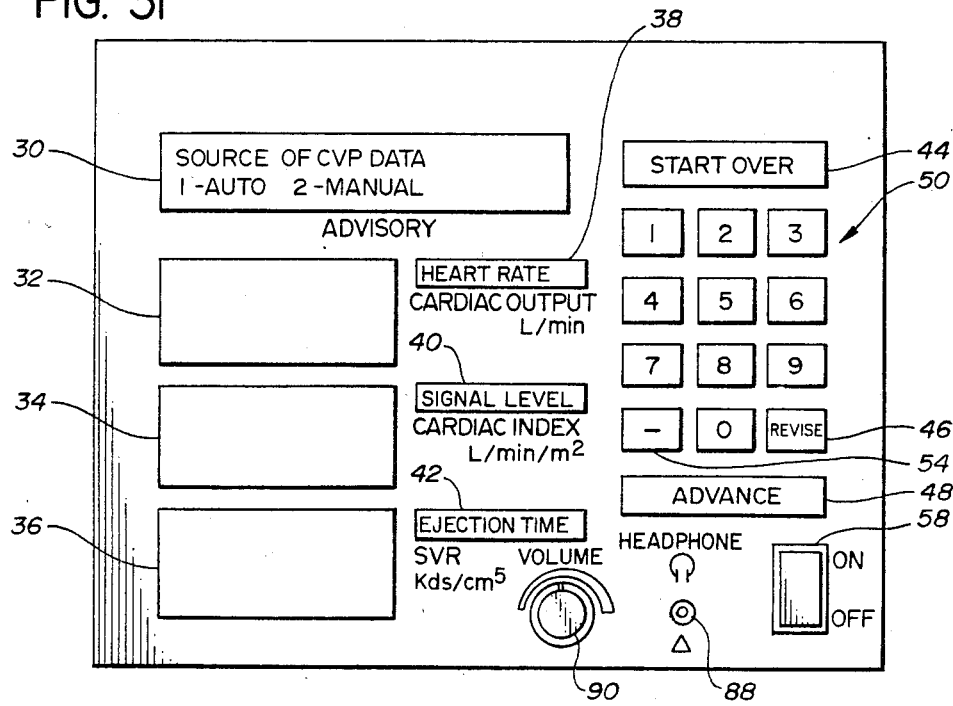
Figure 32:
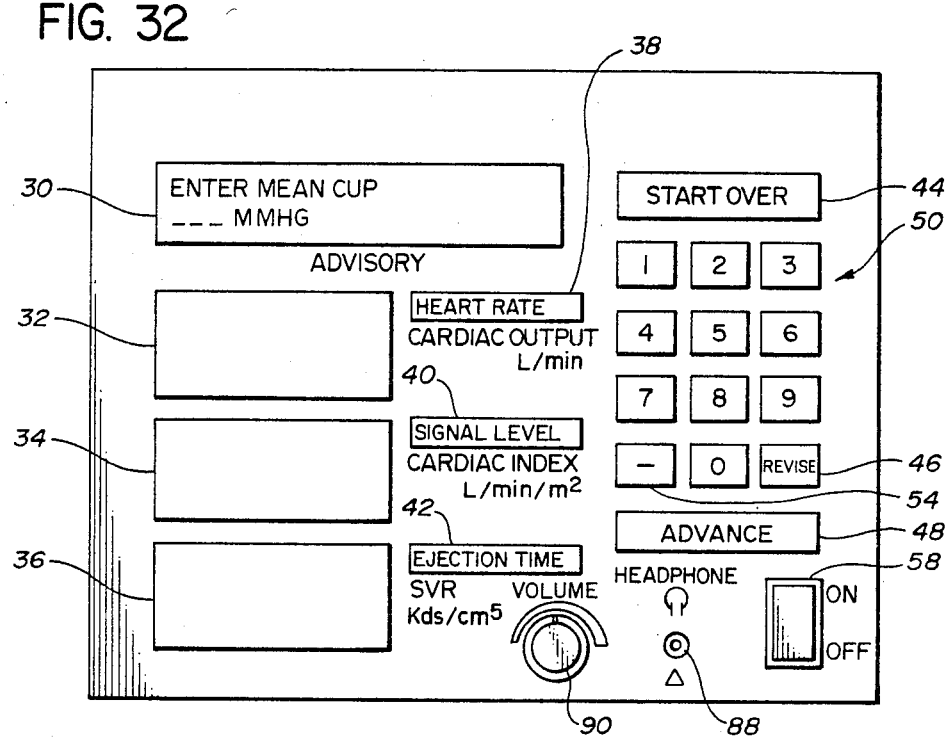
Figure 33:
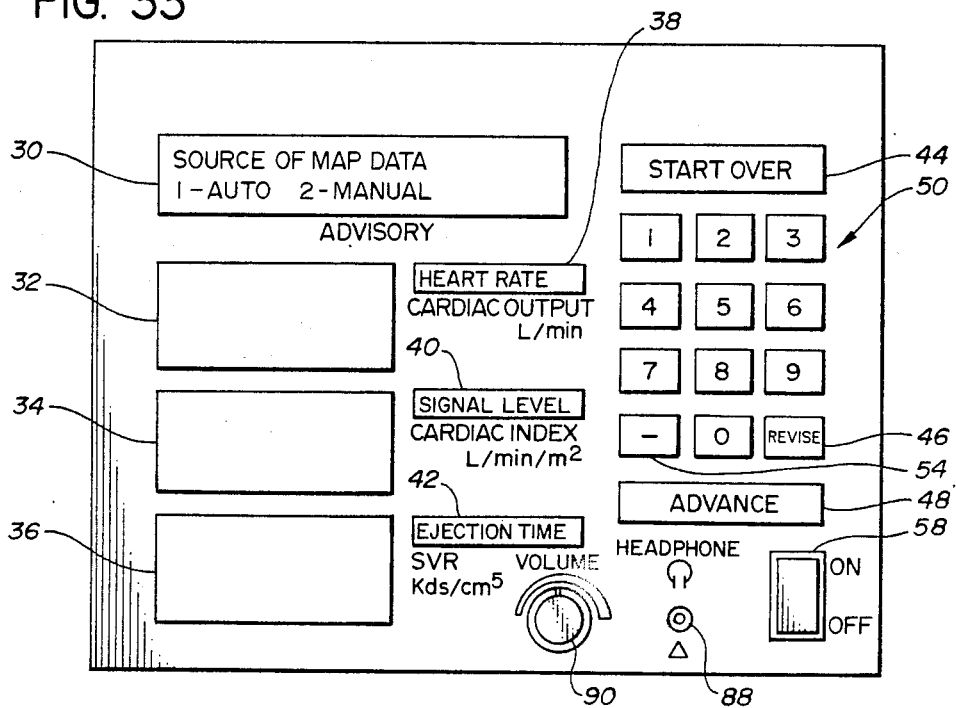
Figure 34:
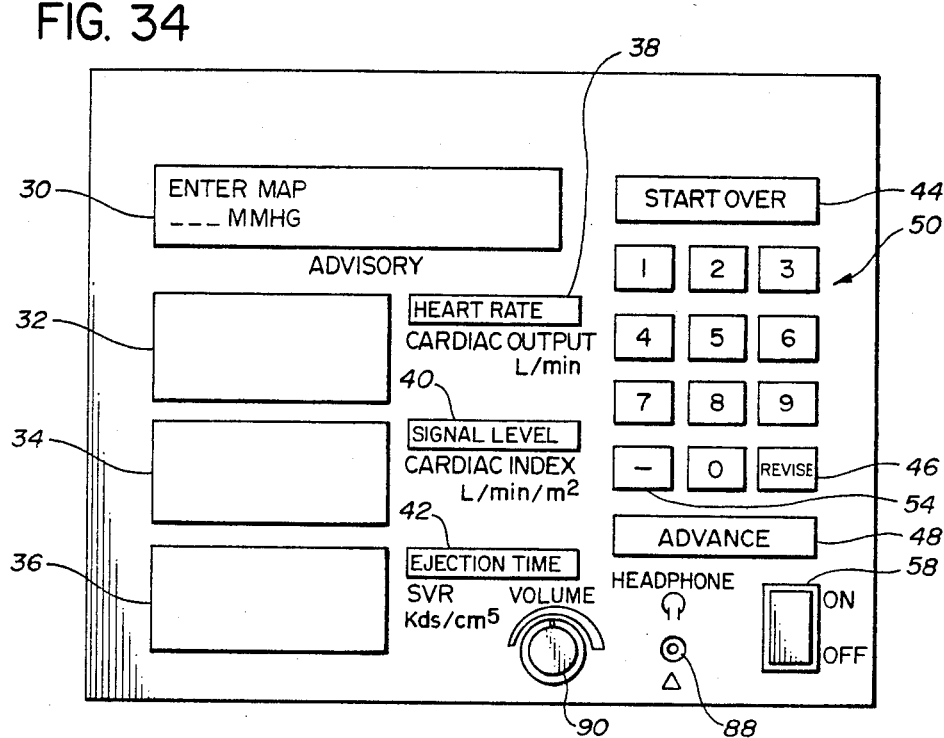
Figure 35:
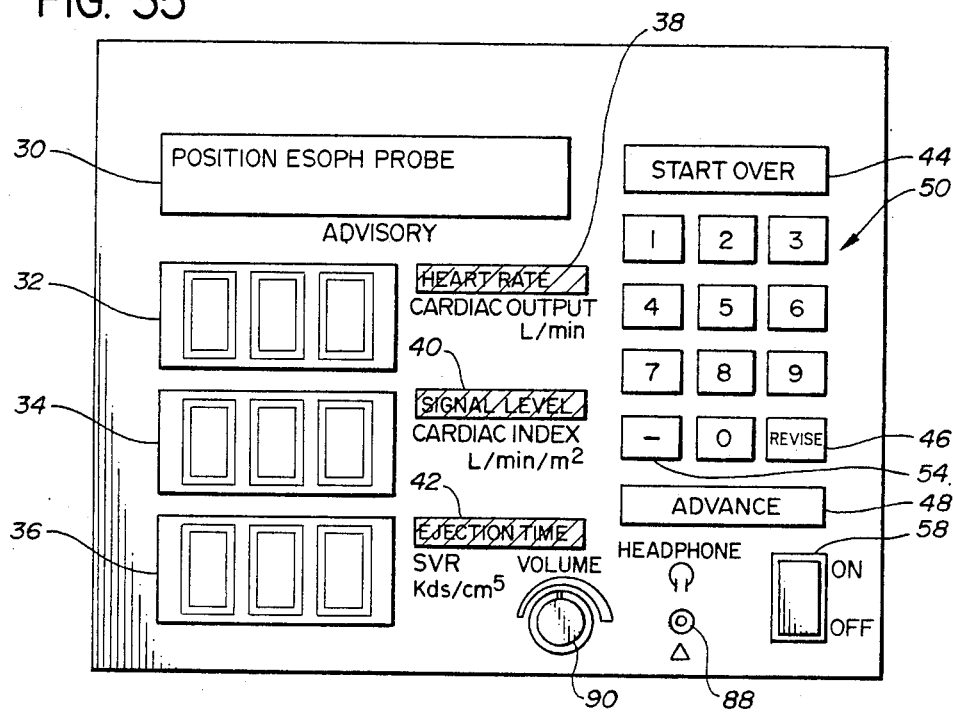

The sequence of steps in branch 110 is identical to that in branch 64 of the protocol depicted in FIGS. 44A–C except for the inclusion of the advisories: BODY SURFACE AREA SOURCE (FIG. 19), ENTER BODY SURFACE AREA (FIG. 20), and BODY SURFACE AREA, - - - $MM^2$ (FIG. 29). The third of these advisories is identified by reference character 120 in FIG. 45B; the other two are not shown in FIG. 45.

The advisory shown in FIG. 19 prompts the operator to elect to have the patient's body surface area calculated in cardiac monitor 26 from his height and weight or to elect to use a known value. If the latter option is elected, the pressing of ADVANCE key 48 following the election will ring up the instruction ENTER BODY SURFACE which the operator will carry out via keyboard 50.

If the operator elects to employ a calculated body surface area in measuring the patient's cardiac index, by pressing key 1, the calculated value will appear in message unit 30 with the BODY SURFACE AREA advisory.

Figure 20:
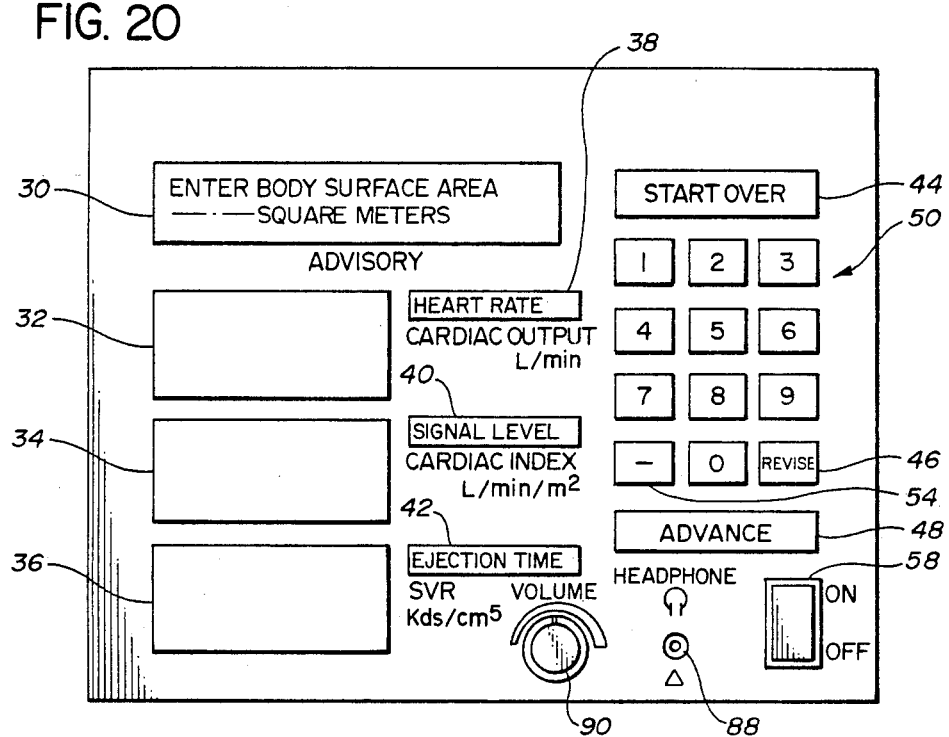

The sequence of steps in the second branch 112 of the cardiac index protocol is likewise identical to its counterpart branch 74 in the protocol shown in FIGS. 44A–C except for the inclusion of the advisories shown in FIGS. 19, 20, and 29.

Because the patient's height and weight area are employed to calculate the patient's body surface area, the sequence of steps in branches 114, 116, and 118 of the cardiac index measurement protocol also includes the advisories 80 (ENTER PATIENT'S HEIGHT) and 82 (ENTER PATIENT'S WEIGHT). The patient's height can be entered in inches (FIG. 24) or in centimeters (FIG. 25), and the patient's weight can be entered in pounds (FIG. 26) or kilograms (FIG. 27).

It will be remembered that cardiac monitor 26 is also designed to measure a patient's systemic vascular resistance.

The protocol for this measurement has not been illustrated because of its close similarity to those shown in FIGS. 44A–C and 45A–C as discussed above.

To make this measurement, cardiac monitor 18 must be supplied with the patient's CVP (central venous pressure) and MAP (mean arterial pressure). The operator may elect to have the necessary information supplied either automatically (see FIGS. 31 and 33) by depressing key 1 of keyboard 50 or manually by depressing key 2. If key 2 is depressed, pressing ADVANCE key 48 will bring up the advisory ENTER MEAN CVP (FIG. 32) and the advisory ENTER MAP (FIG. 34) at different points in the protocol.

The advisory messages shown in FIGS. 31–34 are displayed only if the systemic vascular resistance measurement has been elected by the operator.

Only one mode of supplying the central venous pressure and the mean arterial pressure may be selected. Entry of any subsequent selection deletes the previous one.

The LED displays show which methods of supplying CVP and MAP have been elected.

If the CVP and MAP are not updated within five minutes, dashes will appear in the systemic vascular resistance display. This indicates to the operator of cardiac monitor 26 that the CVP and MAP information needs to be replaced.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed is:

1. A method for ascertaining the cardiac output of a human patient, said method comprising the steps of: measuring the systolic velocity of the blood flowing through the patient's descending aorta with an ultrasonic probe inserted in the esophagus of the patient; determining the cross-sectional area of the patient's ascending aorta; and calculating the patient's cardiac output from said systolic velocity and said aortic area.

2. A method as defined in claim 1 in which the systolic velocity of the blood flowing through the patient's descending aorta is scaled upwardly to the velocity of the blood flowing through his ascending aorta before the calculation of the patient's cardiac output is made.

3. A method as defined in claim 2 wherein the systolic velocity of the blood flowing through the patient's descending aorta is scaled upwardly to the velocity of the blood flowing through his ascending aorta before the calculation of the patient's cardiac output is made by measuring the systolic velocity of the blood flowing through the patient's ascending aorta, computing a scaling factor from the aforesaid systolic velocity and the systolic velocity of the blood flowing through the patient's descending aorta, and employing said factor to scale the systolic velocity of the patient's descending aorta blood flow as aforesaid.

4. A method as defined in claim 3 wherein the velocity of the blood flowing through the patient's ascending aorta is measured with an ultrasonic suprasternal notch probe.

5. A method as defined in claim 1 wherein said cardiac output is calculated by: generating a signal representative of the systolic velocity of the blood flowing through the patient's descending aorta; upwardly scaling that signal from a calibration signal representing a relationship between said systolic velocity representative signal and the velocity of the blood flowing through the patient's ascending aorta; subjecting said first systolic velocity signal to frequency spectrum analysis to produce a multicomponent velocity profile signal; integrating said velocity profile signal with respect to time to thereby produce a systolic velocity integral; computing stroke volume as a function of said cross-sectional area and said systolic velocity integral; summing the stroke volumes thus determined for n beats of the patient's heart; and dividing the resulting sum by the time spanning said n beats.

6. A method as defined in claim 1 wherein the patient's aortic area is predictively determined by:
 a. determining the age and sex of said patient;
 b. measuring the height and weight of said patient;
 c. entering the age, sex, height, and weight data thus obtained into a data processing means;
 d. instructing the data processing means to execute a program for converting said data to a value indicative of the diameter of the patient's aorta; and
 e. converting the value indicative of the diameter of the patient's ascending aorta into a numerical value indicative of the area of the patient's ascending aorta.

7. A method as defined in claim 6 wherein said data processing means is instructed to execute a program which is capable of solving the equation:

$$AD = C_1 + [C_2 \times AGE] + [C_3 \times SEX] + [C_4 \times HEIGHT] + [C_5 \times WEIGHT]$$

where:
 AD is aortic diameter
 $C_1$–$C_5$ are constants,
 AGE is the age of the patient in years,
 SEX is 0 if the patient is a male and one if the patient is a female,
 HEIGHT is the height of the patient in inches, and
 WEIGHT is the weight of the patient in pounds.

8. A method for measuring the cardiac output of a human patient, said method comprising the steps of: determining the cross-sectional area of the patient's ascending aorta; generating a signal representative of the systolic velocity of the blood flowing through the patient's descending aorta with an ultrasonic probe inserted in the esophagus of the patient; upwardly scaling that signal from a calibration signal representing a relationship between said systolic velocity representative signal and the velocity of the blood flowing through the patient's ascending aorta; subjecting said first systolic velocity signal to frequency spectrum analysis to produce a multicomponent velocity profile signal; integrating said velocity profile signal with respect to time to thereby produce a systolic velocity integral; computing stroke volume as a function of said cross-sectional area and said systolic velocity integral; summing the stroke volumes thus determined for n beats of the patient's heart; and dividing the resulting sum by the time spanning said n beats.

9. A method of determining the cardiac index of a human patient which includes the steps of: computing the cardiac output of the patient by determining the cross-sectional area of the patient's ascending aorta, generating a signal representative of the systolic velocity of the blood flowing through the patient's descending aorta with an ultrasonic probe inserted in the esophagus of the patient, upwardly scaling that signal from a calibration signal representing a relationship between said systolic velocity representative signal and the velocity of the blood flowing through patient's ascending aorta, subjecting said first systolic velocity signal to frequency spectrum analysis to produce a multicomponent velocity profile signal, integrating said velocity profile signal with respect to time to thereby produce a systolic velocity integral, computing stroke volume as a function of said cross-sectional area and said systolic velocity integral, summing the stroke volumes thus determined for n beats of the patient's heart, and dividing the resulting sum by the time spanning said n beats to determine said cardiac output, and dividing the cardiac output of the patient by his body surface area.

10. Apparatus for measuring the cardiac output of a human patient, said apparatus including: means for measuring the systolic velocity of the blood flowing through the patient's aorta, said means including an ultrasonic esophageal probe; means for calculating the cross-sectional area of the patient's aorta from his height, weight, age, sex; and means for calculating the cardiac output of the patient from the thus determined systolic flow velocity and aortic diameter.

11. Apparatus as defined in claim 10 which includes means for generating a signal representative of the systolic velocity of the blood flowing through the patient's descending aorta; means for upwardly scaling that signal from a calibration signal representing a relationship between said systolic velocity representative signal and the velocity of the blood flowing through the patient's ascending aorta; means for performing a frequency spectrum analysis of said first systolic velocity signal to thereby produce a multicomponent velocity profile signal; means for integrating said velocity profile signal with respect to time to thereby produce a systolic velocity integral; means for computing stroke volume as a function of said cross-sectional area and said systolic velocity integral; means for summing the stroke volumes thus determined for n beats of the patient's heart; and means for dividing the results by the time spanning said n beats.

12. Apparatus as defined in claim 11 which includes an ultrasonic suprasternal notch probe for providing a one-time or calibration measurement of the systolic velocity of the blood flowing through the patient's ascending aorta, means for computing a scaling factor from that velocity and the systolic flow velocity of the blood flowing through the patient's descending aorta, and means for producing said second signal from said just-mentioned systolic flow velocity and said scaling factor.

13. Apparatus as defined in claim 10 which includes a touch sensitive display means via which an operator can interact with the apparatus in the course of measuring the patient's cardiac output, said display means including means for displaying instructions to said operator and information on the status of the apparatus and the patient's cardiac output.

14. Apparatus as defined in claim 10 which includes means for dividing said cardiac output of the patient by his body surface area and thereby obtaining the cardiac index of the patient.

15. Apparatus as defined in claim 10 which includes means for dividing a value representing the blood pressure of the patient by the cardiac output of the patient and thereby obtaining his systemic vascular resistance.

16. Apparatus as claimed in claim 10 which includes:
   a. means into which numerical values representing the age, set, height, and weight of the patient can be written; and
   b. data processing means for: (i) converting said numerical values into one indicative of the diameter of the patient's aorta, and (ii) converting the value indicative of the diameter of the patient's ascending aorta into a numerical value indicative of the area of the patient's ascending aorta.

17. Apparatus as defined in claim 16 wherein said data processing means includes means for solving the equation:

$$AD = C_1 + [C_2 \times AGE] + [C_3 \times SEX] + [C_4 \times HEIGHT] + [C_5 \times WEIGHT]$$

where:
AD is aortic diameter,
$C_1$–$C_5$ are constants
AGE is the age of the patient in years,
SEX is 0 if the patient is a male and one if the patient is a female,
HEIGHT is the height of the patient in inches, and
WEIGHT is the weight of the patient in pounds.

18. A method for measuring the systemic vascular resistance of a human patient, said method comprising the steps of: determining the cross-sectional area of the patient's ascending aorta; generating a signal representative of the systolic velocity of the blood flowing through the patient's descending aorta with an ultrasonic probe inserted in the esophagus of the patient; upwardly scaling that signal from a calibration signal representing a relationship between said systolic velocity representative signal and the velocity of the blood flowing through the patient's ascending aorta; subjecting said first systolic velocity signal to frequency spectrum analysis to produce a multicomponent velocity profile signal; integrating said velocity profile signal with respect to time to thereby produce a systolic velocity integral; computing stroke volume as a function of said cross-sectional area and said systolic velocity integral; summing the stroke volumes thus determined for n beats of the patient's heart; and dividing the resulting sum by a value representing the inverse of the blood pressure of the patient.

19. A method as defined in claim 18 wherein said value has components representing both the patient's central venous pressure and his mean arterial pressure.

20. A method of determining the cardiac index of a human patient which includes the steps of computing the cardiac output of the patient by determining the cross-sectional area of the patient's ascending aorta, generating a signal representative of the systolic velocity of the blood flowing through the patient's descending aorta with an ultrasonic probe inserted in the esophagus of the patient, upwardly scaling that signal from a calibration signal representing a relationship between said systolic velocity representative signal and the velocity of the blood flowing through the patient's ascending aorta, subjecting said first systolic velocity signal to frequency spectrum analysis to produce a multicomponent velocity profile signal, integrating said velocity profile signal with respect to time to thereby produce a systolic velocity integral, computing stroke volume as a function of said cross-sectional area and said systolic velocity integral, summing the stroke volumes thus determined for n beats of the patient's heart, dividing the resulting sum by the time spanning said n beats to determine said cardiac output, and dividing a value representing the inverse of the blood pressure of the patient by the cardiac output of the patient.

21. A method as defined in claim 20 wherein said value has components representing both the patient's central venous pressure and his mean arterial pressure.

* * * * *